United States Patent [19]
Ouchi et al.

[11] Patent Number: 5,993,379
[45] Date of Patent: Nov. 30, 1999

[54] FLUID SPLASHING PREVENTIVE DEVICE

[75] Inventors: Teruo Ouchi, Tokyo; Kenjiro Ooshima, Gifu, both of Japan

[73] Assignees: Asahi Kogaku Kogyo Kabushiki Kaisha, Tokyo; Kenjiro Ooshima, Gifu, both of Japan

[21] Appl. No.: 08/917,274

[22] Filed: Aug. 25, 1997

[30]   Foreign Application Priority Data

| Feb. 25, 1996 | [JP] | Japan | 9-040192 |
| Aug. 26, 1996 | [JP] | Japan | 8-223878 |
| Aug. 26, 1996 | [JP] | Japan | 8-223879 |
| Aug. 26, 1996 | [JP] | Japan | 8-223880 |
| Oct. 1, 1996 | [JP] | Japan | 8-260368 |
| Oct. 1, 1996 | [JP] | Japan | 8-260369 |
| Feb. 14, 1997 | [JP] | Japan | 9-029913 |
| Feb. 14, 1997 | [JP] | Japan | 9-029914 |
| Feb. 26, 1997 | [JP] | Japan | 9-041723 |
| Jul. 3, 1997 | [JP] | Japan | 9-177893 |

[51] Int. Cl.$^6$ .................................................. A61B 1/012
[52] U.S. Cl. ........................................... 600/119; 600/154
[58] Field of Search ................................... 600/104, 119, 600/121, 122, 123, 124, 125; 128/849, 851, 852, 855; 604/385.1; 602/41, 79

[56]   References Cited

U.S. PATENT DOCUMENTS

| 4,261,343 | 4/1981 | Ouchi et al. . |
| 4,834,068 | 5/1989 | Gottesman . |
| 5,337,731 | 8/1994 | Takahashi et al. . |
| 5,359,991 | 11/1994 | Takahashi et al. . |
| 5,363,843 | 11/1994 | Daneshvar . |

FOREIGN PATENT DOCUMENTS

| 3233564 | 4/1983 | Germany . |
| 8809674 | 12/1988 | Germany . |
| 2109241 | 6/1983 | United Kingdom . |

OTHER PUBLICATIONS

A European Search Report dated Feb. 5, 1998.

*Primary Examiner*—John P. Leubecker
*Attorney, Agent, or Firm*—Greenblum & Bernstein, P.L.C.

[57]   ABSTRACT

A foul fluid splashing prevention device for an endoscope, which prevents foul fluids inside the body cavity from splashing, even when they spray out from a manipulating portion side of the endoscope. The foul fluid splashing prevention device includes a foul fluid absorbing member made of flexible water-absorbing material for absorbing the foul fluids that leak out of an external opening of the endoscope. The splashing prevention device further includes a retaining member, which is detachably disposed at the manipulating part to retain the foul fluid absorbing member when the foul fluid absorbing member covers the external opening.

51 Claims, 75 Drawing Sheets

FLUID SPLASHING PREVENTIVE DEVICE

BACKGROUND OF THE INVENTION

The present invention relates to a fluid splashing preventive device for an endoscope which prevents the splashing of fluids, such as foul fluids, from an external opening that is provided at a manipulating part and is in communication with a fluid path, that opens at an inserted part. The present invention is applicable to not only the endoscope itself but also to an endoscope insertion guiding device that facilitates the insertion of the endoscope into deep parts of the large intestine or into the small intestine.

Generally with an endoscope, a forceps channel for passing through operative instruments extends through the inserted part. The front end exit of this forceps channel is opened at the front end of the inserted part and the base end entrance of this channel is opened at the manipulating part.

However, with the forceps channel as it is, the internal pressure of the body cavity can cause fluids, such as foul fluids inside the body cavity to pass through the forceps channel and escape from the entrance opening, thereby causing contamination of the operator and the surroundings.

Thus, in order to prevent the escape of such fluids while enabling the insertion and removal of operative instruments into and from the forceps channel, a so-called forceps plug, comprised for example of a rubber plug with a slit formed therein, is fitted to the entrance opening part of the forceps channel.

However, when an operative instrument is passed through the forceps plug, the slit of the rubber valve is spread, causing gaps to form between the rubber plug and the outer peripheral surface of the operative instrument at end portions of the slit, and in many cases, internal fluids are likely to escape from such portions. This problem is serious especially in the case of an operative instrument having a coil pipe as a sheath since such an operative instrument has spiral gaps at its outer peripheral surface.

Also, in the case of an operative instrument in which a manipulating wire, etc. is retractably inserted through a sheath, there is a gap between the sheath and the manipulating wire, and internal fluids can escape through this portion.

Furthermore, although the suction control valve and air/water conveying control valve disposed at the manipulating part are sealed by means of an O-ring fitted therein, foul body cavity fluids can escape from the leak port, etc. of the control valve when the O-ring becomes worn or damaged.

When fluids inside the body cavity escape from the operative instrument insertion entrance as described above, the fluids can splash about onto the surroundings and onto the hands and face of the operator, thereby causing an extremely unsanitary condition to occur. However, it is difficult to completely prevent such escape of fluids from the inside of the body cavity.

A similar problem arises in case where an endoscope insertion guiding device is used in combination with the endoscope.

In many cases where an endoscope is simply inserted from the anus to perform endoscopy of the large intestine or small intestine, the sigmoid colon portion immediately ahead of the anus bends and thus hinders the insertion of the endoscope deeply. To cope with this difficulty, generally, an insertion guiding device called a sliding tube is used to shorten and straighten out the sigmoid colon.

FIG. 87 shows an example of a sliding tube 90. The sliding tube 90 is a somewhat flexible pipe-shaped object with a length of about 40 cm. The sliding tube has such a thickness as to permit the insertion of the inserted part of an endoscope, and is provided with the proximal mouthpiece 91 slightly thicker for preventing entry inside the anus entirely.

Also, a sponge member 93, impregnated with lubricant and having a slit 92 formed at the center, is disposed inside the proximal mouthpiece 91, and the inserted part of the endoscope is made to pass through the sponge member 93 while spreading the slit (92) portion.

FIG. 88 shows the condition in which the sliding tube 90 is used to insert the inserted part 2 of the endoscope 1 into the large intestine from the anus of a patient.

As a general procedure, the sliding tube 90 is first put in the condition for straightening the colon portion using the inserted part 2 as a guide. The inserted part 2, which has been inserted through the sliding tube 90, is then gradually pushed in deeper while being pushed and pulled.

To insert the inserted part 2 into the large intestine in the above manner, the large intestine must be expanded to some degree by feeding air into the large intestine by means of an air conveying system provided in the endoscope. Thus the pressure inside the large intestine increases.

As a result, the air inside the large intestine blows out like flatus via the gap between the anus and the sliding tube 90 or the gap between the sliding tube 90 and the inserted part 2. Since the patient will be subject to great pain if the air from the inside of the large intestine is not expelled at this time, the expulsion of air from the inside of the intestine is unavoidable.

However, when air blows out from the anus part, the feces, that have become liquid-like upon being dissolved in purgative, etc., escape along the air. When the air blows out, the slit (92) portion of sponge member 93 opens as shown in FIG. 89 and the air blows out instantaneously from this portion. Thus in many cases, the feces mixed with the air are scattered over a wide range.

Also, as the inserted part 2 is pushed and pulled, the feces mixed with the lubricant are transferred from the sponge member 93 to the pulled-out portion and contaminate the operator's hands. Likewise, the operator's hands also become dirty with feces when inserted part 2 is pulled out of the anus upon completion of endoscopy.

The operator himself will not have a problem since he usually wears rubber gloves in such cases. However, since the operator must touch equipment in the surroundings with the hands (gloves) that have been soiled with feces in many cases, such equipment in the surroundings become contaminated.

SUMMARY OF THE INVENTION

Thus, an object of the present invention is to present a fluid splashing prevention device for an endoscope by which fluids inside the body cavity can be prevented from splashing even when they escape from the manipulating part side or the like of the endoscope, so that endoscopy can be performed in a sanitary manner.

In order to attain the above-noted and/or other object(s), the present invention provides a fluid splashing preventive device adapted for use with an endoscope. The endoscope defines an external opening which is in communication with a body cavity and through which fluids within the body cavity can escape. The fluid splashing preventive device includes a retaining member provided to the endoscope, and a flexible, fluid absorbing member mountable onto the endoscope by the retaining member. The flexible, fluid absorbing member covers the external opening and absorbs the escaping fluids.

The present invention further provides a fluid splashing preventive device for an endoscope having an insertion part and a manipulation part. The manipulation part has an external opening which is in communication with a body cavity through the insertion part. The fluid splashing preventive device includes a retaining member provided to the endoscope, and a first flexible, fluid absorbing member mountable onto the manipulation part in the vicinity of the external opening by the retaining member.

The present invention further provides a fluid splashing preventive device for a flexible, tubular endoscope insertion guiding device inserted into an opening in a body to guide an inserted part of an endoscope toward a body cavity. The guiding device has a proximal end through which the inserted part of the endoscope is inserted into an inside of the guiding device. The fluid splashing preventive device includes a retaining member provided to the proximal end, and a flexible, fluid absorbing member mountable onto the guiding device in the vicinity of the proximal end by the retaining member.

In an embodiment, a foul fluid splashing prevention device for an endoscope is provided, which prevents the splashing or foul fluids from an external opening that is provided at a manipulating part, connected to the base end of the inserted part of the endoscope, and is in communication with a fluid path, that opens at the inserted part. The foul fluid splashing prevention device for an endoscope is made up of a foul fluid absorbing member made of flexible water-absorbing material for absorbing the foul fluids that leak out of the external opening at the outer side of the external opening and a retaining member, which is detachably disposed at the manipulating part to retain the foul fluid absorbing member in the condition where the foul fluid absorbing member covers the external opening from the outer side.

The material of the foul fluid absorbing member can be gauze, sponge, open-cell material, water-impregnable nonwoven fabric, or high molecular weight water-impregnable polymer. The retaining member can be a cord-like member that is passed through a cord path formed in the foul fluid absorbing member.

The retaining member can also be formed from a stretchable, endless member or can be formed from an end-to-end member having engaging parts at both ends that engage with each other. The retaining member can also be formed from an end-to-end member having engaging parts at both ends that engage with the manipulating part.

Furthermore, the foul fluid absorbing member can be formed so as to cover not only the external opening but a part of the grip portion of the manipulating part as well. The external opening may be an entrance for inserting an operative instrument into the forceps channel or a leak port formed on the control valve for conveying air or water or for performing suction.

With the embodiment of the present invention, since a foul fluid absorbing member, formed from a flexible, water-absorbing material, is attached at a position where it covers, from the outer side, an external opening provided at the manipulating part so as to be in communication with a fluid path that opens at the inserted part of the endoscope, foul fluids within the body cavity will be absorbed and prevented from splashing even when they escape from the external opening of the manipulating part. Thus, endoscopy can be performed in a sanitary manner. Also, the foul fluid splashing prevention device can be readily attached, detached, or replaced whenever necessary.

As another embodiment, a foul fluid splashing prevention device for an endoscope is provided, which is characterized by a foul fluid absorbing member formed from a flexible water-absorbing material being detachably disposed at the outer surface portion of the manipulating part of an endoscope. The foul fluid absorbing member is positioned so as to cover a forceps channel entrance provided near the manipulating part.

The foul fluid absorbing member may be made to be adhered onto the outer surface of the manipulating part, or the entrance portion of the forceps channel may be protruded from the manipulating part. A hole that engages with this protruded portion may be formed on the foul fluid absorbing member.

With the embodiments of the present invention, since a foul fluid absorbing member formed from a flexible water-absorbing material is detachably provided at the outer surface portion of the manipulating part of an endoscope and this foul fluid absorbing member is disposed so as to cover the entrance of the forceps channel, foul fluids within the body cavity are prevented from splashing outward from the entrance of the forceps channel. Thus endoscopy can be performed in a sanitary manner. Furthermore, the foul fluid splashing prevention device can be attached, detached, or replaced readily whenever necessary.

As another embodiment of the present invention, a foul fluid splashing prevention device for an endoscope is provided, which is characterized in that a foul fluid absorbing member, that is formed from flexible water-absorbing material and that is for covering an operative instrument insertion entrance disposed at the tip of a protrusion formed on the manipulating part of an endoscope, is retained in a detachably attached manner at the protrusion.

A forceps plug, which is substantially closed and which becomes open by an operative instrument upon the insertion of the operative instrument, can be detachably mounted to the operative instrument insertion entrance part. The removal of the foul fluid absorbing member from the protrusion can be prevented by this forceps plug.

Also, a forceps plug, which is substantially closed and which becomes open by an operative instrument upon the insertion of the operative instrument, may be detachably mounted to the operative instrument insertion entrance part. A member for preventing the removal of the foul fluid absorbing member from the protrusion may be provided as a separate member from the forceps plug.

Furthermore, a hole into which the operative instrument insertion entrance part is inserted, may be formed in the foul fluid absorbing member. A presser part for retaining the foul fluid absorbing member may be formed on the forceps plug or the abovementioned separate member. The foul fluid absorbing member may be sandwiched between the presser part and the manipulating part or protrusion.

With the embodiment of the present invention, since a foul fluid absorbing member, which is formed from flexible water-absorbing material and is for covering the operative instrument insertion entrance of an endoscope, is provided, foul fluids within the body cavity are prevented from splashing outward from the operative instrument insertion entrance, thus enabling endoscopy to be performed in a sanitary manner. Also, the inserted part, etc, of the endoscope can be wiped with the foul fluid absorbing member immediately after the completion of endoscopy.

Furthermore, since the foul fluid absorbing member is detachably retained at a protrusion of the manipulating part at which the operative instrument insertion entrance is disposed, the foul fluid absorbing member can be readily replaced, etc., whenever necessary.

As another embodiment of the present invention, a foul fluid splashing prevention device for an endoscope is provided, which is characterized in that a foul fluid absorbing member, which is formed from flexible water-absorbing material and which is for covering an operative instrument insertion entrance disposed at the manipulating part of an endoscope, is mounted in a detachable and attachable manner near the operative instrument insertion entrance by means of pressure-sensitive adhesion.

The operative instrument insertion entrance may be disposed at the tip of a protrusion formed at the manipulating part and the foul fluid splashing absorbing member may be attached by pressure-sensitive adhesion to the outer peripheral surface of this protrusion.

Alternatively, the operative instrument insertion entrance may be disposed at the tip of a protrusion formed at the manipulating part and the foul fluid splashing absorbing member may be attached by pressure-sensitive adhesion across the outer peripheral surface of the protrusion and the outer peripheral surface of the manipulating part.

The operative instrument insertion entrance may also be disposed at a flat portion of the manipulating part and the foul fluid absorbing member may be attached by pressure-sensitive adhesion to this flat portion.

With this embodiment of the present invention, since a foul fluid absorbing member, which is formed from flexible water-absorbing material and which is for covering an operative instrument insertion entrance disposed at the manipulating part of an endoscope, is mounted in a detachable and attachable manner near the operative instrument insertion entrance by means of pressure-sensitive adhesion, foul body cavity fluids are prevented from splashing out from the operative instrument insertion entrance. Thus endoscopy can be performed in a sanitary manner and the foul fluid absorbing member can readily be reattached and replaced, etc., whenever necessary.

As another embodiment of the present invention, a contamination prevention device fastener for an endoscope is provided, which serves to attachably and detachably retain a foul fluid absorbing member formed of a flexible water absorbing material in a state where the outer wall surface near the operative tool insertion entrance of an endoscope is covered. The fastener is formed of an elastic material into a shape of a horseshoe-like cross section, and is fixed in a state where the outer wall surface of the endoscope is clamped from the outside by its own resiliency with the foul fluid absorbing member sandwiched between itself and the outer wall surface of the endoscope.

Furthermore, a pair of foul fluid absorbing members, i.e. the foul fluid absorbing member for covering the outer wall surface on the upper side of the operative tool insertion entrance of the endoscope and the foul fluid absorbing member for covering the outer wall surface on the lower side thereof may be provided so as to be separately retained with independent fasteners.

Furthermore, the foul fluid absorbing member for covering the outer wall surface on the upper side of the operative tool insertion entrance of the endoscope and the foul fluid absorbing member for covering the outer wall surface on the lower side thereof may be provided so as to be retained with the same fastener. In this case, an opening to pass the operative tool insertion entrance portion of the endoscope therethrough may be provided in the midportion of the fastener.

Furthermore, a finger hook protrusion may be provided protrudingly on the outer surface, or a finger hook protrusion may be provided protrudingly in the halfway portion of the outer surface, or a finger hook protrusion may be provided protrudingly on the edge portion of the outer surface.

Furthermore, the edge portion in the axial direction of the fastener may be formed into a shape expanding outward or the edge portion in the axial direction may be formed partly protrudingly into a shape of an ear. In addition, the fastener may be formed symmetrically, about the axial direction and a direction between which the axis is sandwiched.

With the embodiment of the present invention, a foul fluid absorbing member for absorbing foul fluids escaping from the operative tool insertion entrance can be readily attached to and detached from the outer wall portion of an endoscope. Thus, it is possible to prevent foul fluids within a body cavity from splashing from the operative tool insertion entrance during endoscopy, and the absorbing member can be quickly removed for cleaning or disposal upon the termination of endoscopy. Therefore, very sanitary endoscopy can be achieved.

Furthermore, even when a foul fluid absorbing member is inadvertently not mounted at the start of endoscopy, it is possible to always mount the foul fluid absorbing member with ease as necessary without extracting the inserting portion inserted into the body cavity. When the contamination of the foul fluid absorbing member reaches a certain level, it is possible to easily replace it with a new one.

As another embodiment of the present invention, a foul fluid splashing prevention device for an endoscope is provided, which is characterized in that a foul fluid absorbing member, formed from flexible, water-absorbing material, is detachably and attachably disposed on the endoscope so as to cover the upper and lower outer wall faces in the vicinity of the operative instrument insertion entrance of the endoscope. The foul fluid absorbing member is provided with a free end part that can be made to cover and uncover the operative instrument insertion entrance portion.

The foul fluid absorbing member may formed as two separate parts, one part for covering the upper wall face in the vicinity of the operative instrument insertion entrance of the endoscope and the other for covering the lower wall face in the vicinity of the operative instrument insertion entrance of the endoscope. The free end part is provided at one of said parts.

The foul fluid absorbing member may also be formed as one whole piece. The operative instrument insertion entrance portion may be formed as a protrusion that protrudes from the outer wall face. A hole through which this protrusion is passed may be formed in the foul fluid absorbing member.

Also, a separate retaining member may be provided for detachably and attachably retaining the foul fluid absorbing member to the outer wall face. This retaining member may be made from a resilient material and formed to have a cross sectional shape of a partially cut-out ring. The foul fluid absorbing member may be fixed to the outer wall face by pressing from the outer side.

With the embodiment of the present invention, foul fluids that escape from the operative instrument insertion entrance are first absorbed and prevented from splashing by a free end portion of a foul fluid absorbing member that covers the operative instrument insertion entrance portion. The fluids that splash or seep above the operative insertion entrance portion are absorbed by the upper portion of the foul fluid absorbing member. The foul fluids that tend to drip downward are absorbed by the lower portion of the foul fluid absorbing member. Foul fluids within the body cavity are thus prevented from splashing from the operative instrument insertion entrance and endoscopy can be performed in a sanitary manner.

As another embodiment of the present invention, a foul fluid splashing prevention device for an endoscope is provided, which is characterized in that a foul fluid absorbing member formed from water-absorbing material is positioned to face a forceps plug entrance. The forceps plug entrance is disposed at the entrance end portion of a forceps channel in such a manner that it is substantially closed and becomes open by an inserted operative instrument. The water absorbing material is disposed so that the operative instrument can be passed therethrough while being in close contact with the interior of the foul fluid absorbing member. The foul fluid absorbing member may be formed from continuously foamed material (open-shell material). Also, the forceps plugs and a retaining member for the foul fluid absorbing member may be detachably mounted with respect to each other, or the forceps lug and the retaining member for the foul fluid absorbing member may be provided as an integral unit.

The foul fluid absorbing member may be divided into and formed as a plurality of pieces so that the operative instrument to be inserted through the forceps plug is passed between the divided faces of the foul fluid absorbing member while spreading apart the divided faces, or the foul fluid absorbing member may be formed as a single block so that the operative instrument to be inserted into the forceps plug is passed through the foul fluid absorbing member while piercing through the foul fluid absorbing member.

With this embodiment of the present invention, since a foul fluid absorbing member formed from water-absorbing material is positioned to face the entrance of a forceps plug disposed at the entrance end portion of a forceps channel in such a manner that an operative instrument can be passed through the foul fluid absorbing member while being in close contact with the interior of the foul fluid absorbing member, foul fluids within the body cavity can be absorbed even when they escape out from the forceps plug and are thus prevented from splashing. Thus, endoscopy can be performed in a sanitary manner.

Another object of the present invention is to present a foul fluid splashing prevention device and/or a foul fluid splashing member fastener for an endoscope insertion guiding device that can significantly alleviate the contamination of the surroundings by feces when an endoscope is inserted into the large intestine from the anus. Thus, endoscopy can be performed in a sanitary manner.

To attain the above-noted and/or other objects, the present invention provides, in an embodiment, a foul fluid splashing prevention member fastener for an endoscope insertion guiding device. The fastener attachably and detachably retains a water-absorbing foul fluid absorbing member at the vicinity of the proximal portion of a flexible, pipe-like, endoscope insertion guiding device that is inserted from the anus into the colon to guide the inserted part of an endoscope. The fastener is made from resilient material and formed to have a horseshoe-like cross-sectional shape. The fastener is fixed by its own resilience in such a manner that it clamps the outer wall face of the insertion guiding device from the outer side while sandwiching the foul fluid absorbing member between itself and the outer wall face of the insertion guiding device.

The foul fluid absorbing material may be formed from a flexible material and may be a gauze-like member. Also, a protrusion that serves as a finger hook can protrude from the outer face, and this finger hook protrusion may protrude at an intermediate portion of the outer face or at an end portion of the outer face.

Furthermore, inwardly-directed protrusions for restricting the movement of the fastener in the axial direction of the insertion guiding device may be formed at the front and rear ends, or steps for restricting the movement of the fastener in the axial direction of the insertion guiding device may be formed at the insertion guiding device.

With the embodiment of the present invention, since a foul fluid absorbing member, for absorbing foul fluids that escape from the proximal portion of an insertion guiding device, can be readily attached to or detached from the insertion guiding device, foul fluids containing feces can be prevented from splashing from the proximal portion of the insertion guiding device during endoscopy, and the foul fluid absorbing member can be removed quickly for cleaning or disposal after the completion of endoscopy. Endoscopy can thus be performed in an extremely sanitary manner.

Furthermore, even if one forgets to attach the foul fluid absorbing member prior to endoscopy, the foul fluid absorbing member can be attached readily whenever necessary without having to draw out of the body the inserted part that has been inserted into the body cavity. The foul fluid absorbing member can be readily replaced with a new item when the contamination of the foul fluid absorbing member becomes severe during endoscopy.

In another embodiment of the present invention, a flexible, pipe-like, endoscope insertion guiding device is provided, which is inserted from the anus into the colon to guide the inserted part of an endoscope. The endoscope insertion guiding device is arranged such that a foul fluid absorbing member, with water-absorbing properties for absorbing foul fluids that escape from the root portion at the proximal side, is mounted in a detachable and attachable manner near the proximal portion.

The foul fluid absorbing member may be formed from flexible material and may be retained onto the outer peripheral surface of the proximal portion. The foul fluid absorbing member may be a gauze-like member.

The foul fluid absorbing member may also be fixed to the outer peripheral surface of the proximal portion by compression from the outer side by a resilient retaining member. This retaining member may be shaped to have a C-like, U-like, or laid-down U-like cross sectional shape.

With the embodiment of the present invention, since a foul fluid absorbing member, provided with water-absorbing properties for absorbing foul fluids that escape from the root portion at the proximal side, is detachably attached to a portion of an insertion guiding device near the proximal portion, the contamination of the surroundings by feces can be alleviated significantly during endoscopy in which an endoscope is inserted into the large intestine from the anus.

The present disclosure relates to subject matter contained in Japanese paten application Nos:

8-223878 (filed on Aug. 26, 1996);
8-223879 (filed on Aug. 26, 1996);
8-223880 (filed on Aug. 26, 1996);
8-260368 (filed on Oct. 1, 1996);
8-260369 (filed on Oct. 1, 1996);

9-029913 (filed on Feb. 14, 1997);
9-029914 (filed on Feb. 14, 1997);
9-040192 (filed on Feb. 25, 1997);
9-041723 (filed on Feb. 14, 1997); and
9-177893 (filed on Jul. 3, 1997),
which are expressly incorporated herein by reference in their entireties.

DETAILED DESCRIPTION OF THE PREFERRED EMBODIMENTS

Embodiments of the present invention will now be described with reference to the drawings.

Figure 1:
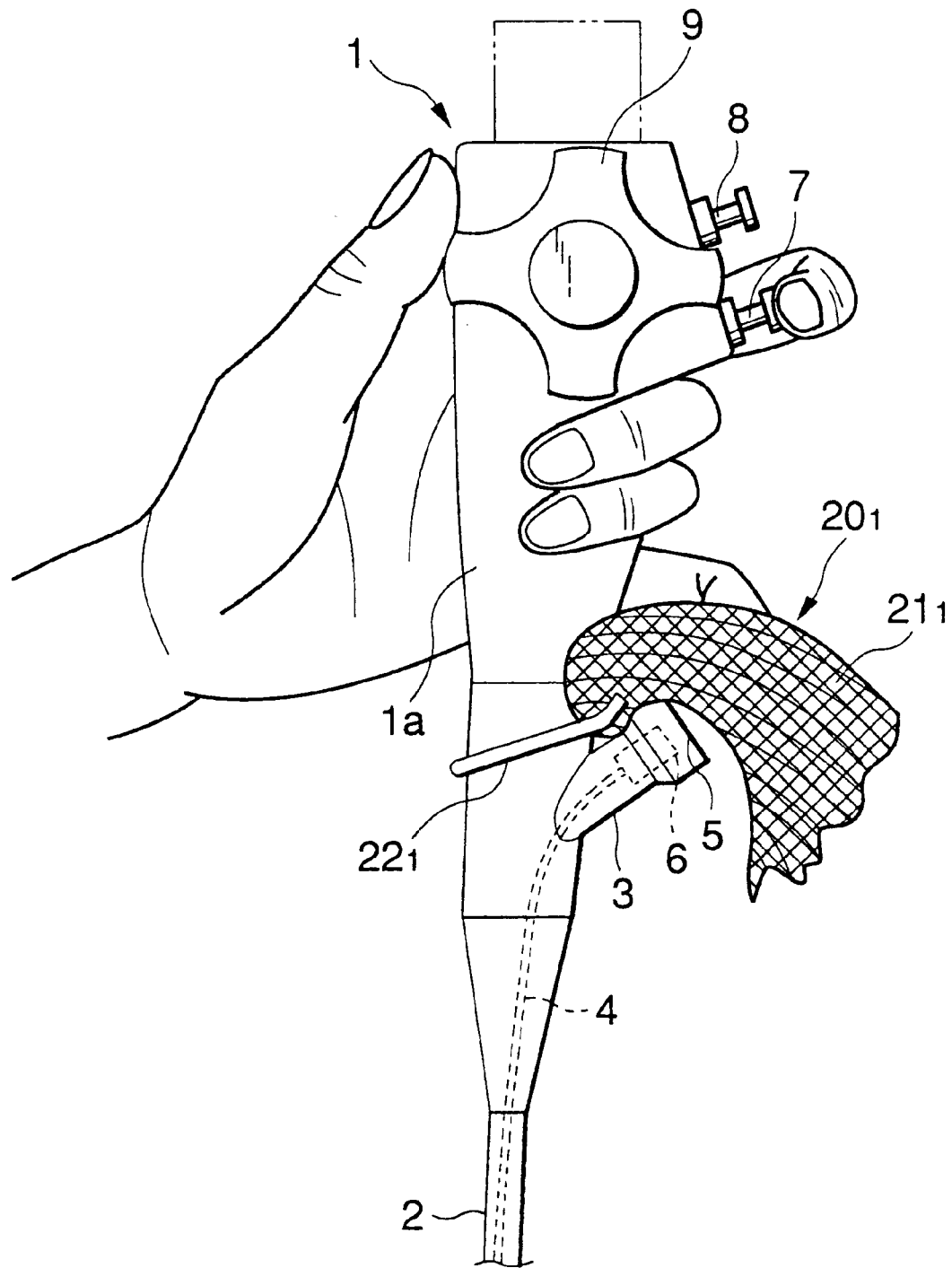
FIG. 1 is a side view which shows the condition in which a foul fluid splashing prevention device of a first embodiment of the present invention is attached to the manipulating part.

In FIG. 1, reference numeral 1 designates a manipulating part of an endoscope, and an inserted part 2, which is to be inserted into the body cavity, is connected to the lower end portion of this manipulating part 1.

A forceps channel 4, which opens out at the front end, is passes through the entire length of inserted part 2. The base end side of the forceps channel 4 is in communication with an operative instrument insertion entrance 5, which is opened at the tip of a protrusion 3 protruded obliquely upwards from the lower end portion of the manipulating part 1.

Inside protrusion 3, a forceps plug 6 is disposed adjacent to the inner side of the operative instrument insertion entrance 5, which is generally closed by forced to open by insertion of an operative instrument into forceps channel 4 from the operative tool insertion entrance 5.

At the upper half portion of manipulating part 1, an air/water conveying control valve 7 and a suction control valve 8 are disposed at the front face side and a curvature manipulating knob 9, for remote manipulation of the bending of a curved part (not shown) formed near the front end of inserted part 2, is disposed at the side face. A grip part 1$a$ is formed between this portion and the lower end portion of manipulating part 1.

Although an air conveying tube and a water conveying tube, that are opened at the front end of the inserted part 2, are connected in communication with the air/water conveying control valve 7, these tubes are not illustrated.

Also, the suction control valve 8 is connected in communication with the forceps channel 4 at the lower end portion of the manipulating part 1 with forceps channel 4 serving in common as a suction channel.

Figure 2:
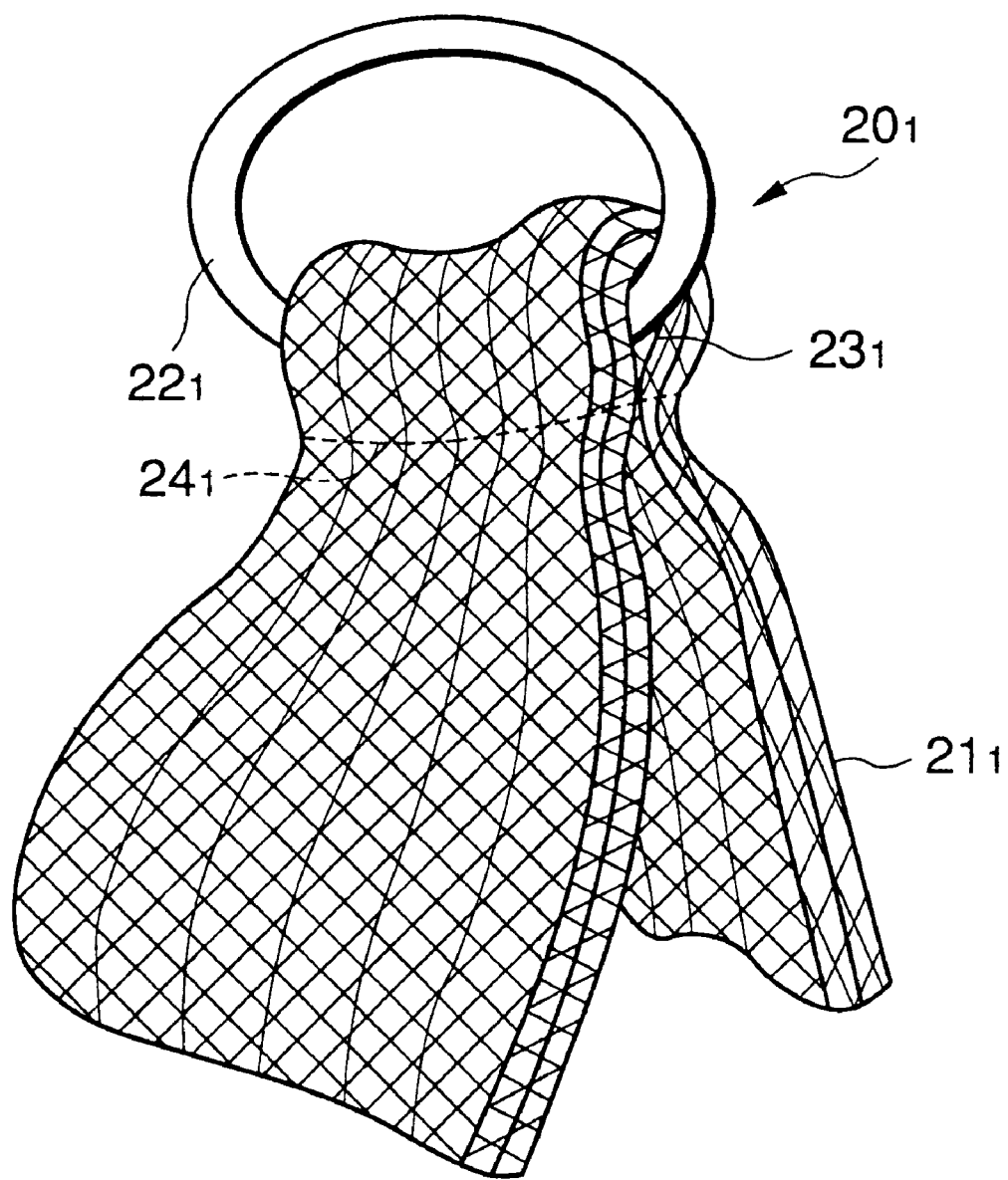
FIG. 2 is a perspective view of the foul fluid splashing prevention device of the first embodiment of the present invention.

Reference numeral $20_1$ designates a foul fluid splashing prevention device for an endoscope. As shown in FIG. 2, a plurality of sheets of water absorbing material, for example flexible gauze, are overlapped and folded over to form a foul fluid absorbing member $21_1$, and a retaining member $22_1$, made for example from a rubber band, etc. is engages with the folded-over part of the absorbing member $21_1$.

In this embodiment, foul fluid absorbing member $21_1$ is sewn parallel to the fold line near the folded part to form a pass-through hole $23_1$ for letting the retaining member $22_1$ pass therethrough. The reference numeral $24_1$ designates the seam.

Although the foul fluid absorbing member $21_1$ may simply be folded instead of forming such a pass-through hole $23_1$, the pass-through hole $23_1$ eases the attachment/detachment, etc. of the preventive member $20_1$ to the manipulating part 1 since the retaining member $22_1$ is attached in a stable manner to the foul fluid absorbing member $21_1$.

The foul fluid splashing prevention device $20_1$ thus constructed is fixed by passing the inserted part 2 of the endoscope through the retaining member $22_1$ and binding to a lower end portion of manipulating part 1 by means of the retaining member $22_1$ as shown in FIG. 1. The diameter of the retaining member $22_1$ is set according t the thickness of the manipulating part 1.

In this embodiment, the retaining member $22_1$ is fixed at a portion above the protrusion 3 so that the foul fluid absorbing member 21 covers the outer surface of the operative instrument insertion entrance 5 from the upper side.

In this condition, the foul fluid absorbing member $21_1$ can be held by being lightly pressed by the small finger of the operator's hand that grips the grip part 1$a$ as shown in FIG. 1, and even if foul fluids in the body cavity passing through forceps channel 4 escapes outward from the operative instrument insertion entrance 5, the fluids can be absorbed by the foul fluid absorbing member $21_1$ and can not splash about or get on the hands or face of the operator.

Figure 3:
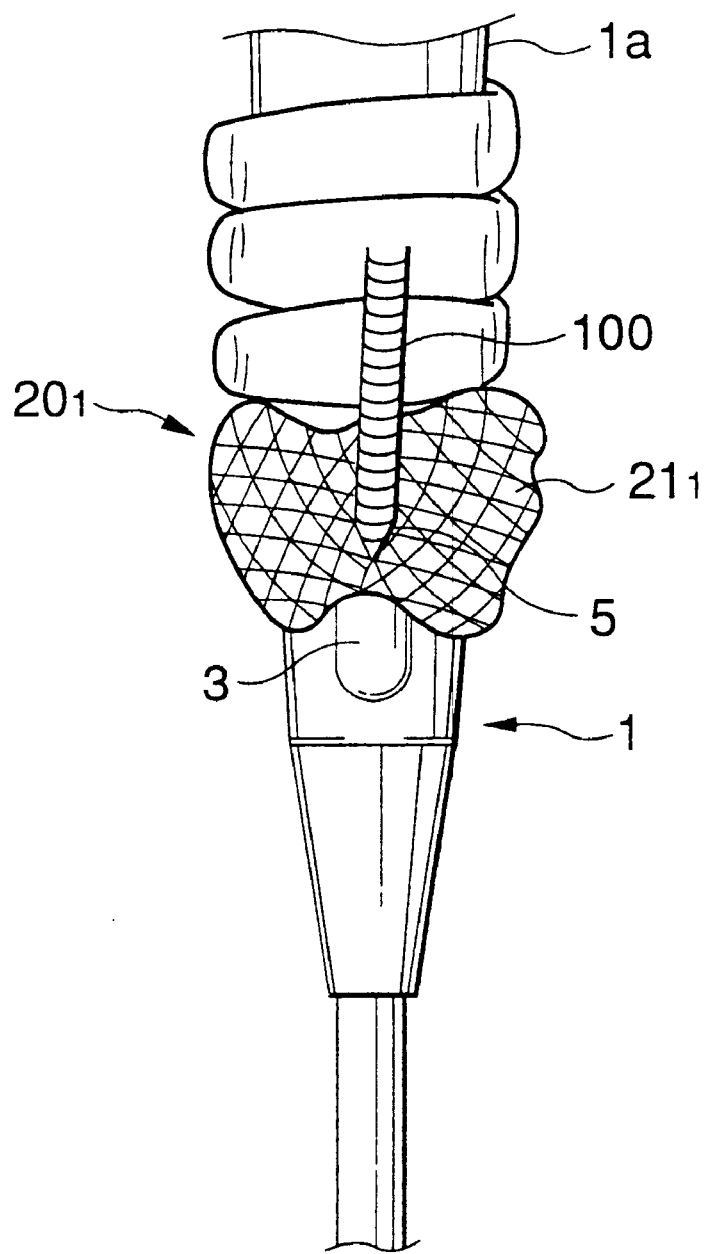
FIG. 3 is a partial front view which shows the condition in which an operative instrument is used with the foul fluid splashing prevention device of the first embodiment of the present invention being attached to the manipulating part.

In the case when an operative instrument is used, upon inserting it through the forceps channel 4 from the operative instrument insertion entrance 5, the splashing of foul fluid can be prevented by surrounding the periphery of the operative instrument 100% with the foul fluid absorbing member $21_1$ as shown in FIG. 3.

Figure 4:
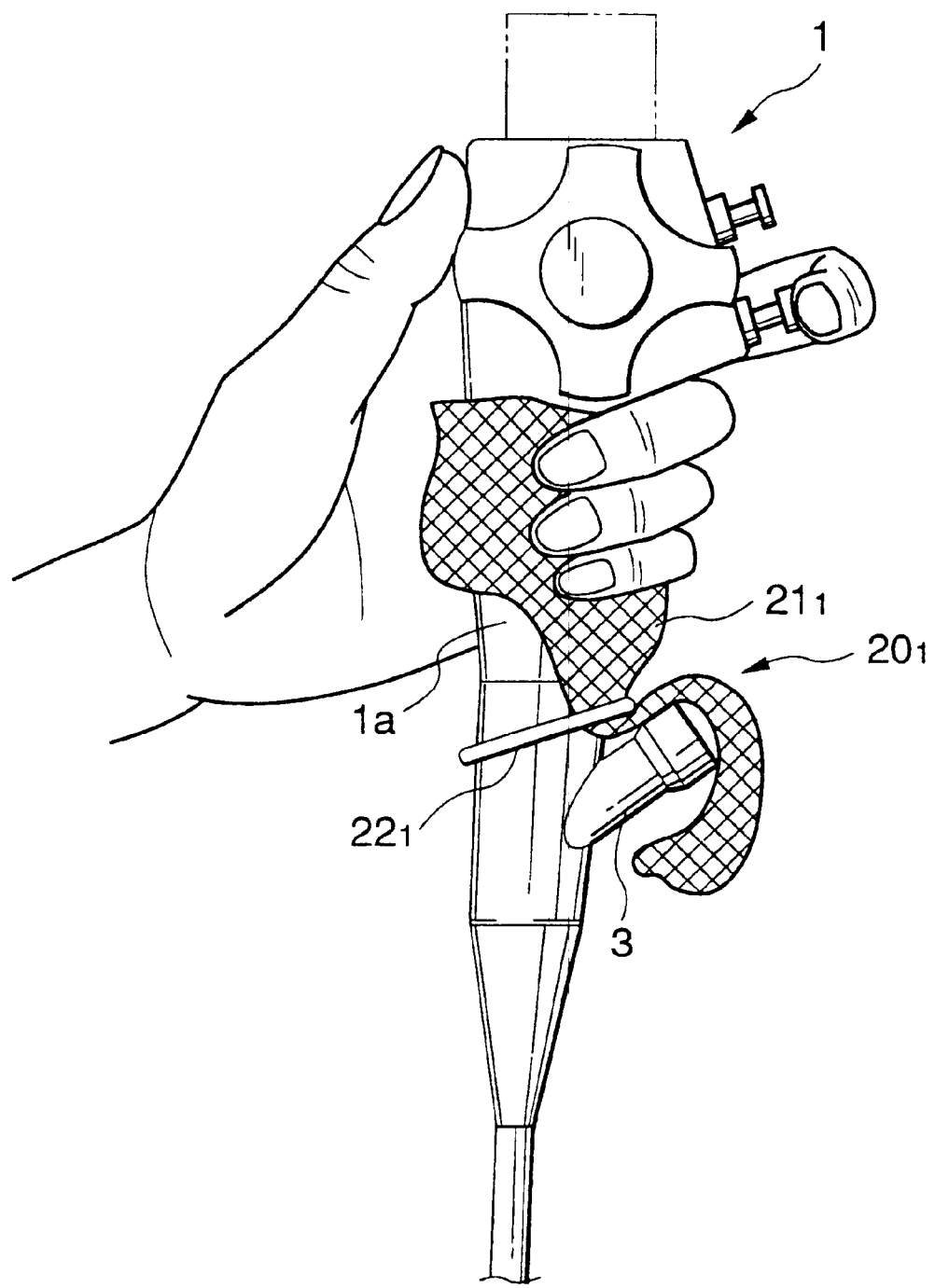
FIG. 4 is a side view which shows a different condition of use of the foul fluid splashing prevention device of the first embodiment of the present invention.

Also, by covering the grip part 1$a$ of the manipulating part 1 using a half of the foul fluid absorbing member $21_1$ and grasping the foul fluid absorbing member $21_1$ with the hand that holds grip part 1$a$ as shown in FIG. 4, the foul fluids can be prevented from flowing to the hand, the manipulating part 1 can be held securely without slippage, and foul fluid absorbing member $21_1$ can be held in a stable manner.

Figure 5:
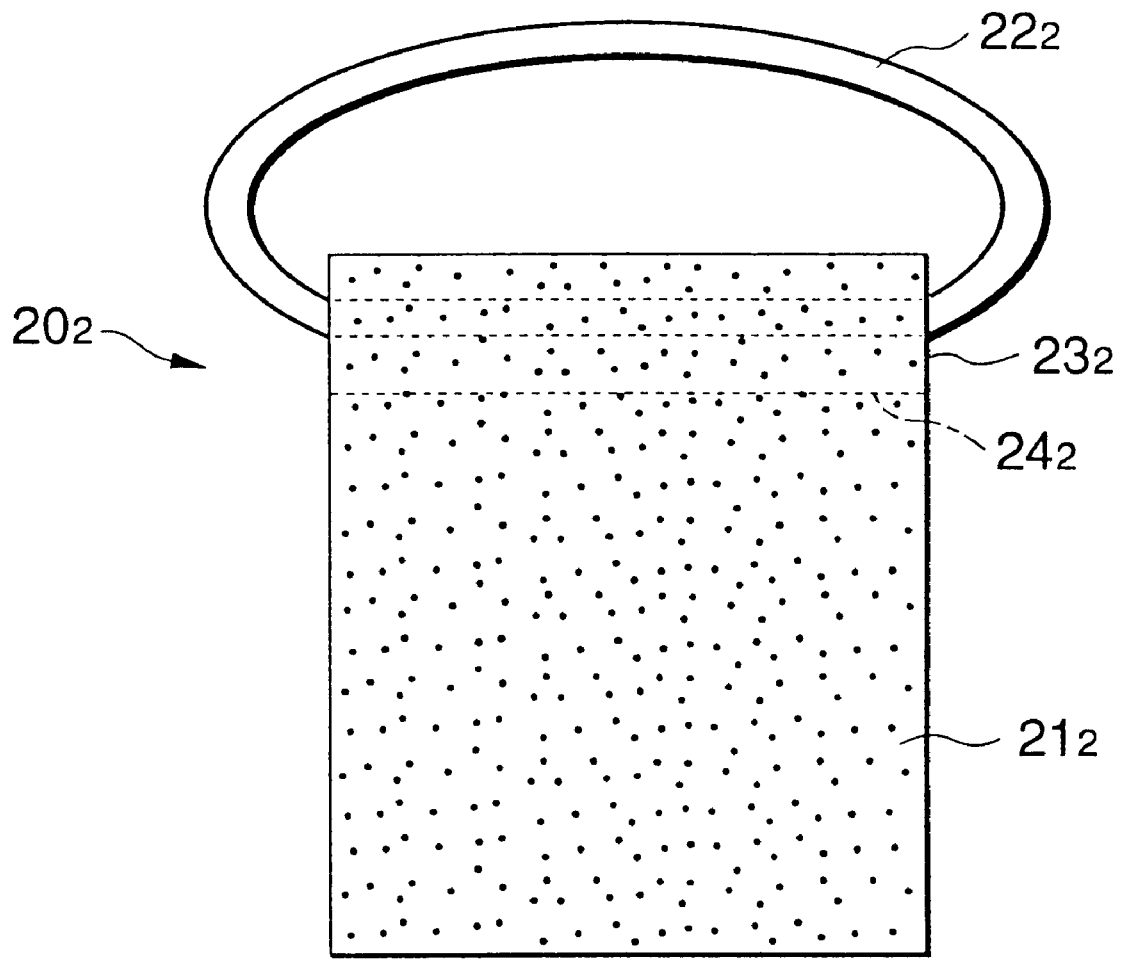
FIG. 5 is a front view of a foul fluid splashing prevention device of a second embodiment of the present invention.

As shown in FIG. 5, the material of the foul fluid absorbing member is not limited to a gauze and a wide variety of flexible, water-absorbing materials, such as sponge, open-cell material, water-impregnable non-woven fabric, high molecular with water-impregnable polymer, etc., can be used in place of the seam ($21_2$, FIG. 5). Also, a solvent weld, etc. can be used in place of the seam ($24_2$) portion for forming the pass-through hole $23_2$.

Figure 6:
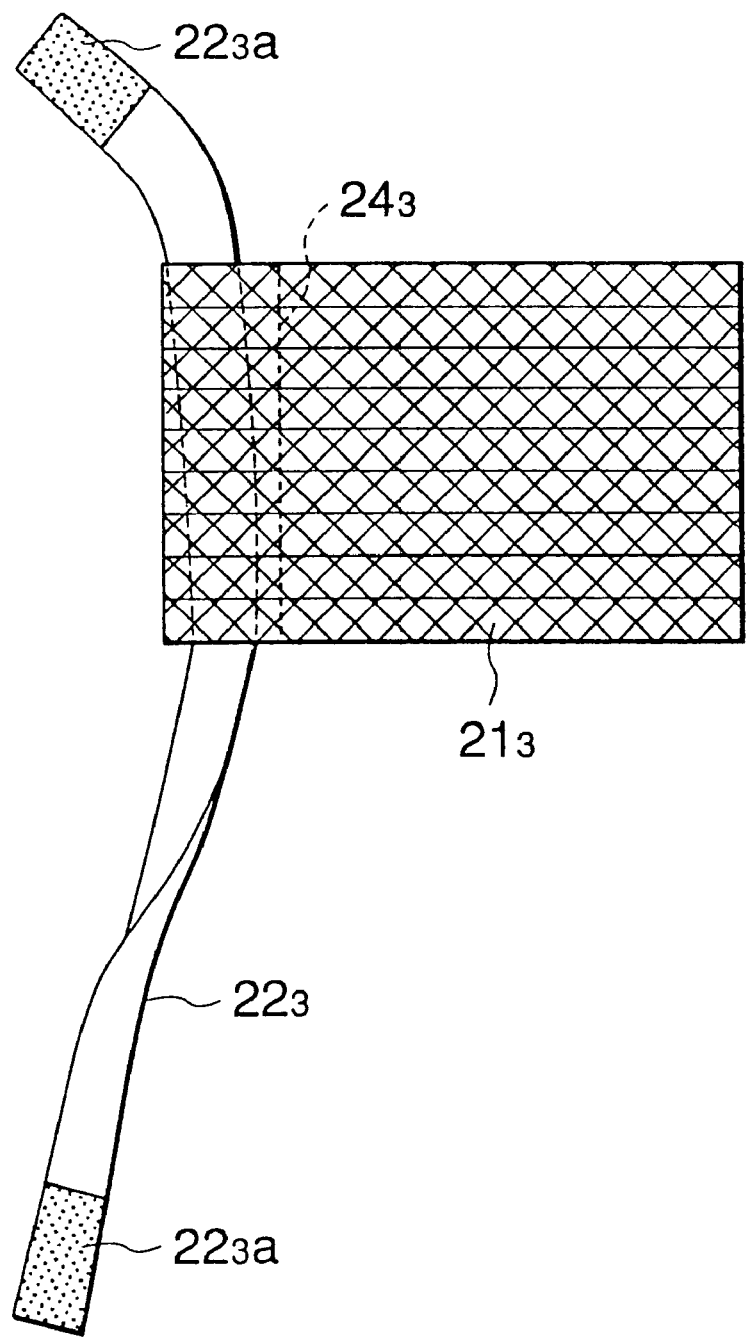
FIG. 6 is a front view of a foul fluid splashing prevention device of a third embodiment of the present invention.

Also, an end-to-end cord-like member $22_3$ can be used for the retaining member for example as shown in FIG. 6. A Swedish fastener or hook-and-loop fastener (so-called VELCRO tape) $22_3a$, etc. can be provided at both ends so that the end portions can be engaged with each other.

Figure 7:
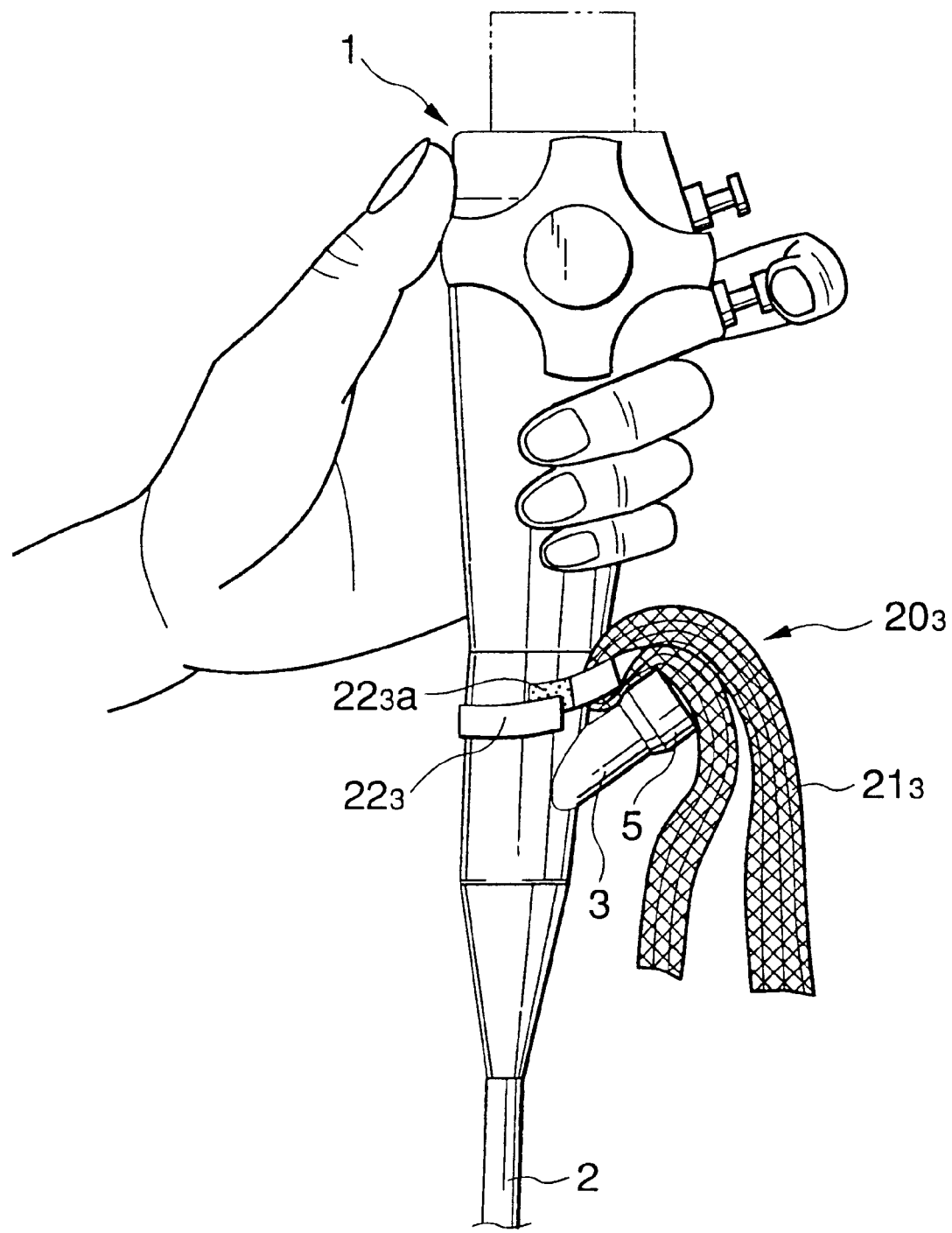
FIG. 7 is a side view which shows the condition in which the foul fluid splashing prevention device of the third embodiment of the present invention is attached to the manipulating part.
Figure 8:
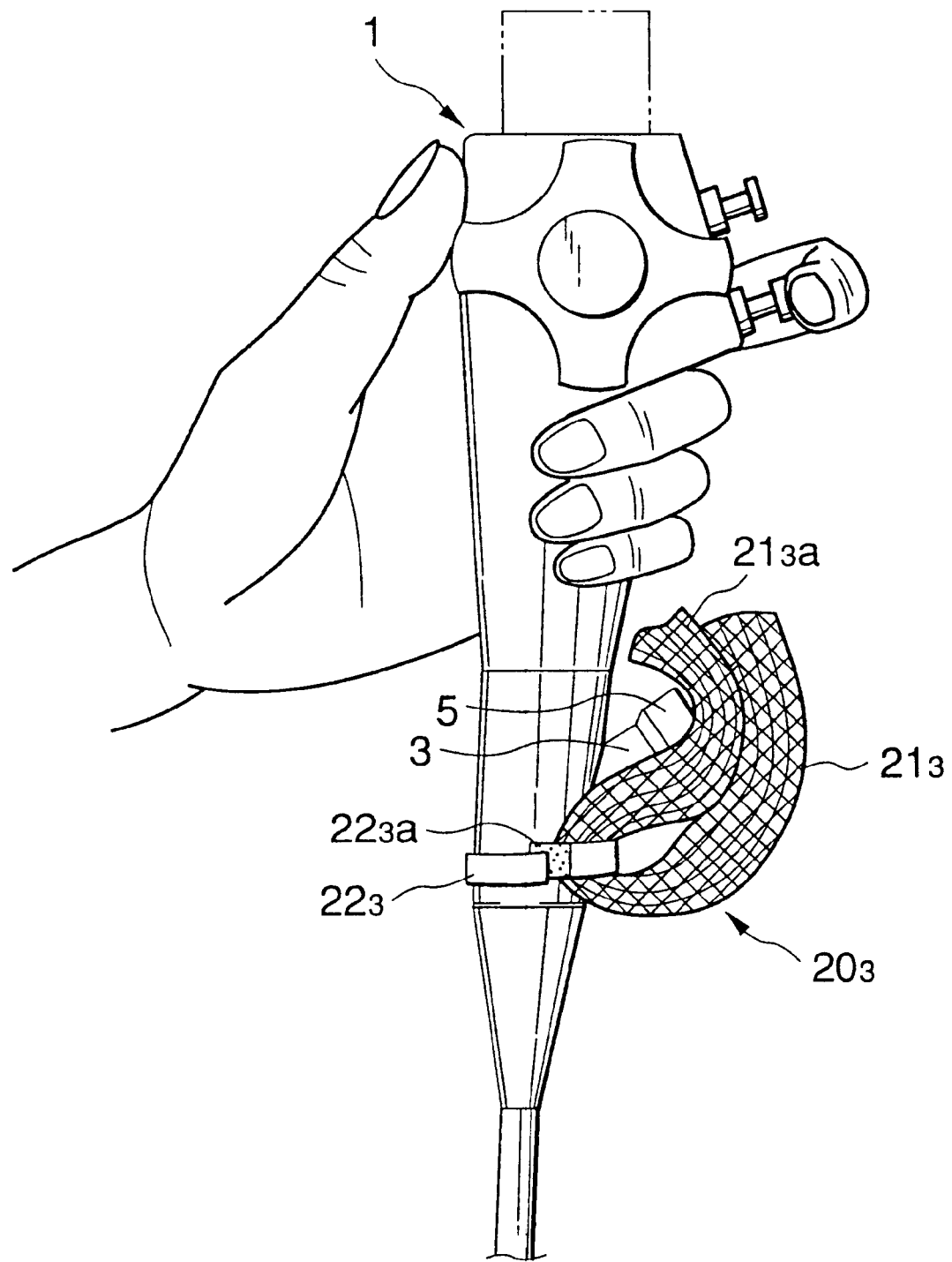
FIG. 8 is a side view which shows the condition in which the foul fluid splashing prevention device of the third embodiment of the present invention is attached to the manipulating part in a different manner.

FIG. 7 shows the condition when the embodiment shown in FIG. 6 is used, and with this embodiment, the detachment and attachment of the preventive device $20_3$ to the manipulating part 1 can be performed more readily in comparison to the case where a rubber band is used. Also, as shown in FIG. 8, the retaining member $22_3$ can be fixed to the manipulating part 1 at a position below the protrusion 3 so that the absorbing member covers the outer surface of the operative instrument insertion entrance 5 from the lower side.

In this case, since the end portion $21_3a$ of the foul fluid absorbing member $21_3$ is lowered by gravity to a position where it covers the surface of operative instrument insertion entrance 5, the splashing of foul fluid from the operative instrument insertion entrance 5 can be prevented.

Figure 9:
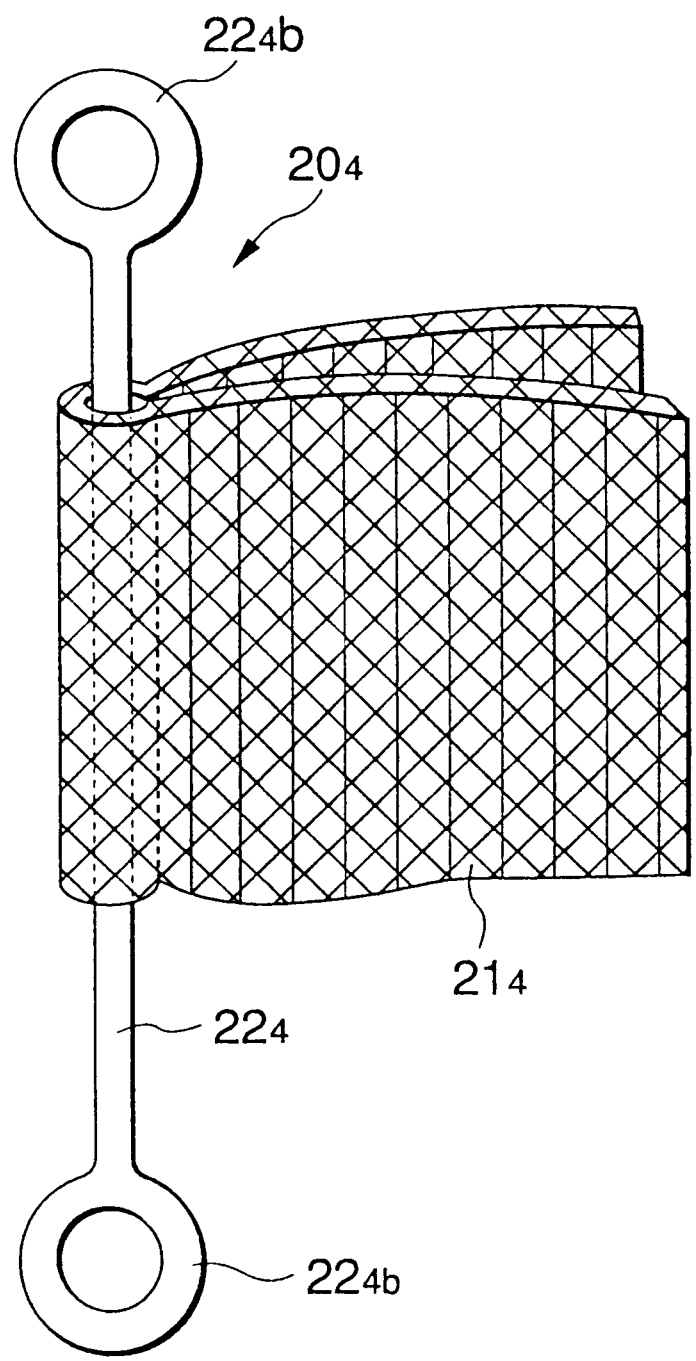
FIG. 9 is a perspective view of a foul fluid splashing prevention device of a fourth embodiment of the present invention.
Figure 10:
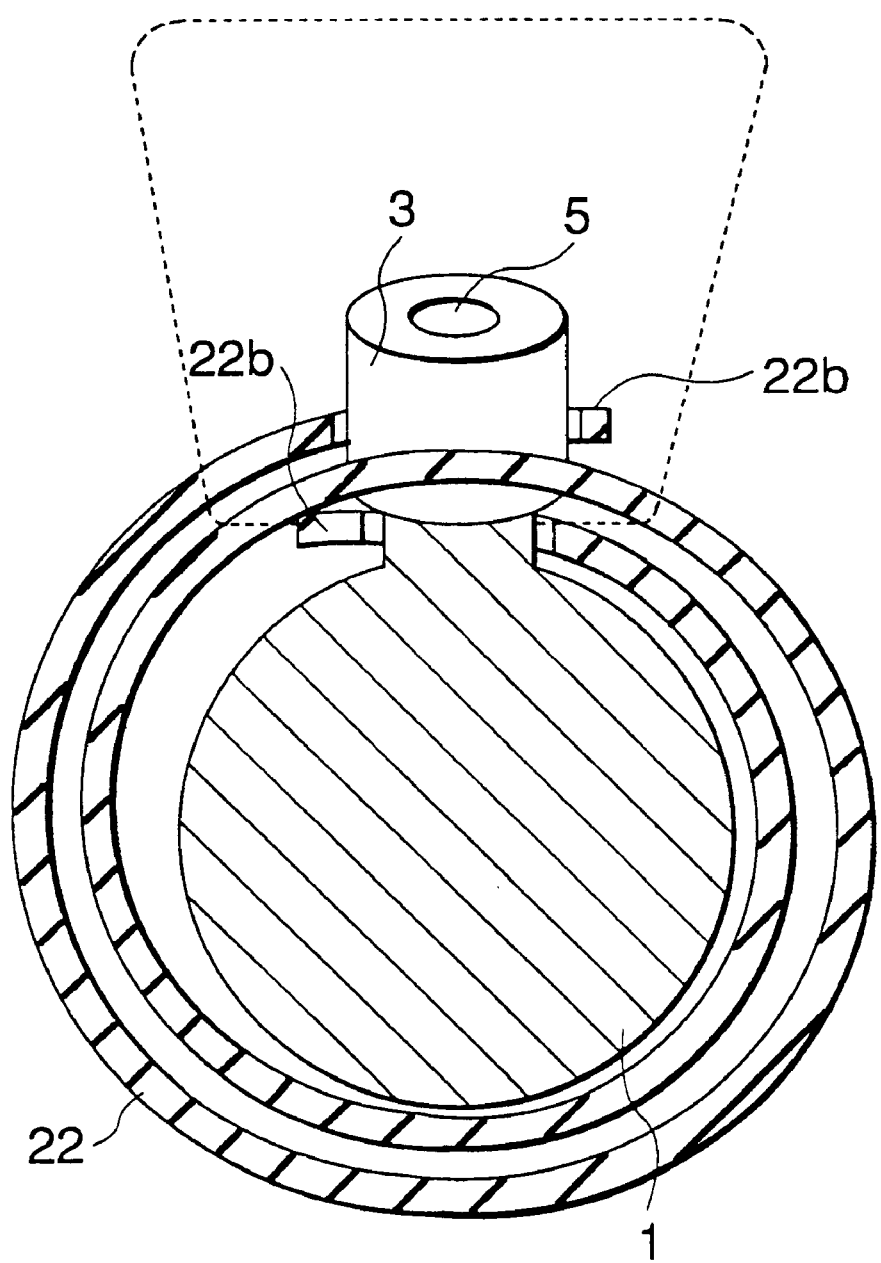
FIG. 10 is a schematic sectional plan view which shows the condition in which the foul fluid splashing prevention device of the fourth embodiment of the present invention is attached to the manipulating part.

FIGS. 9 and 10 illustrate an embodiment in which retaining rings $22_4b$ are formed at the ends of the retaining member $22_4$, and the retaining rings $22_4b$ at both ends are hooked and retained on the protrusion 3 under the condition that the retaining member $22_4$ is wound around the lower end portion of the operating part 1. The attachment and detachment of foul fluid splashing prevention device $20_4$ to and from manipulating part 1 is thus facilitated. It is preferable to use a resilient material for the retaining member $22_4$.

Figure 11:
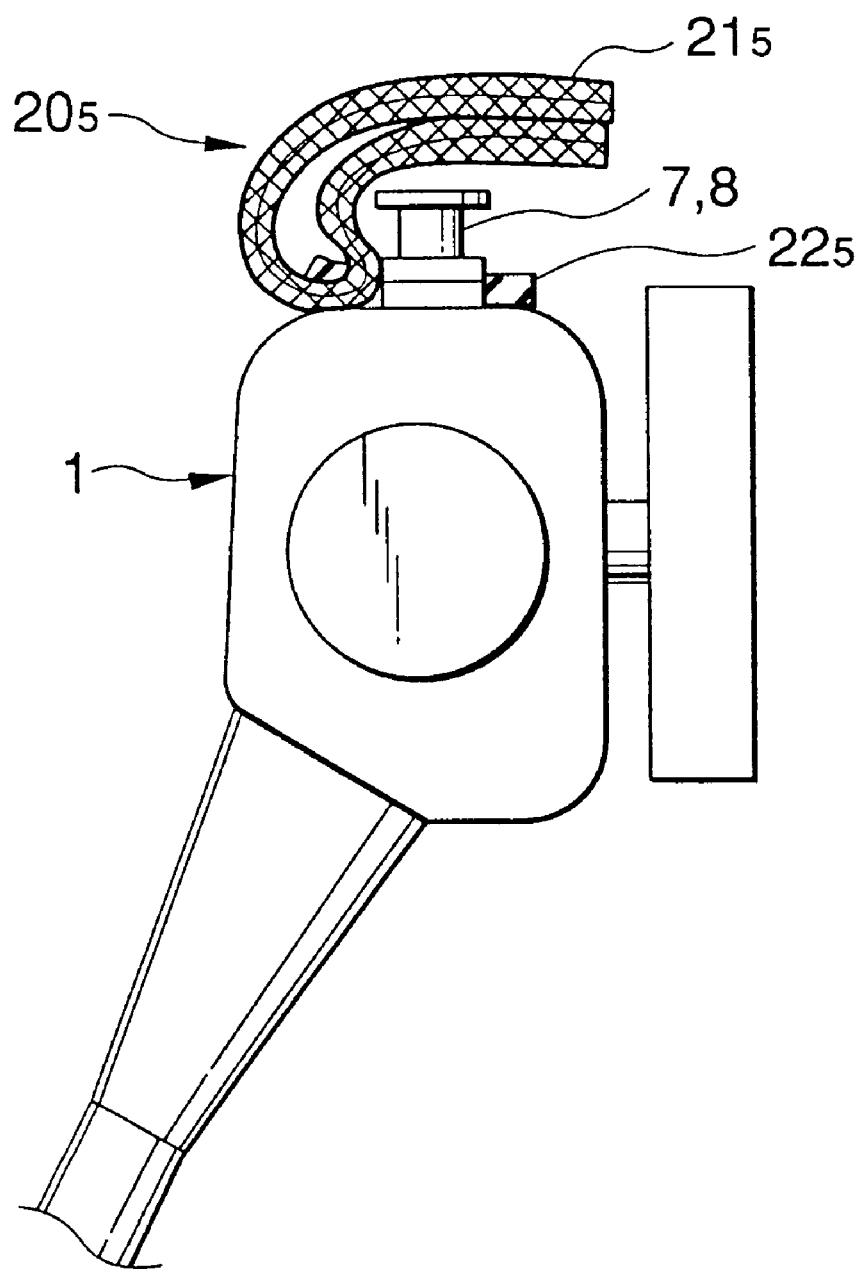
FIG. 11 is a plan view partly in section which shows the condition in which a foul fluid splashing prevention device of a fifth embodiment of the present invention is attached to the manipulating part.
Figure 12:
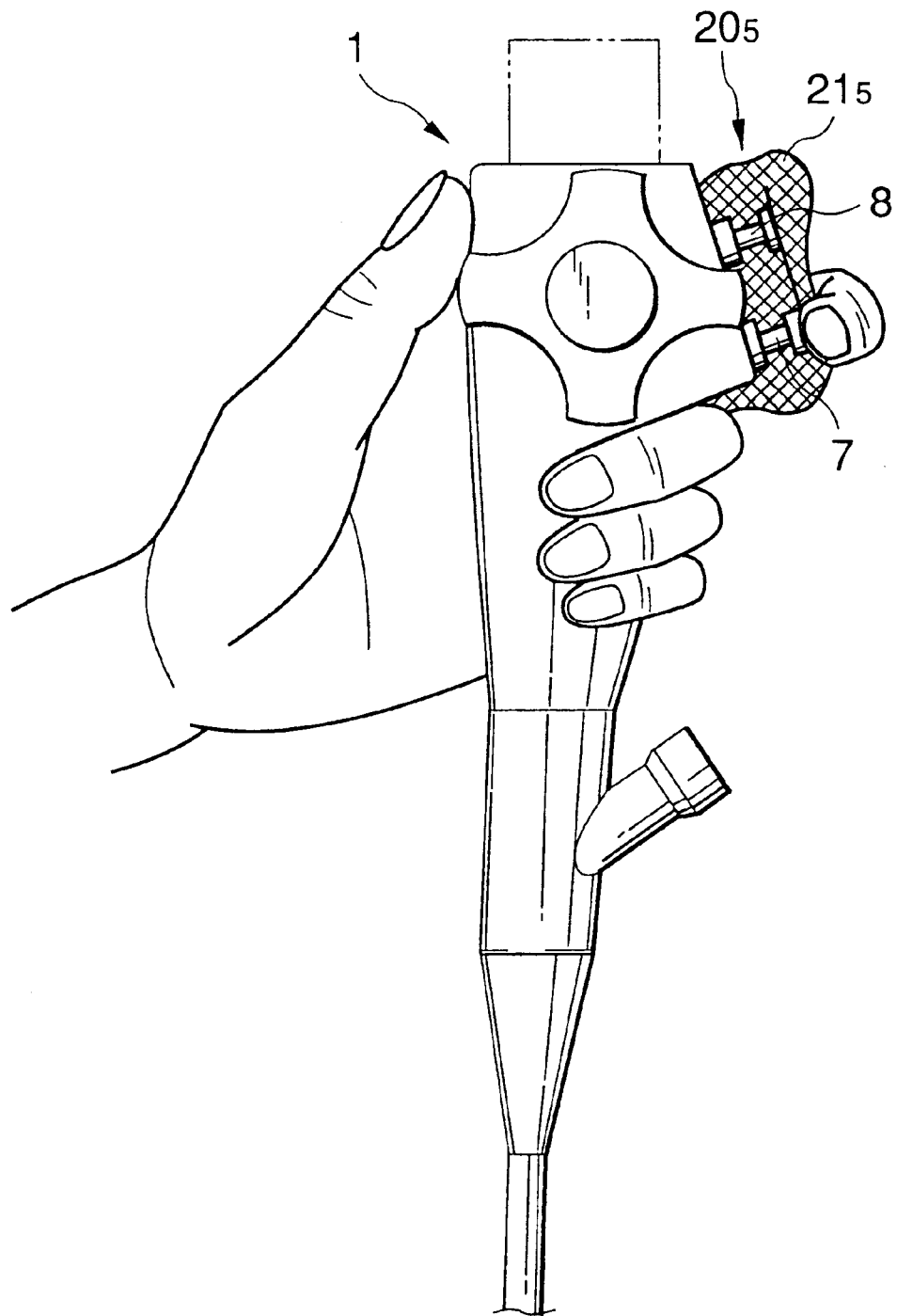
FIG. 12 is a side view which shows the condition in which a foul fluid splashing prevention device of a fifth embodiment of the present invention is attached to the manipulating part.

FIGS. 11 and 12 illustrate an embodiment in which foul fluid splashing prevention device $20_5$ is attached to the upper half portion of the manipulating part 1 so that the outer surfaces of the air/water conveying control valve 7 and the suction control valve 8 are covered with the foul fluid absorbing member $21_5$.

In this case, the foul fluid that splashes from the leak port, etc., formed on the air/water conveying control valve 7 or suction control valve 8, can be absorbed even when the O-rings fitted to valves 7 and 8 become damaged, etc.

FIGS. 13 to 16 illustrate an embodiment in which a pressure-sensitive adhesive material is used as the retaining member. Similar to the former embodiments, a foul fluid absorbing member $21_6$ is formed by folding over and overlapping a plurality of sheets of the water-absorbing material, such as flexible gauze, etc. The central portion of the foul fluid absorbing member $21_6$ is sewn with thread to prevent it from spreading.

Figure 15:
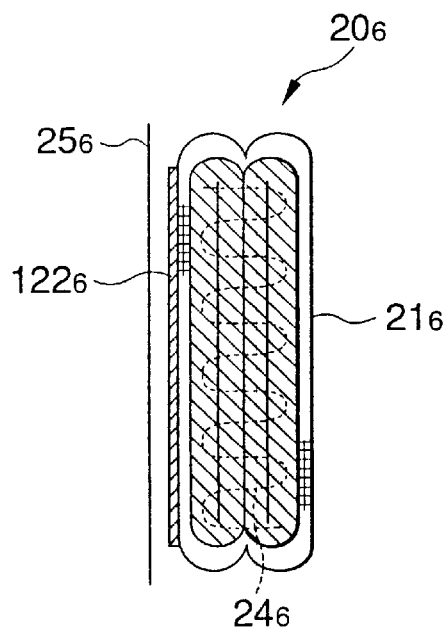
FIG. 15 is a cross section along line 15—15 in FIG. 14 of the foul fluid splashing prevention device of the sixth embodiment of the present invention.

As illustrated in FIG. 15, which shows a cross section along the thread ($24_6$) portion, a retaining member $122_6$, which is for retaining the foul fluid splashing prevention device $20_6$ to the manipulating part 1 and is formed from a pressure-sensitive adhesive material, such as a double-coated adhesive tape, is adhered onto the surface of the foul fluid absorbing member $21_6$ along the portion sewn by thread $24_6$.

As shown in FIG. 15, a protective sheet $25_6$, which can be readily peeled off from double-coated adhesive tape $122_6$, is attached to the surface of the adhesive tape $122_6$ at the side which is to be adhered onto the manipulating part 1. This protective sheet $25_6$ is to be peeled off immediately prior to attaching the adhesive tape $122_6$ onto the manipulating part 1.

Figure 13:
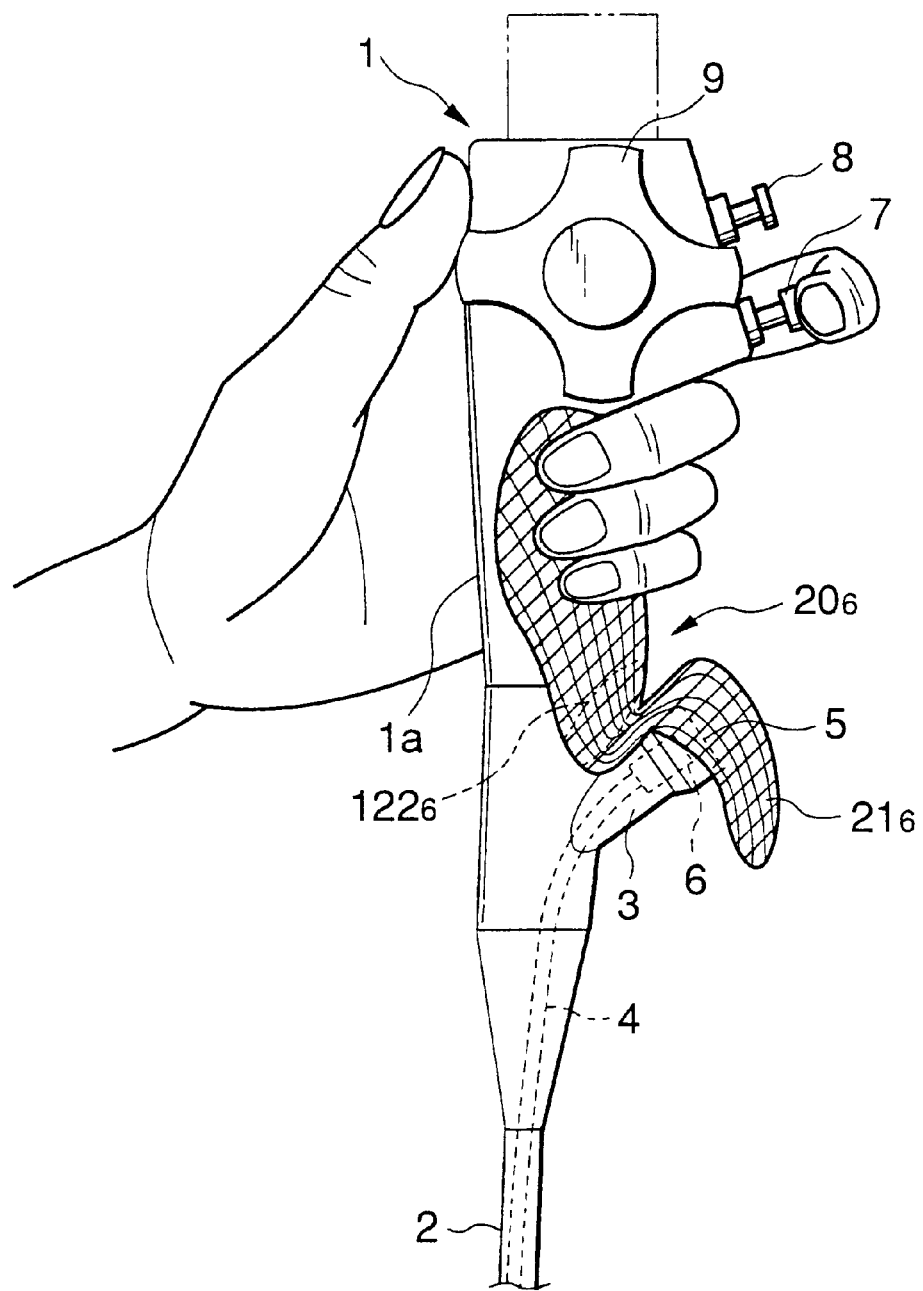
FIG. 13 is a side view which shows the usage condition in which a foul fluid splashing prevention device of a sixth embodiment of the present invention is attached to the manipulating part.
Figure 14:
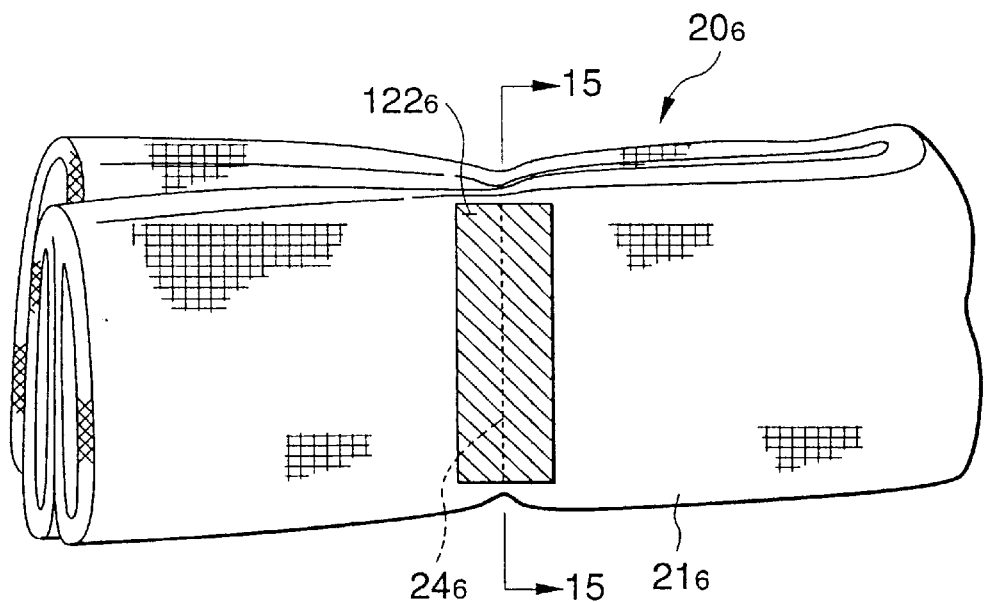
FIG. 14 is a perspective view of the foul fluid splashing prevention device of a sixth embodiment of the present invention.

In use, the protective sheet $25_6$ is removed, and the retaining member $122_6$, is then adhered onto the front outer surface immediately above the protrusion 3 of the manipulating part 1 so that the operative instrument insertion entrance (5) portion is covered with a half of the foul fluid absorbing member $21_6$ as shown in FIG. 13.

Figure 16:
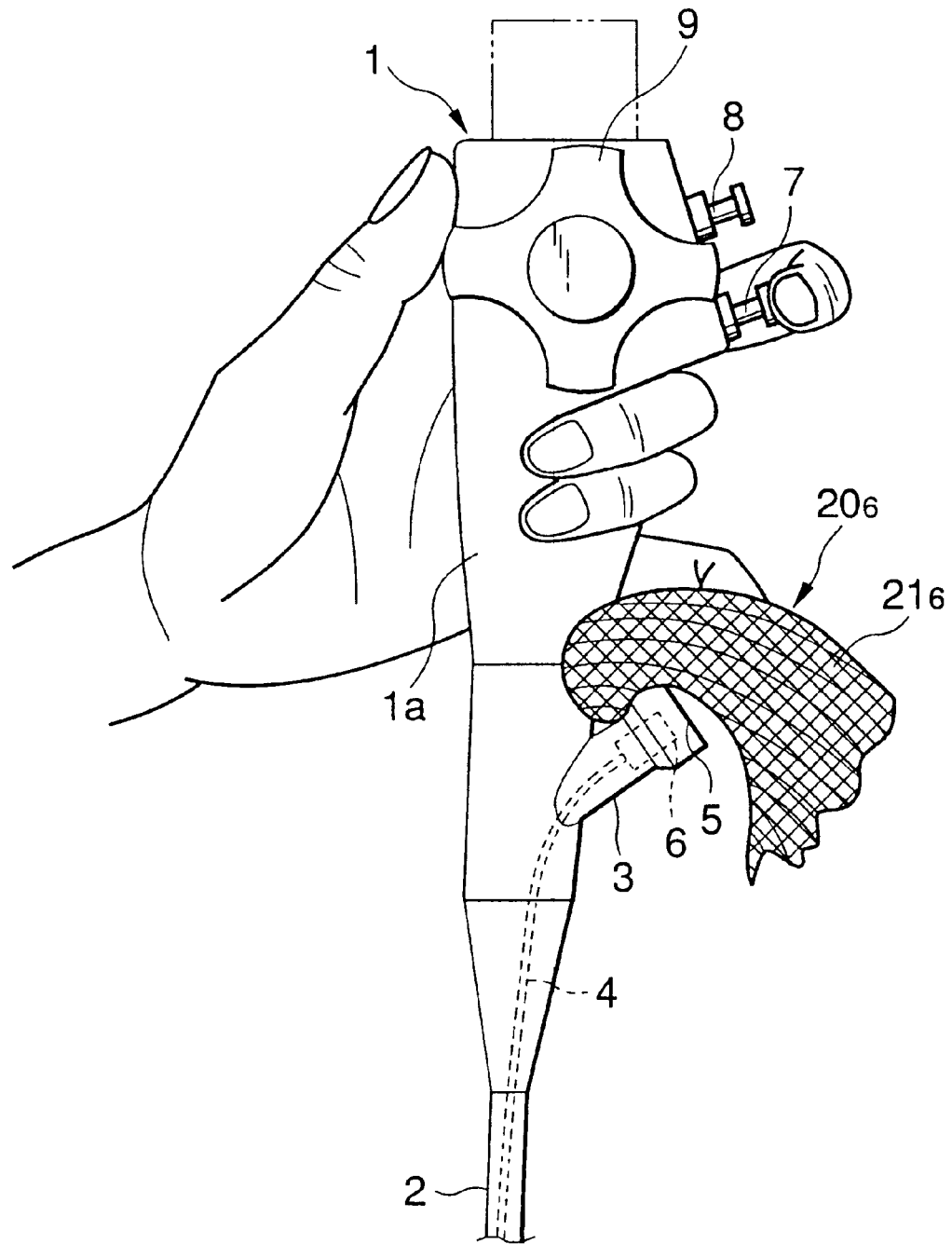
FIG. 16 is a side view which shows a different usage condition in which the foul fluid splashing prevention device of the sixth embodiment of the present invention is attached to the manipulating part.

As shown in FIG. 16, the foul fluid absorbing member $21_6$ may be positioned so that the halves at both sides can cover the operative instrument insertion entrance 5. In this case, the foul fluid absorbing member $21_6$ can be held by being lightly pressed by the small finger of the operator's hand that grips grip part 1a, so that the absorption of foul fluids that leak out from the operative instrument insertion entrance 5 can be enhanced.

Figure 17:
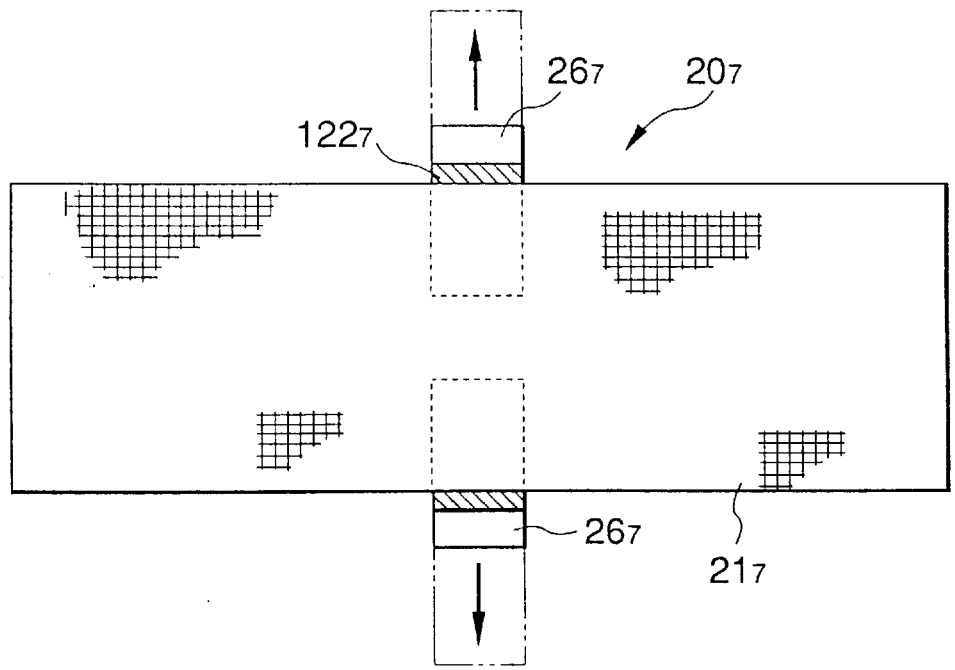
FIG. 17 is a front view of a foul fluid splashing prevention device of a seventh embodiment of the present invention.
Figure 18:
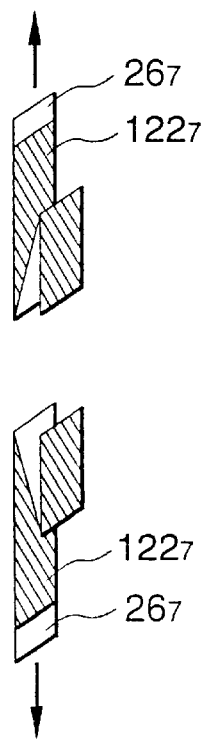
FIG. 18 is a perspective view of the retaining member of the foul fluid splashing prevention device of the seventh embodiment of the present invention.

FIGS. 17 and 18 show another embodiment of the present invention in which a single-coated adhesive tape is used as the retaining member. The retaining member $122_7$ of this embodiment is folded as shown in FIG. 18 in the condition prior to use.

Figure 19:
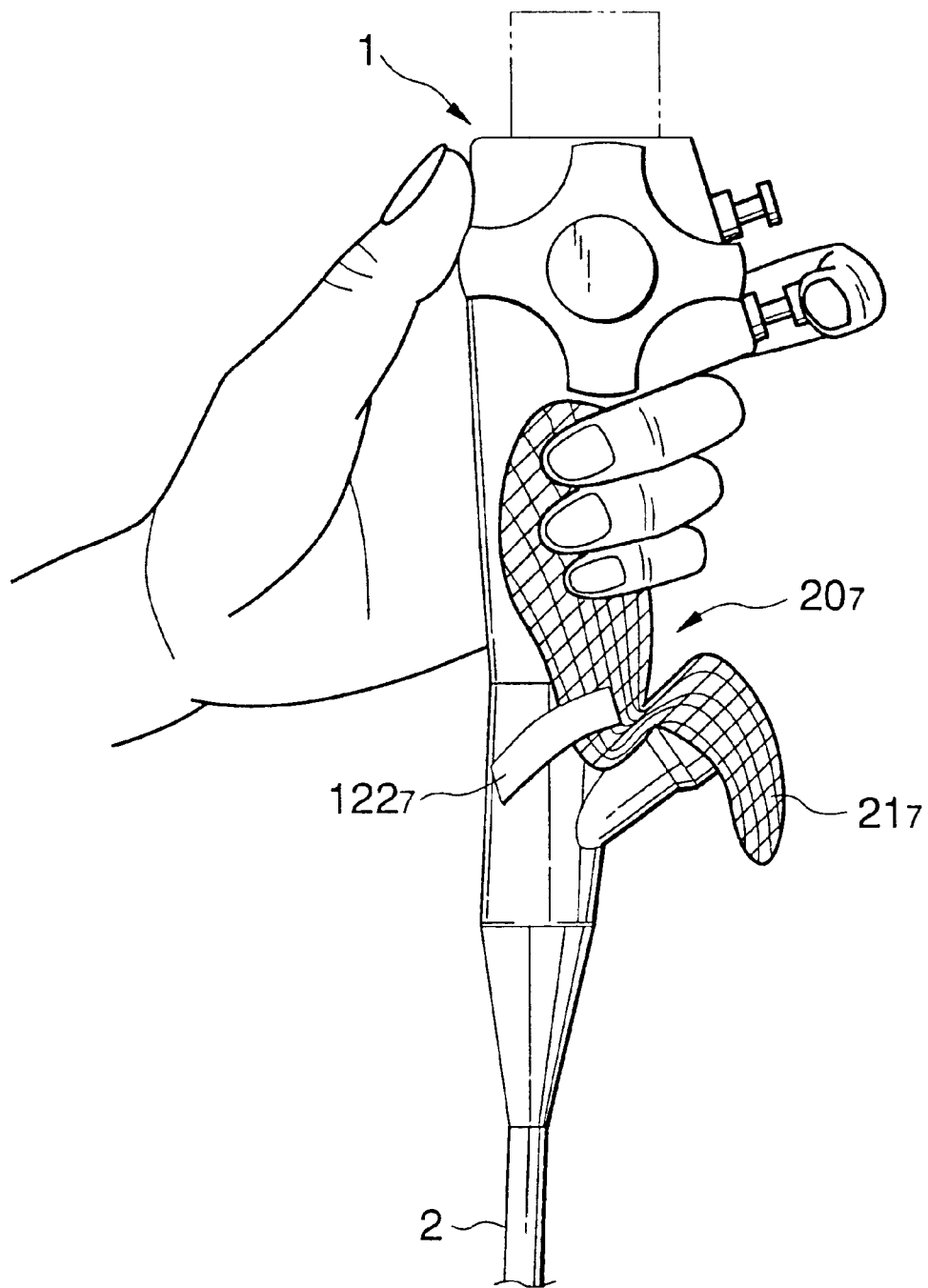
FIG. 19 is a side view which shows the usage condition in which the foul fluid splashing prevention device of the seventh embodiment of the present invention is attached to the manipulating part.

In use, the non-adhesive tab part $26_7$ formed at the tip is pulled outward to draw out the retaining member $122_7$ so that it can be adhered onto the outer surface of the manipulating part 1 as shown in FIG. 19.

Although a half of the foul fluid absorbing member $21_7$ is set along and held together with the grip part 1a of the manipulating part 1 in FIG. 19, the operative instrument insertion entrance 5 may, of course, be covered with the halves of the foul fluid absorbing member $21_7$ at both sides.

Figure 20:
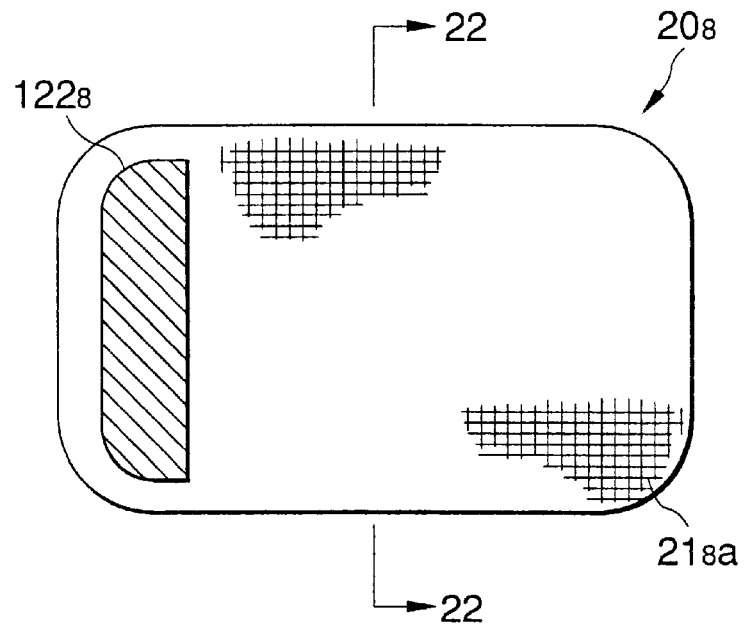
FIG. 20 is a front view of a foul fluid splashing prevention device of an eighth embodiment of the present invention.
Figure 21:
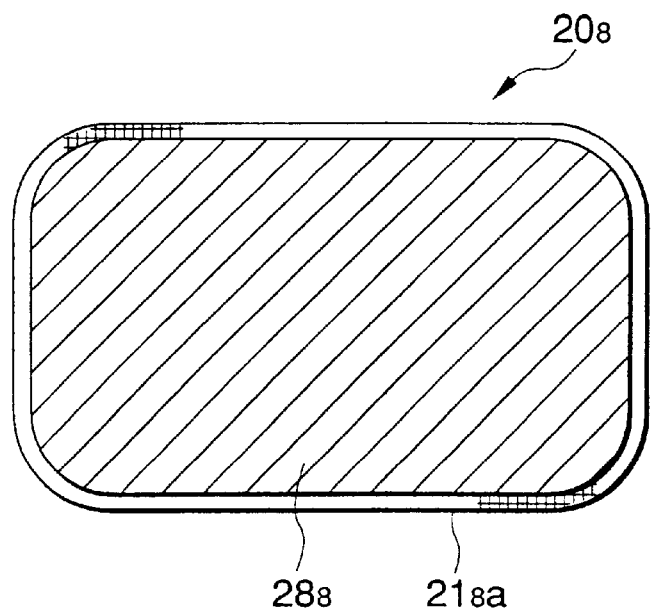
FIG. 21 is a rear view of the foul fluid splashing prevention device of the eighth embodiment of the present invention.
Figure 22:
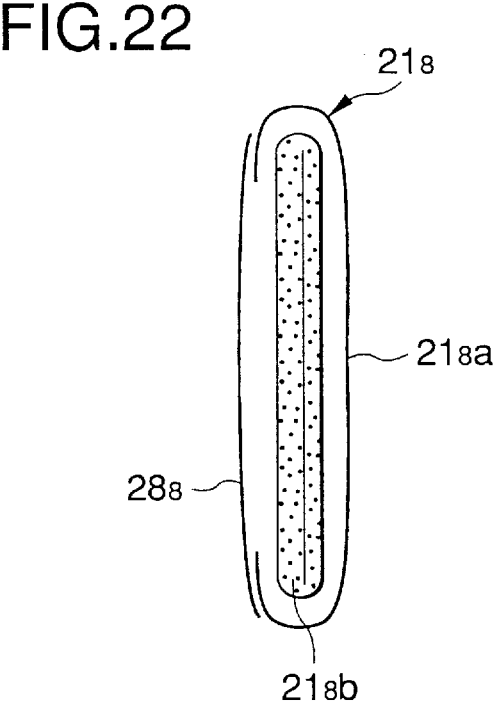
FIG. 22 is a cross section along line 22—22 of FIG. 20.

FIGS. 20 to 24 show another embodiment of the present invention. As illustrated in FIG. 22 which shows the section along line 22—22 of FIG. 20, a water-absorbing cloth (or non-woven fabric) $21_8a$, that serves as the foul fluid absorbing member, is provided in its interior with a substance $21_8b$ (for example, a high molecular weight water-impregnable polymer) having higher water absorbing properties that cloth $21_8a$. As shown in FIG. 21, the rear surface of the cloth $21_8a$ is provided with a waterproof cloth (or paper) $28_8$.

As shown in FIG. 20, the cloth $21_8a$ has a double-coated adhesive tape adhered onto its front surface side as the retaining member $122_8$. In use the retaining member $122_8$ is attached to the outer surface of a portion of the manipulating part 1 immediately above the protrusion 3 as shown in FIG. 23.

Figure 23:
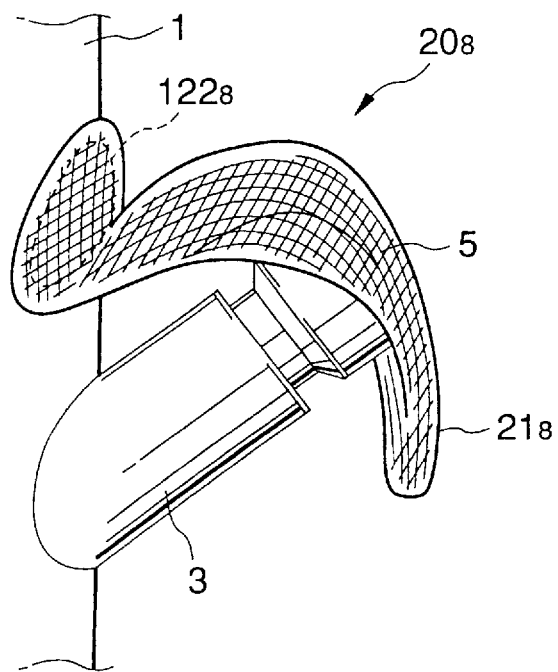
FIG. 23 is a partial side view which shows the usage condition in which the foul fluid splashing prevention device of the eighth embodiment of the present invention is attached to the manipulating part.
Figure 24:
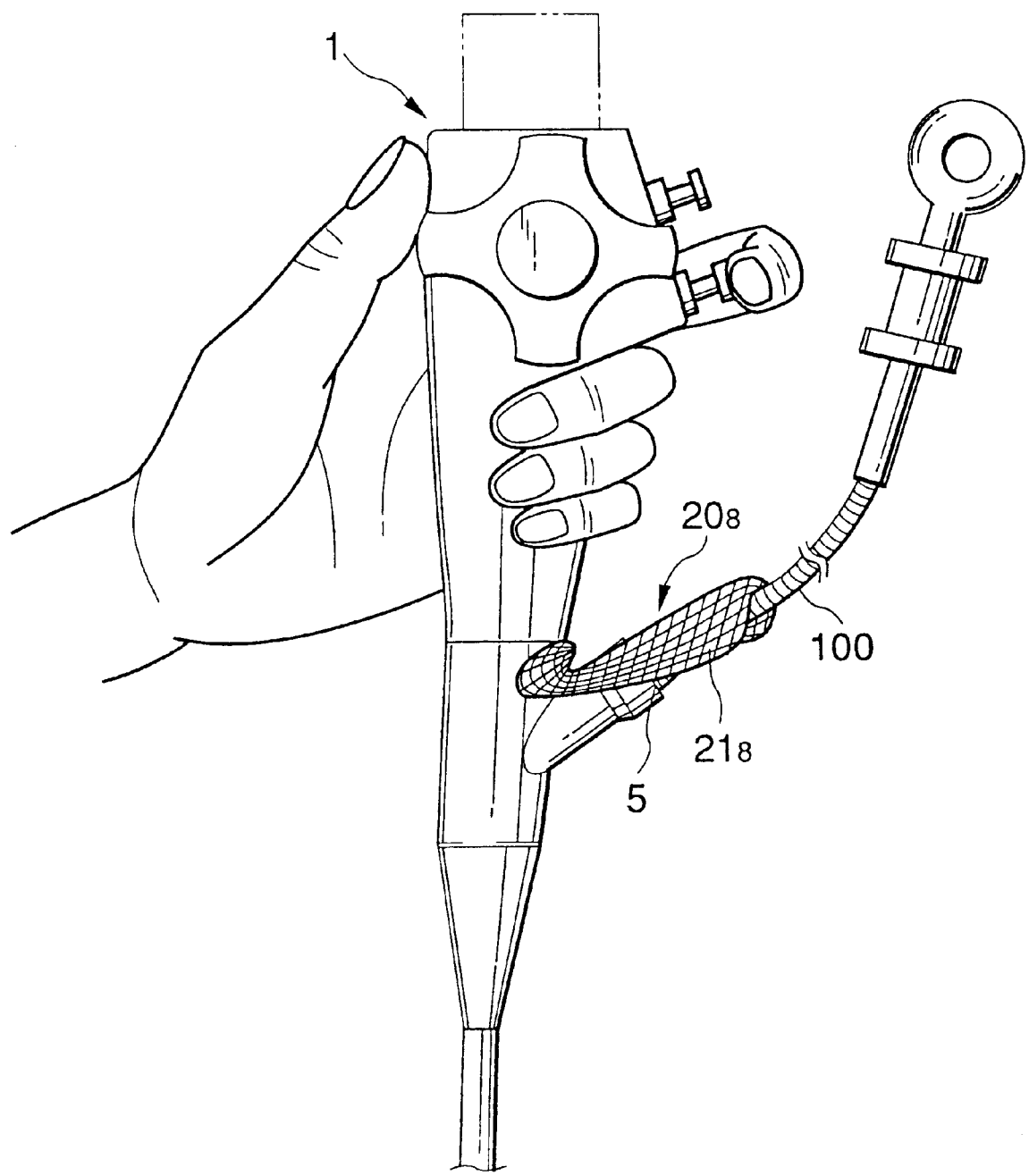
FIG. 24 is a side view which shows the condition in which an operative instrument is used with the foul fluid splashing prevention device of the eighth embodiment of the present invention being attached to the manipulating part.

Thus, as shown in FIG. 23, this embodiment also enables the operative instrument insertion entrance 5 to be covered with the foul fluid absorbing member $21_8$. During the use of the operative instrument, the operative instrument 100 that is inserted into operative instrument insertion entrance can be covered with the foul fluid absorbing member $21_8$ from the upper side as shown in FIG. 24.

Figure 25:
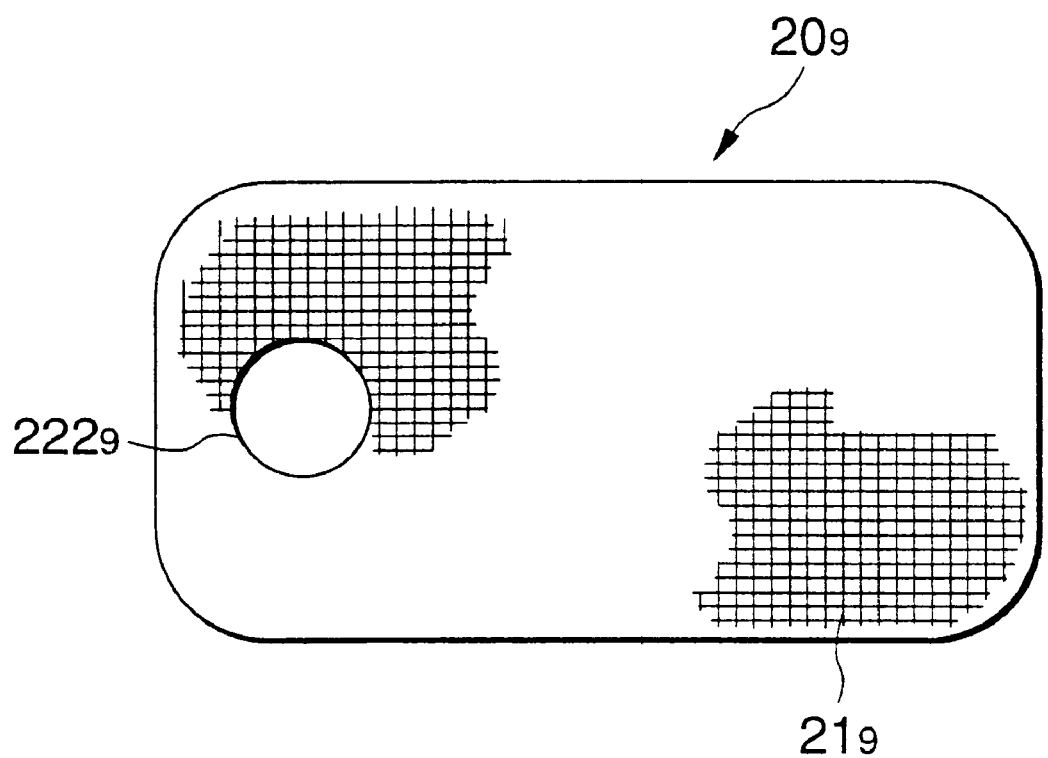
FIG. 25 is a front view of a foul fluid splashing prevention device of a ninth embodiment of the present invention.
Figure 26:
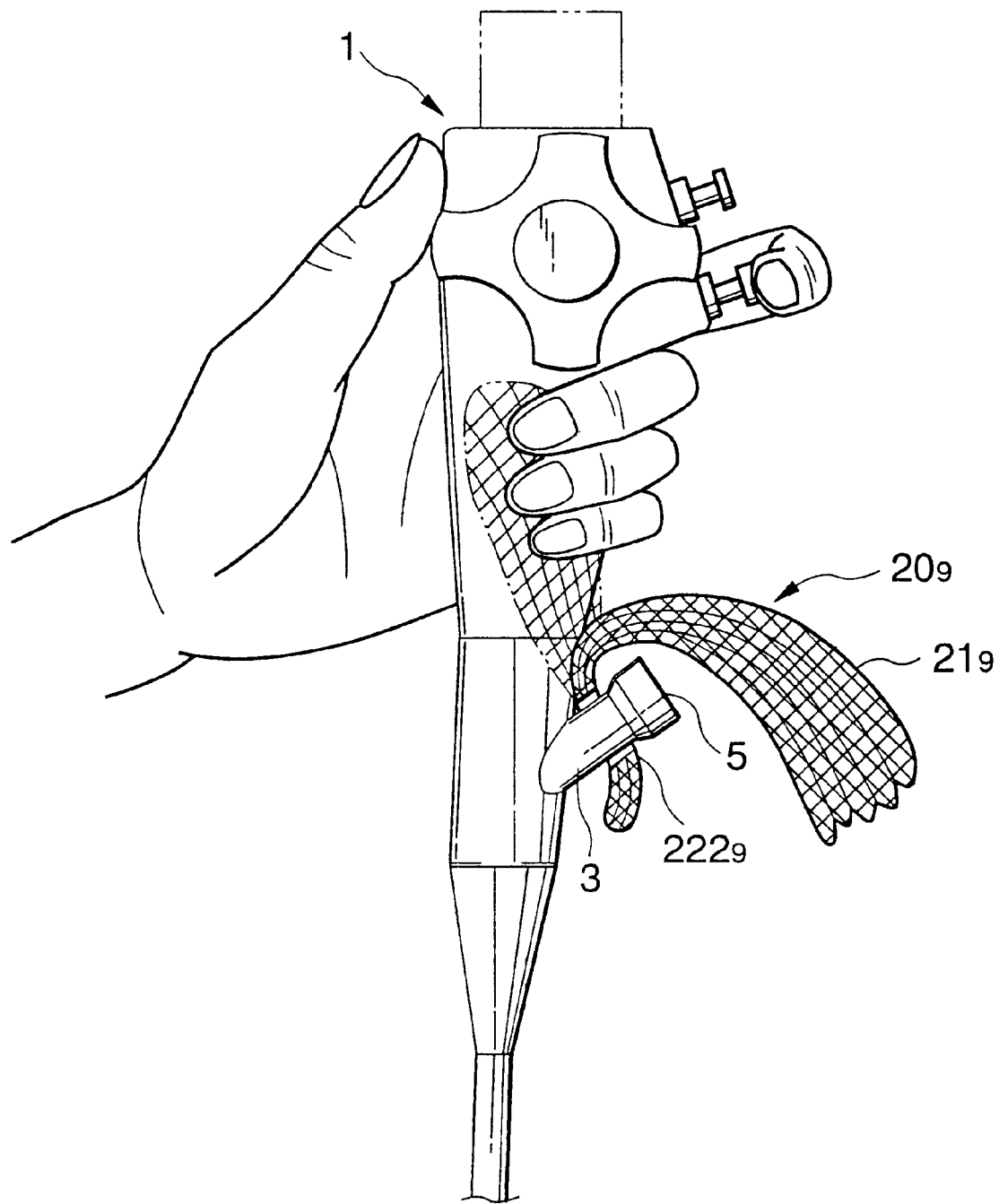
FIG. 26 is a side view partly in section which shows the usage condition in which the foul fluid splashing prevention device of the ninth embodiment of the present invention is attached to the manipulating part.

FIGS. 25 and 26 show another embodiment of the present invention in which a hole, that is adapted to engage with the protrusion 3 of the manipulating part 1, is bored in the foul fluid absorbing member $21_9$ to serve as the retaining member $222_9$. FIG. 25 is a front view of the foul fluid splashing prevention device $20_9$ and FIG. 26 shows the usage condition in which the protruding part 3 is passed through hole $222_9$. As is clear from this embodiment, any means can be used as the retaining member as long as it can retain the foul fluid absorbing member onto the manipulating part 1.

In case where the hole $222_9$ is adapted to engage the protruding part 3 of the manipulating part 1 is formed in the foul fluid absorbing member, the following arrangements are conceivable as additional means for more positively retaining the preventive device onto the manipulating part 1.

Figure 27:
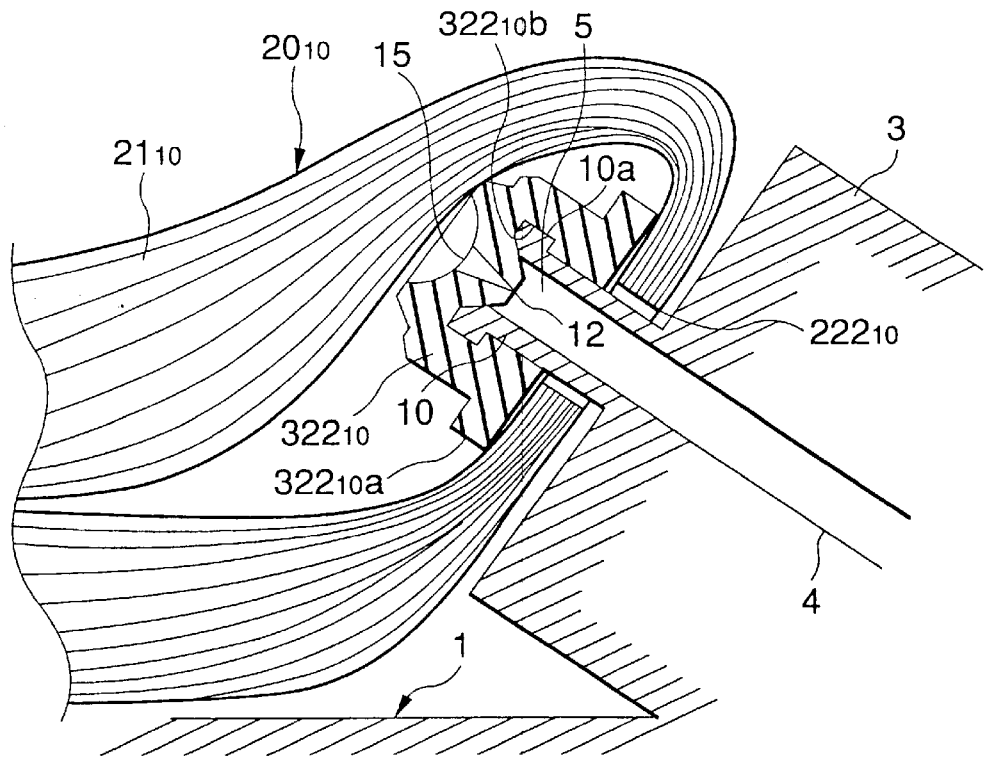
FIG. 27 is a section side view which shows the usage condition in which a foul fluid splashing prevention device of a tenth embodiment of the present invention is mounted to the manipulating part.

As shown in FIG. 27, a resilient, rubber forceps plug $322_{10}$ is detachably mounted to the end half of an insertion mouth 10. A flange-like stepped portion 10a is formed at the protruding end portion of the insertion mouthpiece 10, and an engaging hole $322_{10}b$ that is matched in shape with this stepped portion 10a is formed in the forceps plug $322_{10}$.

Thus, when the forceps plug $322_{10}$ is forced against the insertion mouthpiece 10 with the application of a slightly strong force so that the insertion mouthpiece 10 is fitted into the engaging hole $322_{10}b$ of forceps plug $322_{10}$, the forceps plug $322_{10}$ elastically deforms to cover the insertion mouthpiece 10, so that the forceps plug $322_{10}$ is attached to the insertion mouthpiece 10 in a stable manner with the stepped portion at its tip preventing the removal of the forceps plug $322_{10}$ as shown in FIG. 27. In addition, if the forceps plug $322_{10}$ is pinched with the fingertips, etc. and a slightly strong twisting force is applied thereto, the forceps plug $322_{10}$ can be removed from the insertion mouthpiece 10 while undergoing elastic deformation.

In the condition when the forceps plug $322_{10}$ is attached to the insertion mouthpiece 10, the central portion of the forceps plug $322_{10}$ depressingly fits into the inside of the mouth of the insertion mouthpiece 10 (in other words, the inside of the operative instrument insertion entrance 5). Thus the operative instrument insertion entrance 5 is sealed.

A slit 12, which is generally closed, is formed at the central portion of the forceps plug $322_{10}$. The slit 12 is formed at the bottom of a tapered hole that spreads gradually outward, and the outer end portion of this tapered hole serves as the operative instrument insertion entrance 15 of forceps plug $322_{10}$. Operative instruments (not shown) are passed through the slit 12 upon being inserted via this tapered hole.

When the operative instrument is inserted, the slit undergoes elastic deformation and spreads, and the tip of the operative instrument is passed inside the forceps channel 4 and extends towards the affected part from a front end exit (not shown).

Figure 28:
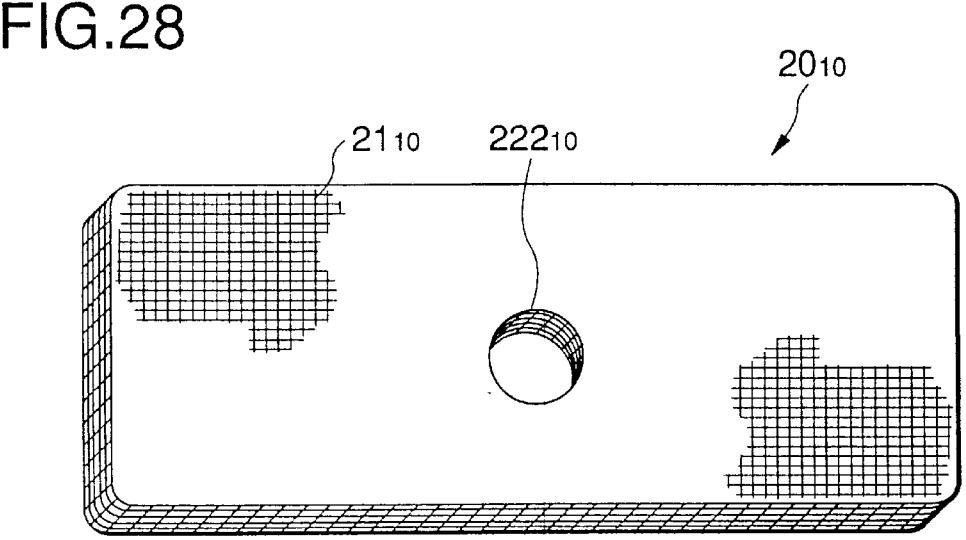
FIG. 28 is a perspective view of the foul fluid splashing prevention device of the tenth embodiment of the present invention.

As shown in FIG. 28, the foul fluid splashing prevention device $20_{10}$ includes a foul fluid absorbing member $21_{10}$ made of water-absorbing material such as flexible gauze, high molecular weight water-impregnable polymer, hydrophilic non-woven cloth, etc., which has, at its central portion, a mounting hole $222_{10}$, of a diameter that permits the insertion mouthpiece 10 to be inserted loosely. When the endoscope is to be used, the insertion mouthpiece 10 is inserted into the mounting hole $222_{10}$ and the forceps plug $322_{10}$ is thereafter attached to the tip of the insertion mouthpiece 10 as shown in FIG. 27.

Since the forceps plug $322_{10}$ is mounted to the insertion mouthpiece 10 in a capping manner, the foul fluid splashing prevention device $20_{10}$ is retained and positively prevented from being removed from the insertion mouthpiece 10.

A flange $322_{10}a$ protrudes from the bottom portion of the forceps $322_{10}$ that faces the foul fluid absorbing member $21_{10}$ so as to retain the foul fluid absorbing member $21_{10}$ in a stable manner over a wide area.

To remove the foul fluid splashing prevention device $20_{10}$ from the manipulating part 1, the forceps plug $322_{10}$ is simply removed from the insertion mouthpiece 10. The foul fluid splashing prevention device $20_{10}$ can thus be mounted securely and in a stable manner to the manipulating part 1 and can also be readily detached from the manipulating part 1.

With the foul fluid splashing prevention device $20_{10}$ that is mounted to the insertion mouthpiece 10, a half portion of the foul fluid absorbing member $21_{10}$ is folded back in a U-turn like manner and made to cover the operative instrument insertion entrance 15 part of the forceps plug $322_{10}$.

Figure 29:
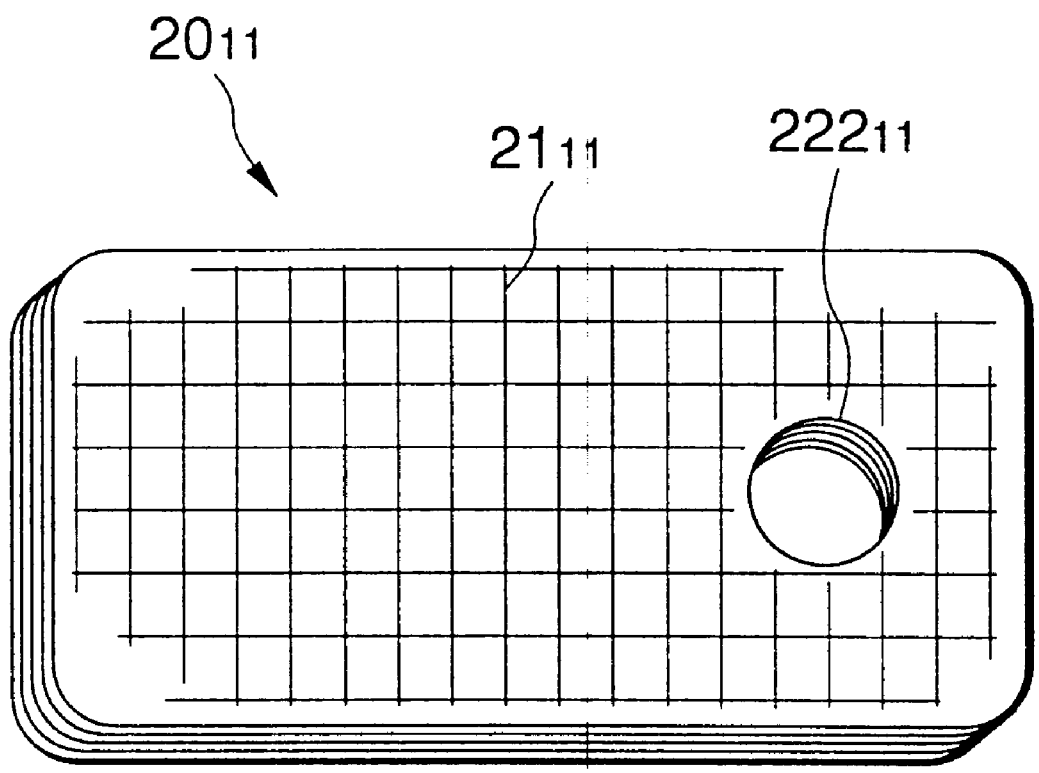
FIG. 29 is a perspective view of a foul fluid splashing prevention device of an eleventh embodiment of the present invention.
Figure 30:
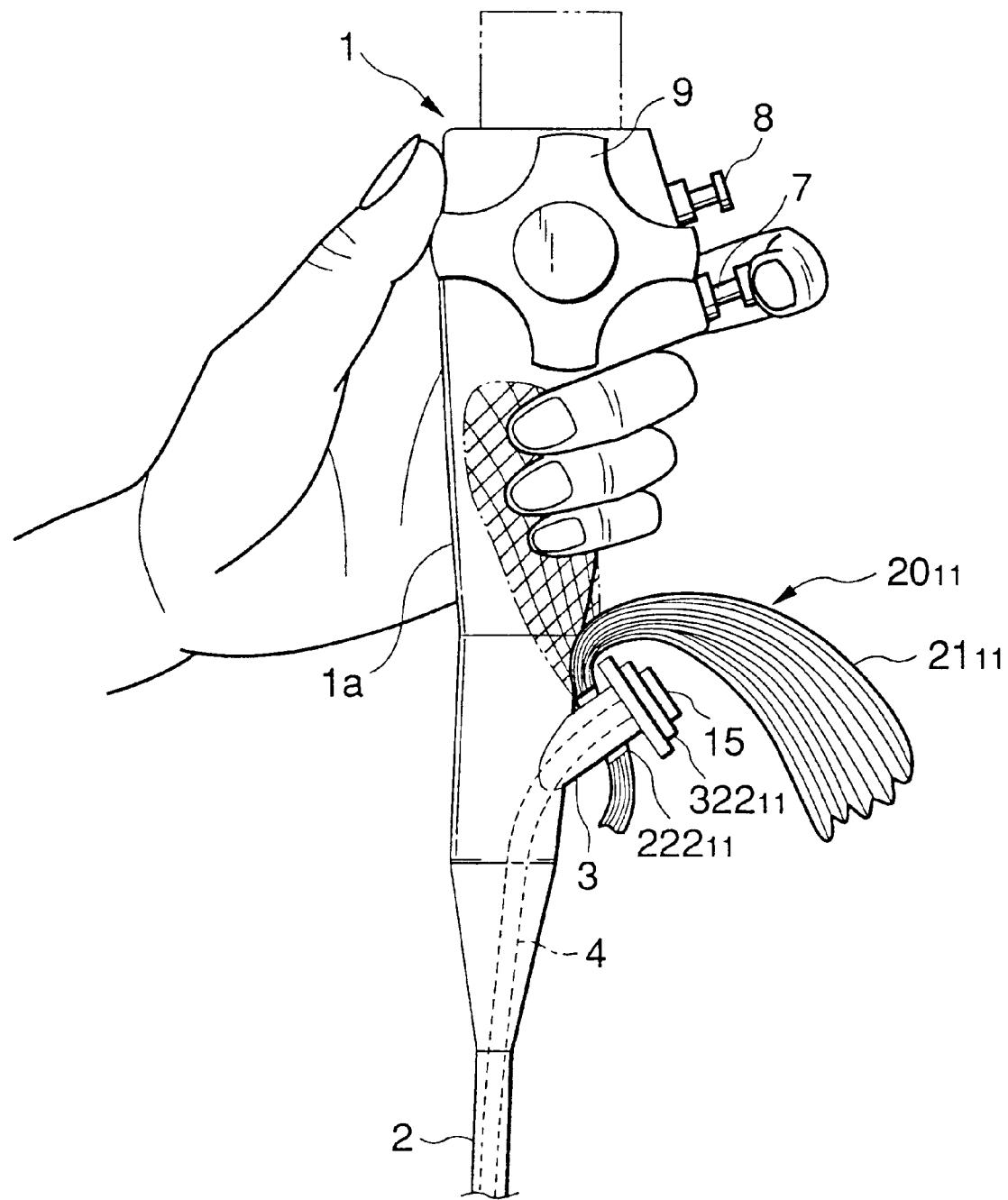
FIG. 30 is a side view partly in section which shows the usage condition in which the foul fluid splashing prevention device of the eleventh embodiment of the present invention is mounted to the manipulating part.

FIGS. 29 and 30 show another embodiment of the present invention in which a mounting hole $222_{11}$ is disposed not at the center of the foul fluid absorbing member $21_{11}$ but offset towards the side similar to the embodiment shown in FIGS. 25 and 26. The mounting hole $222_{11}$ is engaged with the protrusion 3 of the manipulating part 1 and then the forceps plug $322_{11}$ is mounted above the foul fluid absorbing member $21_{11}$ to the protrusion 3 in a covering manner. The longitudinal side of the foul fluid absorbing member $21_{11}$ is disposed so as to cover the operative instrument insertion entrance 15 of the forceps plug $322_{11}$ from above.

If the covering of the operative instrument insertion entrance 15 by the foul fluid splashing prevention device $20_{11}$ causes a hindrance, the foul fluid absorbing member $21_{11}$ can be gripped along with the grip part 1a of the manipulating part 1 as shown by the dashed line of FIG. 30.

Figure 31:
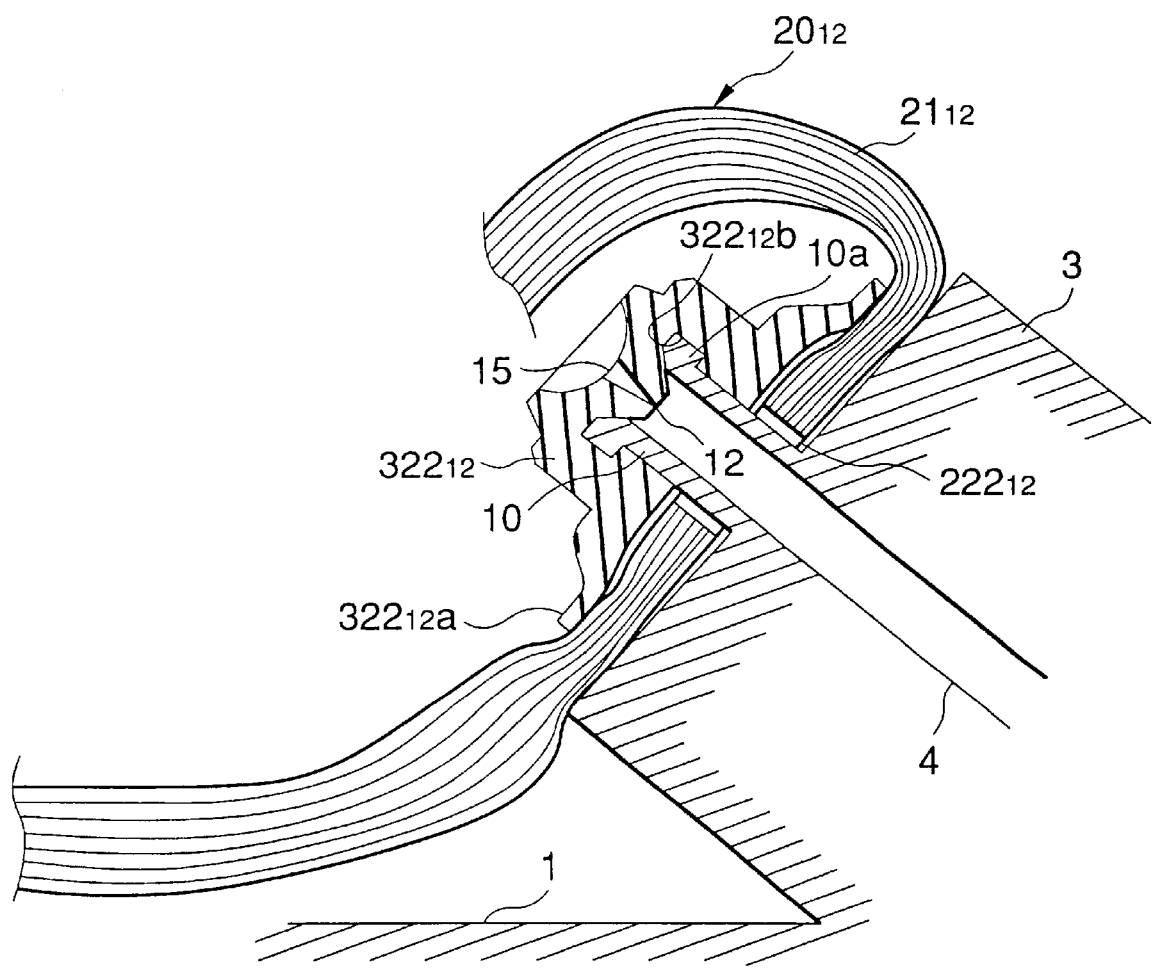
FIG. 31 is a sectional side view which shows the usage condition in which a foul fluid splashing prevention device of a twelfth embodiment of the present invention is mounted to the manipulating part.

FIG. 31 shows another embodiment of the present invention in which the flange $322_{12}$ of the forceps plug $322_{12}$ that depressingly retains foul fluid absorbing member $21_{12}$ is made large so that foul the fluid splashing prevention device $20_{12}$ can be retained more firmly.

Figure 32:
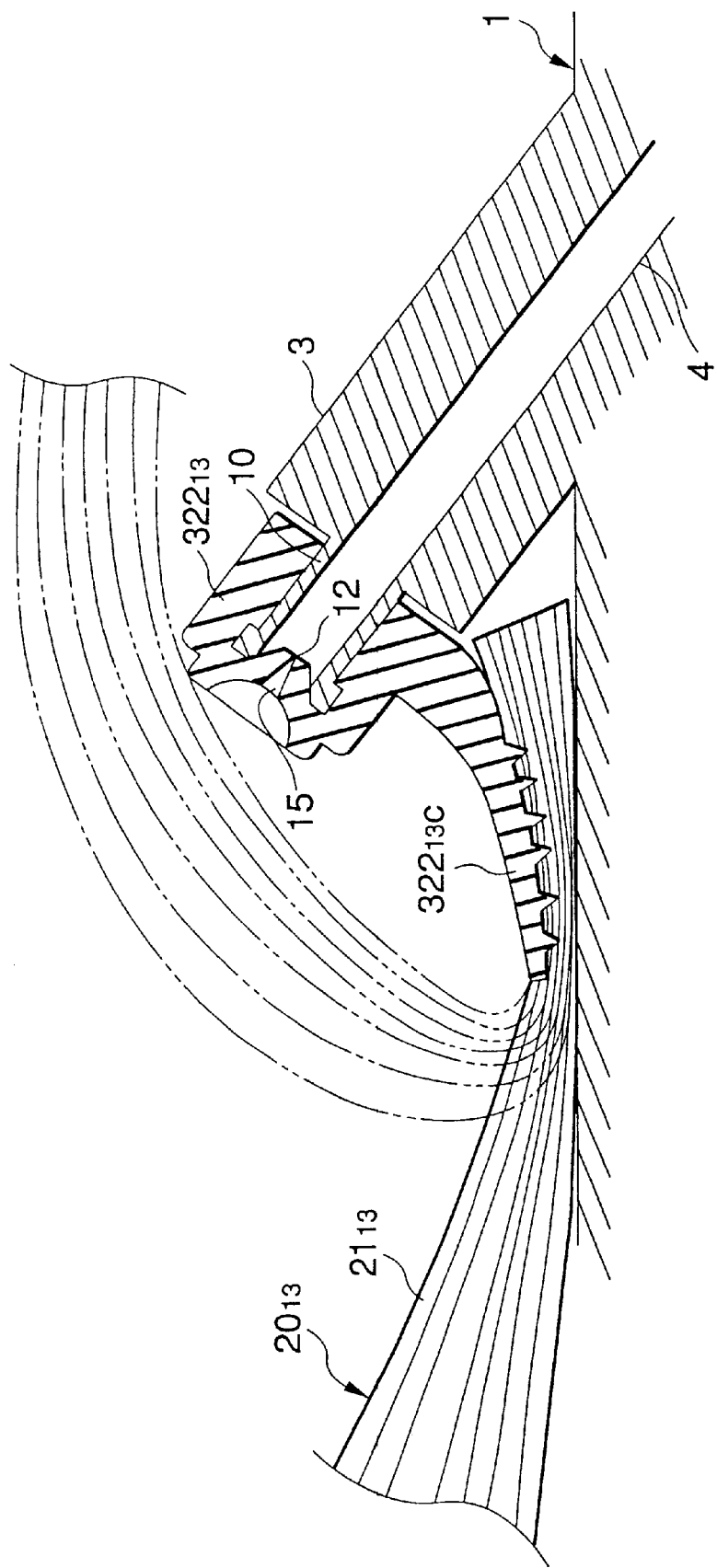
FIG. 32 is a section side view which shows the usage condition in which a foul fluid splashing prevention device of a thirteenth embodiment if the present invention is mounted to the manipulating part.
Figure 33:
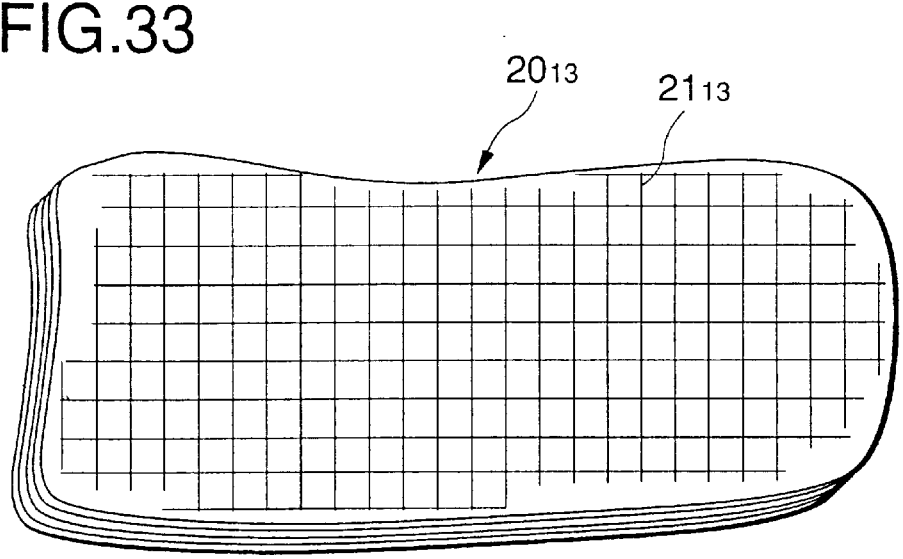
FIG. 33 is a perspective view of a part of the foul fluid splashing prevention device of the thirteenth embodiment of the present invention.

FIGS. 32 and 33 show another embodiment of the present invention in which an alligator-tail-like tail part $322_{13}c$ is formed on the forceps plug $322_{13}$ which is mounted to the insertion mouthpiece 10 at the tip of the protrusion 3, and the foul fluid absorbing member $21_{13}$ is retained by being clamped between this tail part $322_{13}c$ and the surface of manipulating part 1. In this case, there is no need to form a mounting hole in the foul fluid absorbing member $21_{13}$ as shown in FIG. 33.

Figure 34:
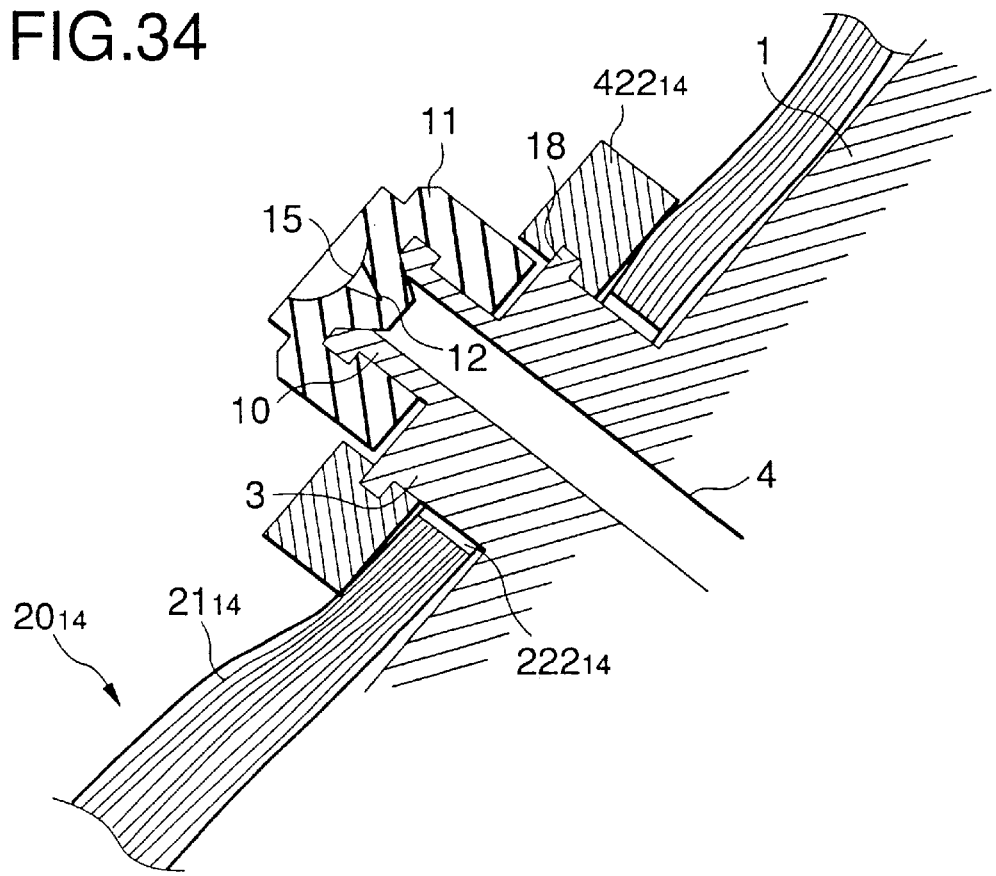
FIG. 34 is a sectional side view which shows the usage condition in which a foul fluid splashing prevention device of a fourteenth embodiment of the present invention is mount to the manipulating part.

FIG. 34 shows another embodiment of the present invention in which a mounting hole $222_{14}$ is formed in the foul fluid absorbing member $21_{14}$. This mounting hole $222_{14}$ is engaged with the protrusion 3 of the manipulating part 1, and the foul fluid absorbing member $21_{14}$ is held in place by a presser member $422_{14}$ provided as a member from a forceps plug 11 and mounted above the absorbing member $21_{14}$.

The presser member $422_{14}$ is made from resilient rubber and can be elastically deformed and thus readily attached to and detached from a flange part 18 protruded from the protrusion 3 without removing the forceps plug 1. The foul fluid splashing prevention device $20_{14}$ can thus be replaced readily even during endoscopy.

Figure 35:
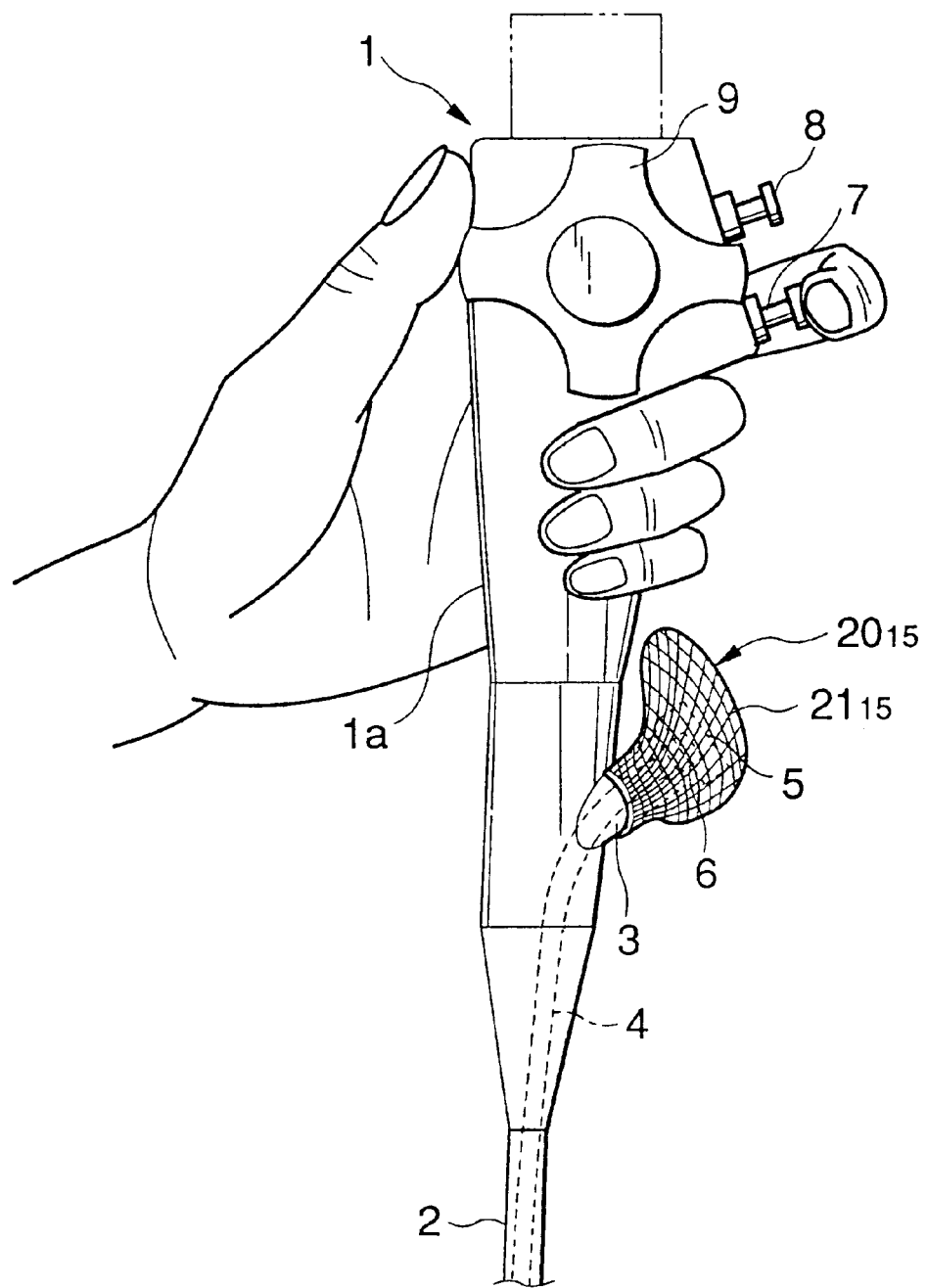
FIG. 35 is a side view which illustrates the usage condition in which a foul fluid splashing prevention device of a fifteenth embodiment of the present invention is attached to the manipulative part.
Figure 36:
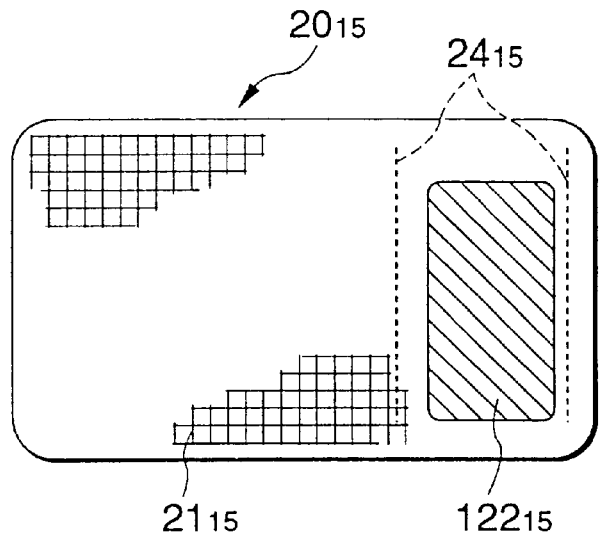
FIG. 36 is a front view of the foul fluid splashing prevention device of the fifteenth embodiment of the present invention.
Figure 38:
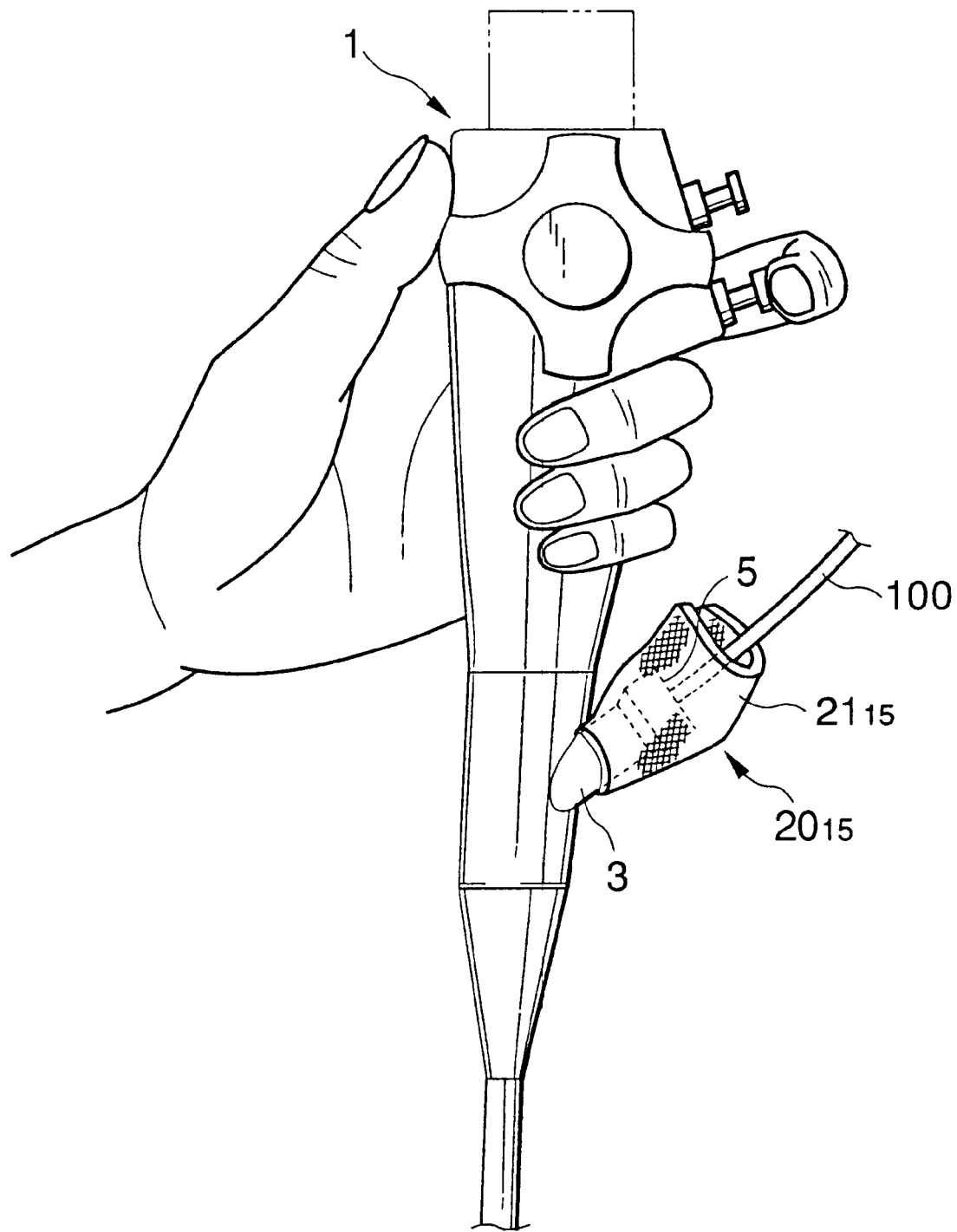
FIG. 38 is a side view which illustrates the usage condition in which an operative instrument is used with the foul fluid splashing prevention device of the fifteenth embodiment of the present invention being attached to the manipulating part.

FIGS. 35 and 38 show another embodiment of the present invention. As shown in FIG. 36, a rectangular, sheet-form, foul fluid absorbing member $21_{15}$ is formed by folding over and overlapping a plurality of sheets of water-absorbing material, such as flexible gauze. A pressure-sensitive adhesive surface $122_{15}$ is formed near one of the short sides of the foul fluid absorbing member $21_{15}$.

The pressure-sensitive surface $122_{15}$ undergoes very little deterioration in normal environments and is adhered by pressure-application onto the surface to which it is intended to be attached. Note that the force of adhesion onto a plastic or metal surface, etc., is not strong and the pressure-sensitive adhesive surface $122_{15}$ can be detached therefrom by applying a slightly strong force.

The foul fluid absorbing member $21_{15}$ is machine sewn at both sides of the pressure-sensitive adhesive surface $122_{15}$. Reference numeral $24_{15}$ designates the machine-sewn seam. The material of the foul fluid absorbing member $21_{15}$ is not limited to a gauze and a wide variety of flexible, water-absorbing materials, such as sponge, non-woven fabric, high molecular weight water-impregnable polymer, or an open cell material such as PVA sponge, etc., can be used.

The foul fluid splashing prevention device $20_{15}$, that has been formed in the above manner, is attached to the manipulating part 1 with the pressure-sensitive adhesive surface $122_{15}$ being pressed against and adhered onto the lower-end peripheral surface of the protrusion 3.

Figure 37:
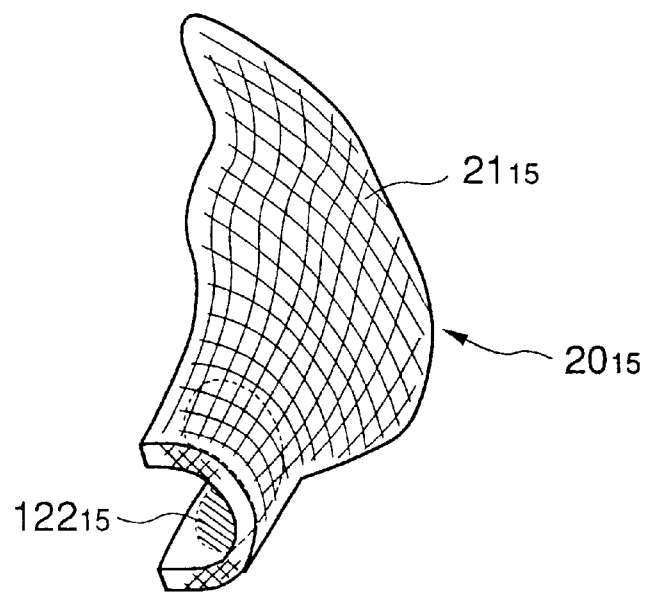
FIG. 37 is a perspective view which illustrates the first usage condition of the foul fluid splashing prevention device of the fifteenth embodiment of the present invention.

FIG. 37 shows the foul fluid splashing prevention device $20_{15}$ in this condition. The pressure-sensitive adhesive surface ($122_{15}$) portion presents a U-like form extending along nearly half the circumference of the outer peripheral surface of the protrusion 3 and the foul fluid absorbing member $21_{15}$ is oriented upwards.

As shown in FIG. 35, the foul fluid absorbing member $21_{15}$ is disposed so as to cover the operative instrument insertion entrance 5 at the tip portion of the protrusion 3.

When an operative instrument is to be inserted into the forceps channel 4, the foul fluid absorbing member $21_{15}$ that is covering the operative instrument insertion entrance 5 is made to present a slightly open U-like shape as shown in FIG. 38 and the operative instrument 100 is inserted into the forceps channel 4 from the operative instrument insertion entrance 5.

Figure 39:
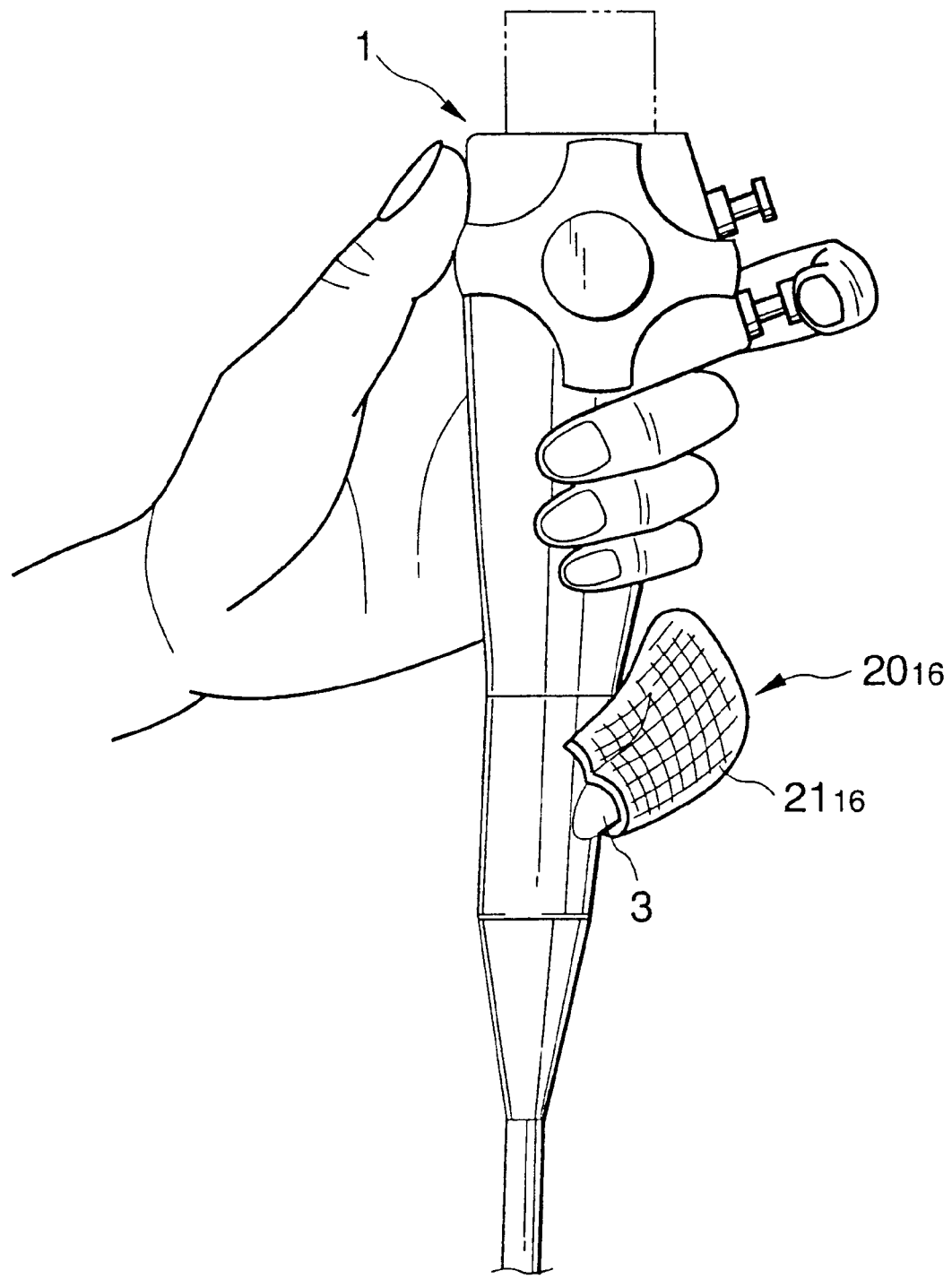
FIG. 39 is a side view which illustrates the usage condition in which a foul fluid splashing prevention device of a sixteenth embodiment of the present invention is attached to the manipulating part.
Figure 40:
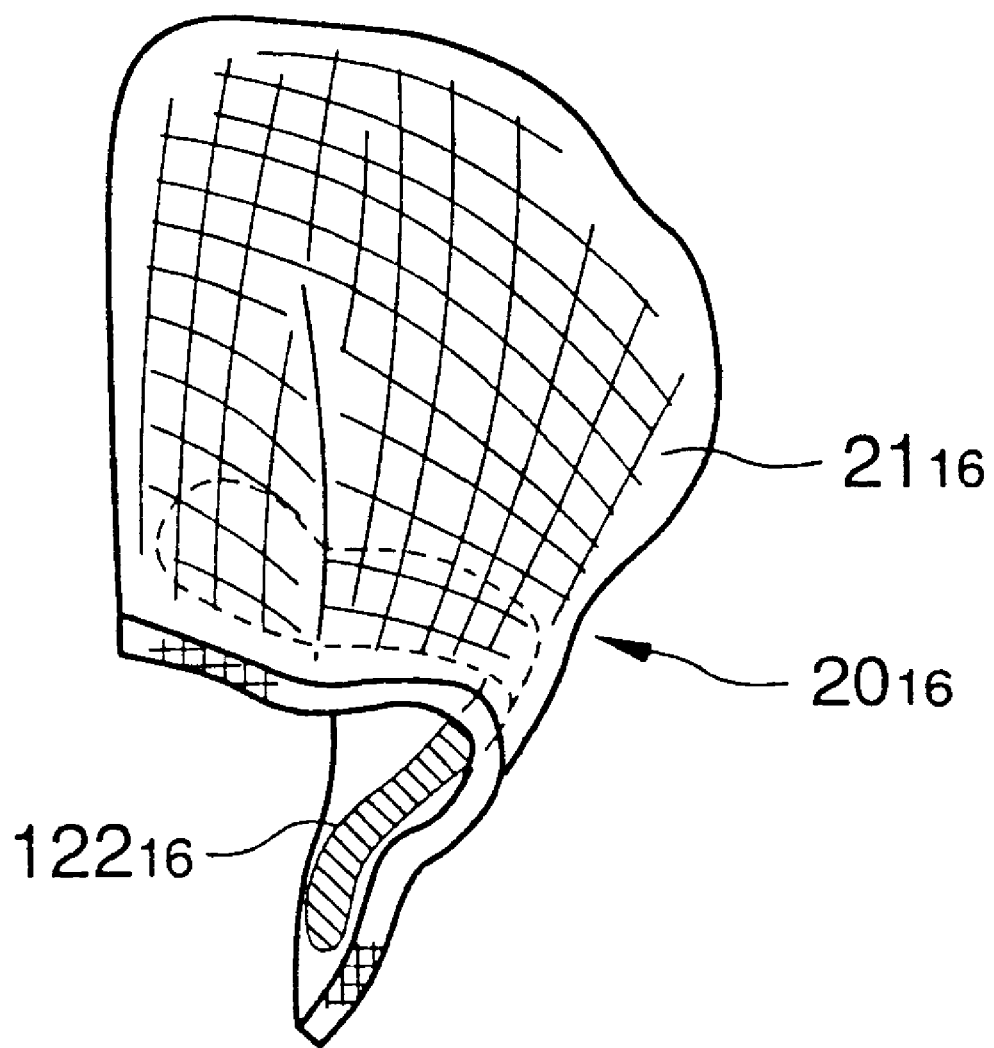
FIG. 40 is perspective view which illustrates the usage condition of the foul fluid splashing prevention device of the sixteenth embodiment of the present invention.

FIG. 39 illustrates the case where the width of the foul fluid absorbing member $21_{16}$ is widened and the pressure-sensitive adhesive surface $122_{16}$ is adhered onto an area extending from the outer peripheral surface of the protrusion 3 to the outer peripheral surface of the base side of the manipulating part 1. In this case, the foul fluid splashing prevention device $20_{16}$ can be adhered in a more stable manner. FIG. 40 shows the foul fluid splashing prevention device in this condition.

Figure 41:
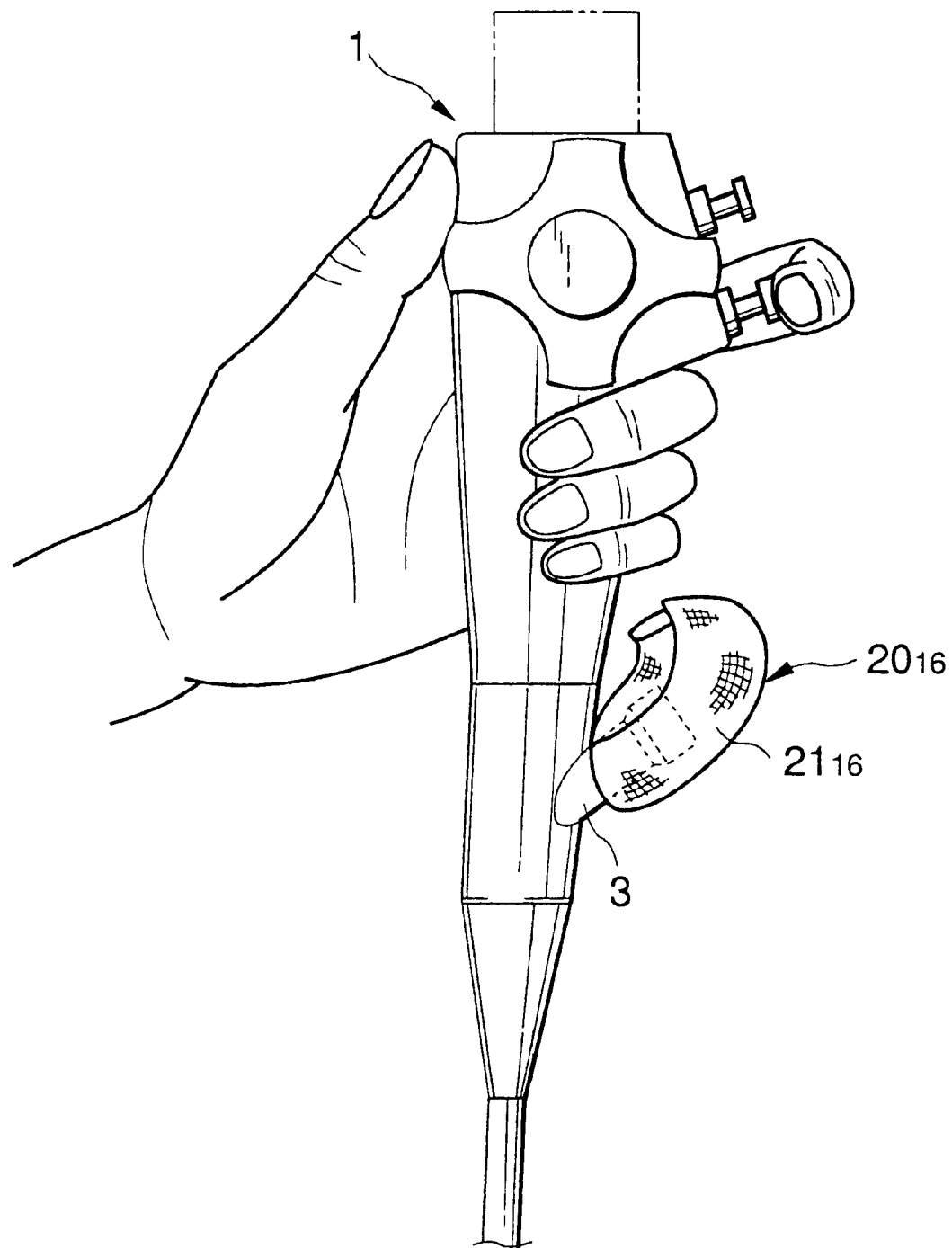
FIG. 41 is a side view which illustrates the usage condition in which the foul fluid splashing prevention device of the sixteenth embodiment if the present invention is attached to the manipulating part.

FIG. 41 illustrates the case when the foul fluid absorbing member $21_{16}$ is attached across the entire circumference of the outer peripheral surface of protrusion 3. In this case, since pressure-sensitive adhesive surface $122_{16}$ is adhered onto the outer peripheral surface of the protrusion 3 in a band-like manner, the foul fluid splashing prevention device $20_{16}$ can be adhered in an even more stable condition.

Figure 42:
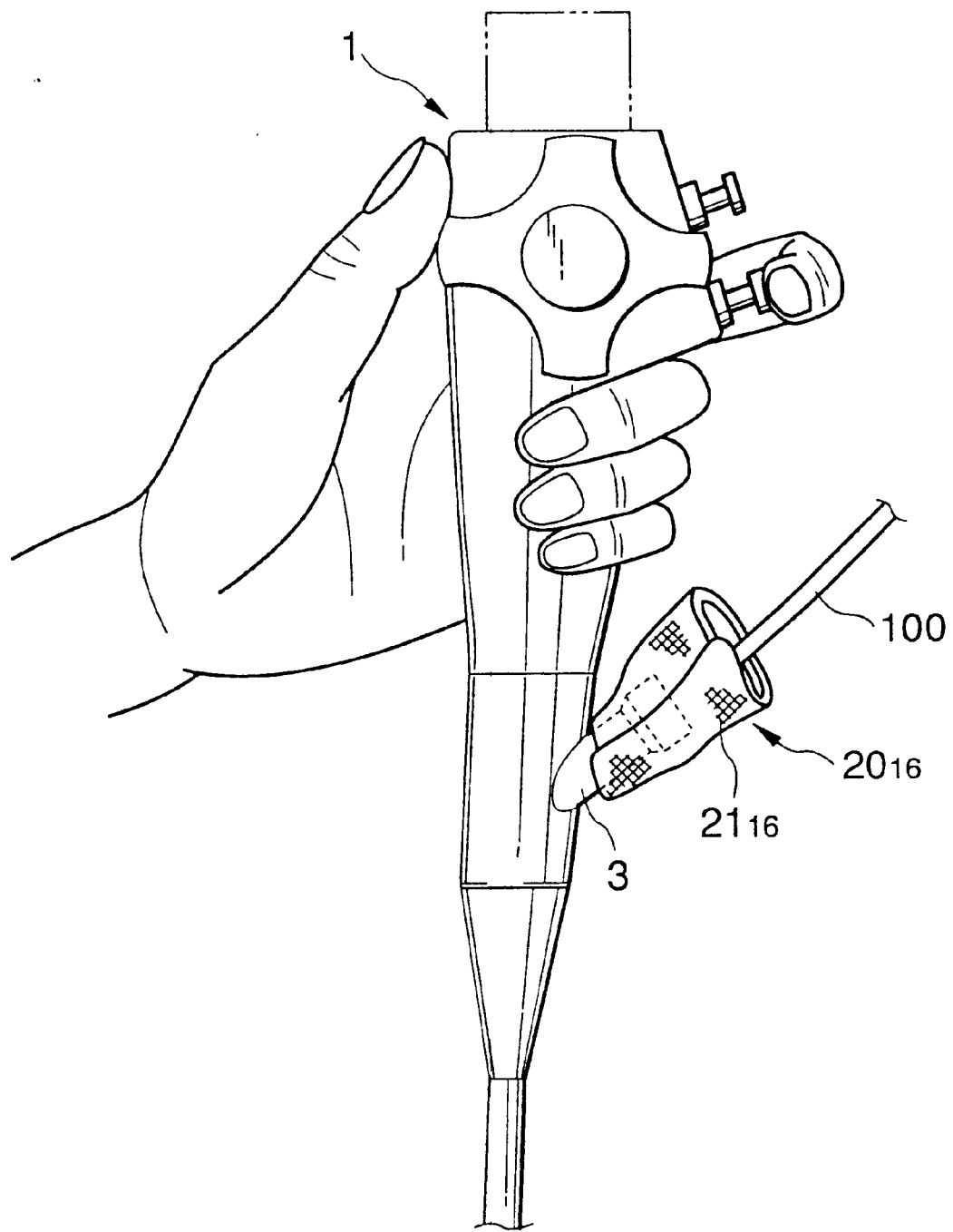
FIG. 42 is a side view which illustrates the usage condition in which an operative instrument is used with the foul fluid splashing prevention device of the sixteenth embodiment of the present invention being attached to the manipulating part.
Figure 43:
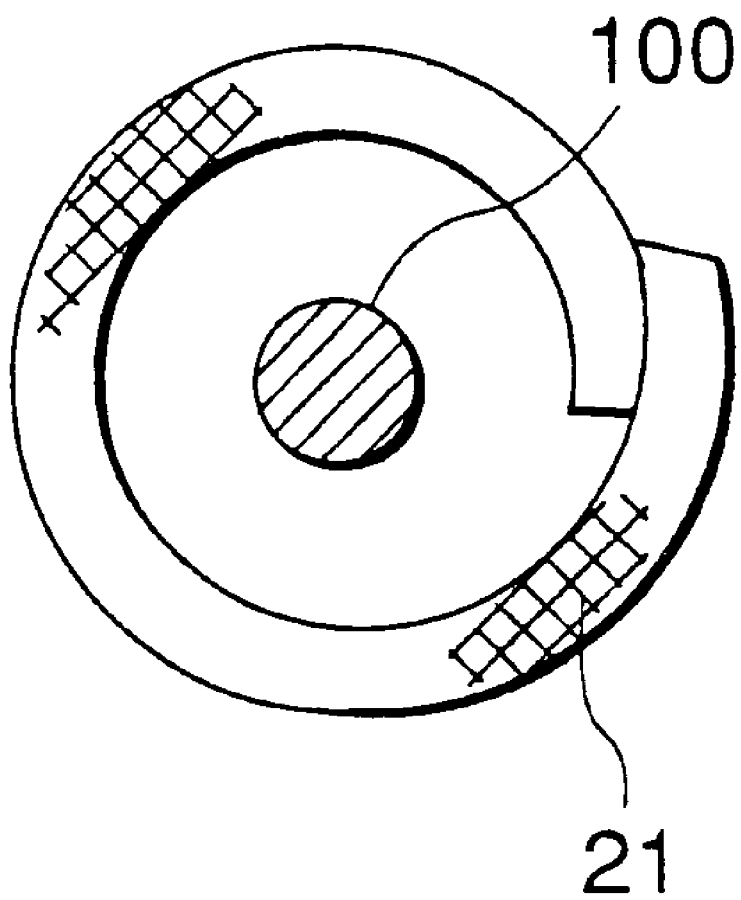
FIG. 43 is a transverse cross-sectional view which illustrates the usage condition in which an operative instrument is used with the foul fluid splashing prevention device of the sixteenth embodiment of the present invention being attached to the manipulating part.

FIG. 42 shows the condition in which the operative instrument 100 is used in the case where the foul fluid splashing prevention device $20_{16}$ is attached to the manipulating part 1 in the above manner, and as shown by the transverse cross section in FIG. 43, the operative instrument 100 is passed through the internal space part formed by the foul fluid absorbing member $21_{16}$ formed into a tubular shape.

Figure 44:
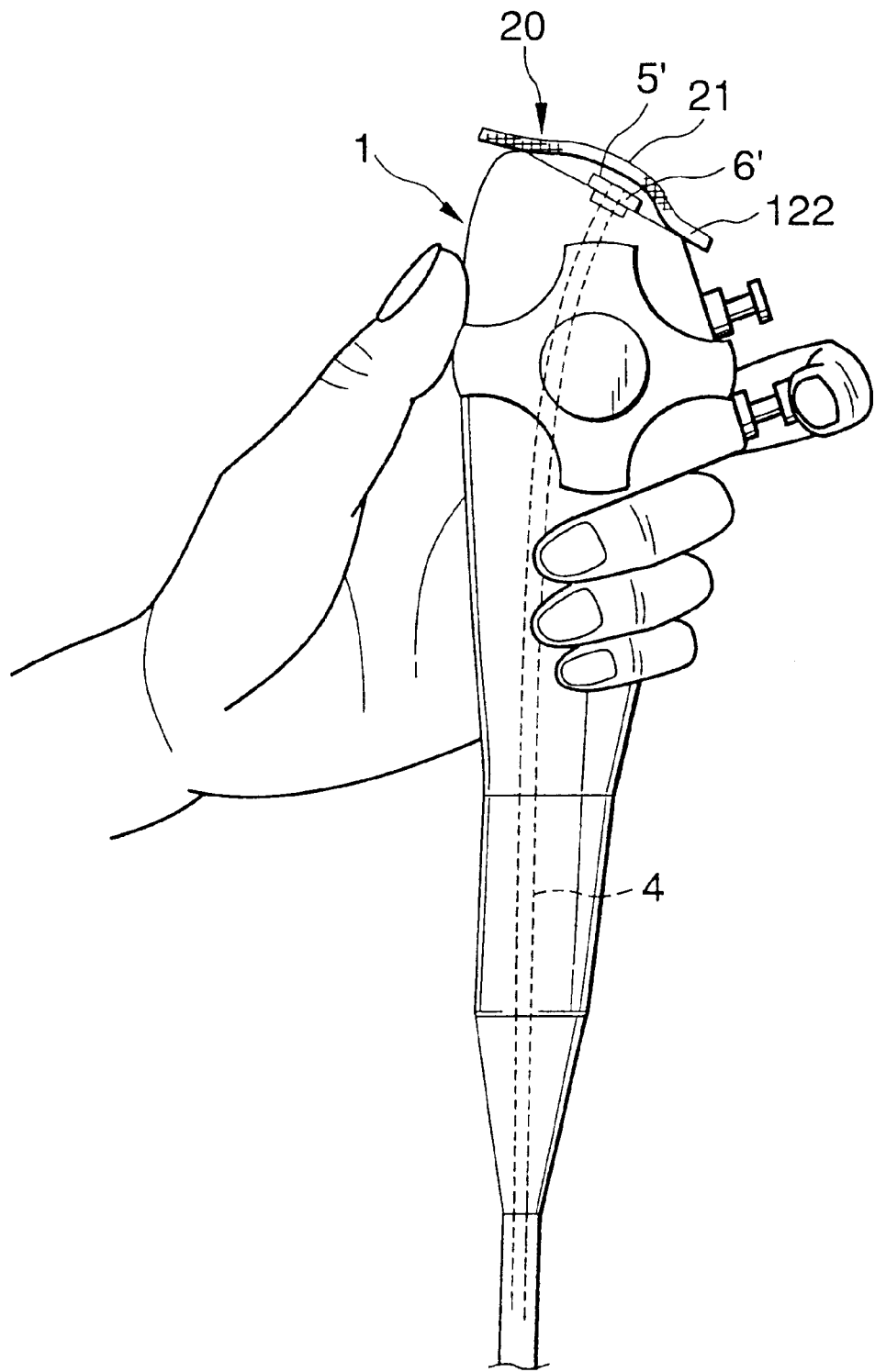
FIG. 44 is a side view which illustrates the usage condition in which the foul fluid splashing prevention device of the sixteenth embodiment of the present invention is attached to the manipulating part.

FIG. 44 illustrates the case where the operative instrument insertion entrance 5' is disposed at a flat portion of the manipulating part 1. In this case, the pressure-sensitive adhesive surface $122_{16}$ is adhered onto the flat portion adjacent the operative instrument insertion entrance 5' so that the foul fluid absorbing member $21_{16}$ covers the operative insertion entrance 5'.

Figure 45:
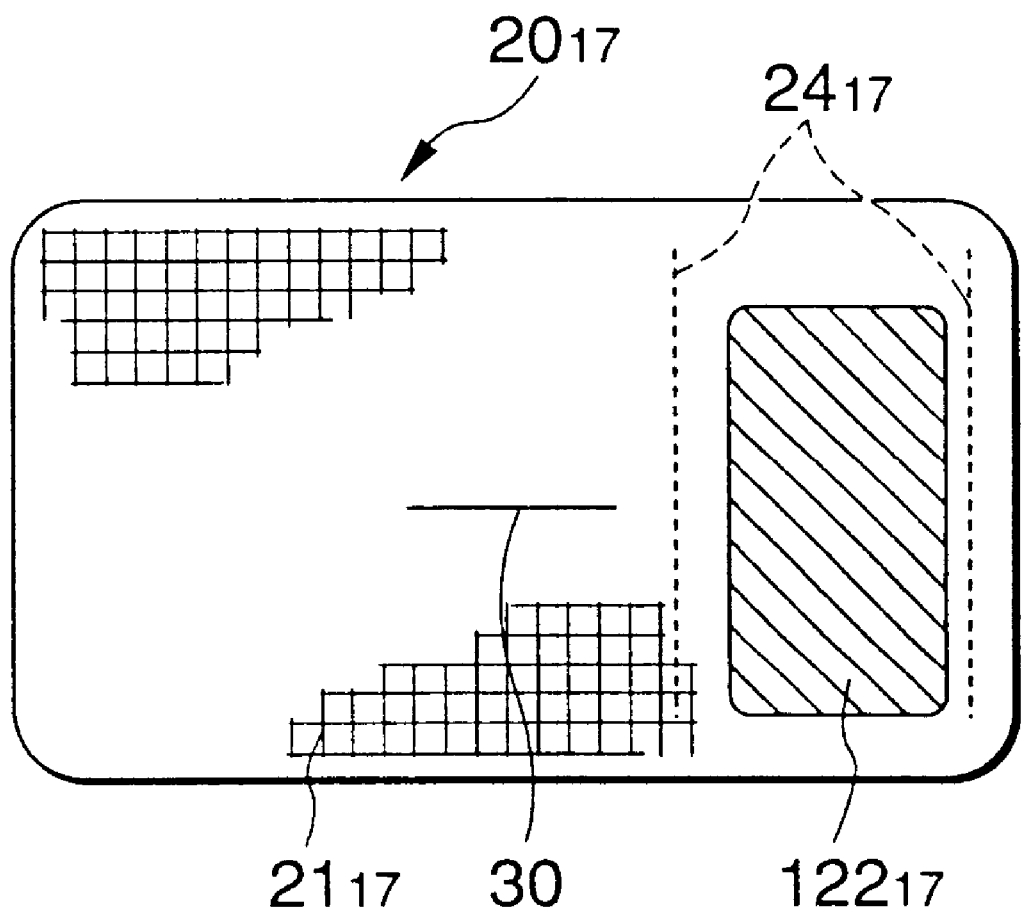
FIG. 45 is a front view of a foul fluid splashing prevention device of a seventeenth embodiment of the present invention.

When the operative instrument 100 is to be used, the foul fluid absorbing member $21_{16}$ is withdrawn from the operative instrument insertion entrance 5'. Alternatively, a slit 30 may be formed at the portion of the foul fluid absorbing member $21_{17}$ that faces the operative insertion entrance 5' as shown in FIG. 45 so that the operative instrument 100 can be passed through this slit 30.

Figure 46:
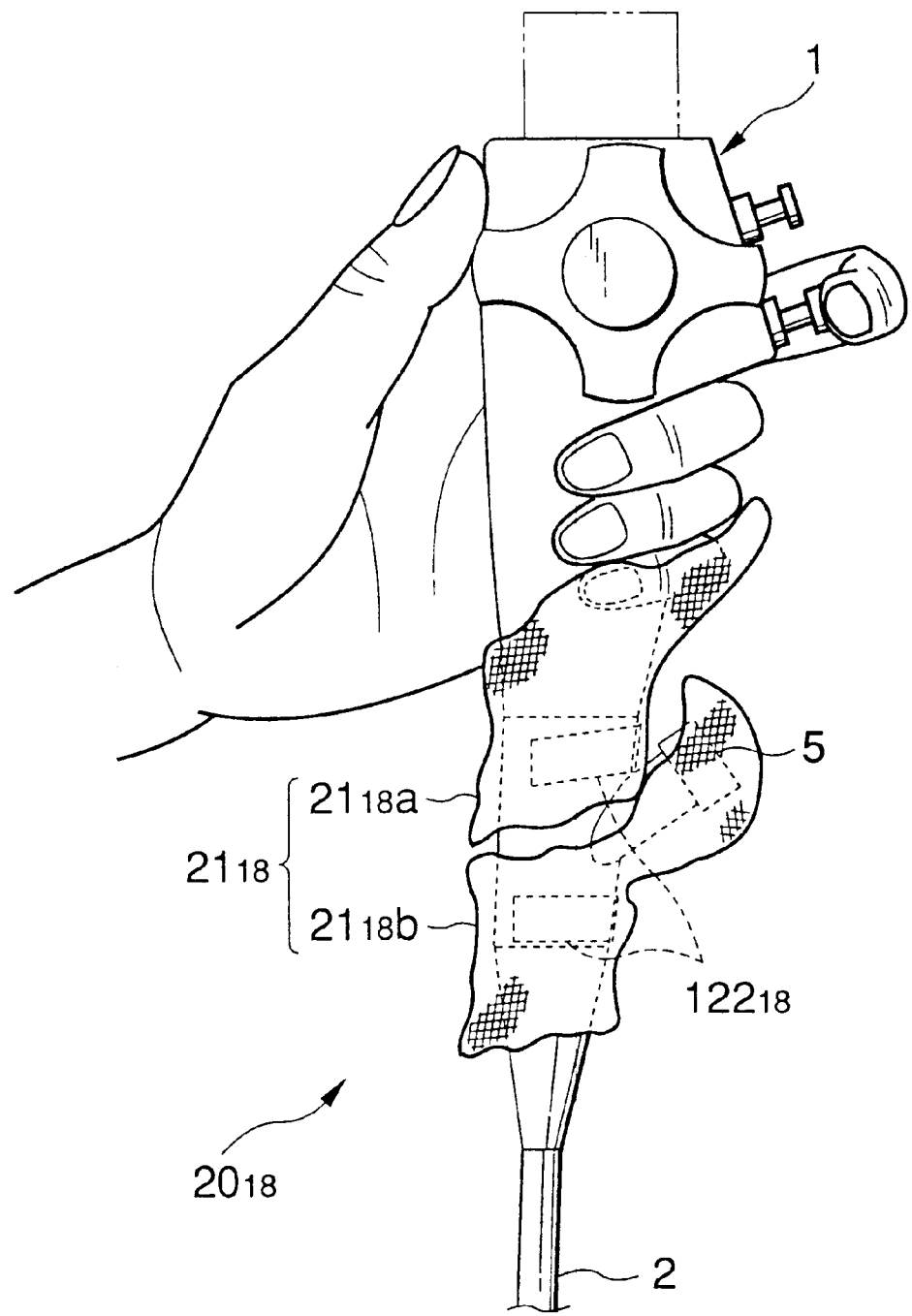
FIG. 46 is a side view of the usage condition in which a foul fluid splashing prevention device of an eighteenth embodiment of the present invention is attached to the manipulating part.

FIG. 46 shows the condition in which a pair of foul fluid absorbing members $21_{18}a$ and $21_{18}b$ are attached to the manipulating part 2. That is, the upper foul fluid absorbing member $21_{18}a$ and lower foul fluid absorbing member $21_{18}b$ are respectively adhered onto the outer wall face of manipulating part 2 by pressure-sensitive adhesive agents $122_{18}$.

So-called double-coated adhesive tape, etc. can be used as the pressure-sensitive adhesive agent $122_{18}$, and when endoscopy is ended, the foul fluid absorbing member $21_{18}$ is peeled off from the surface of manipulating part 2 and can be replaced with a new item.

Figure 47:
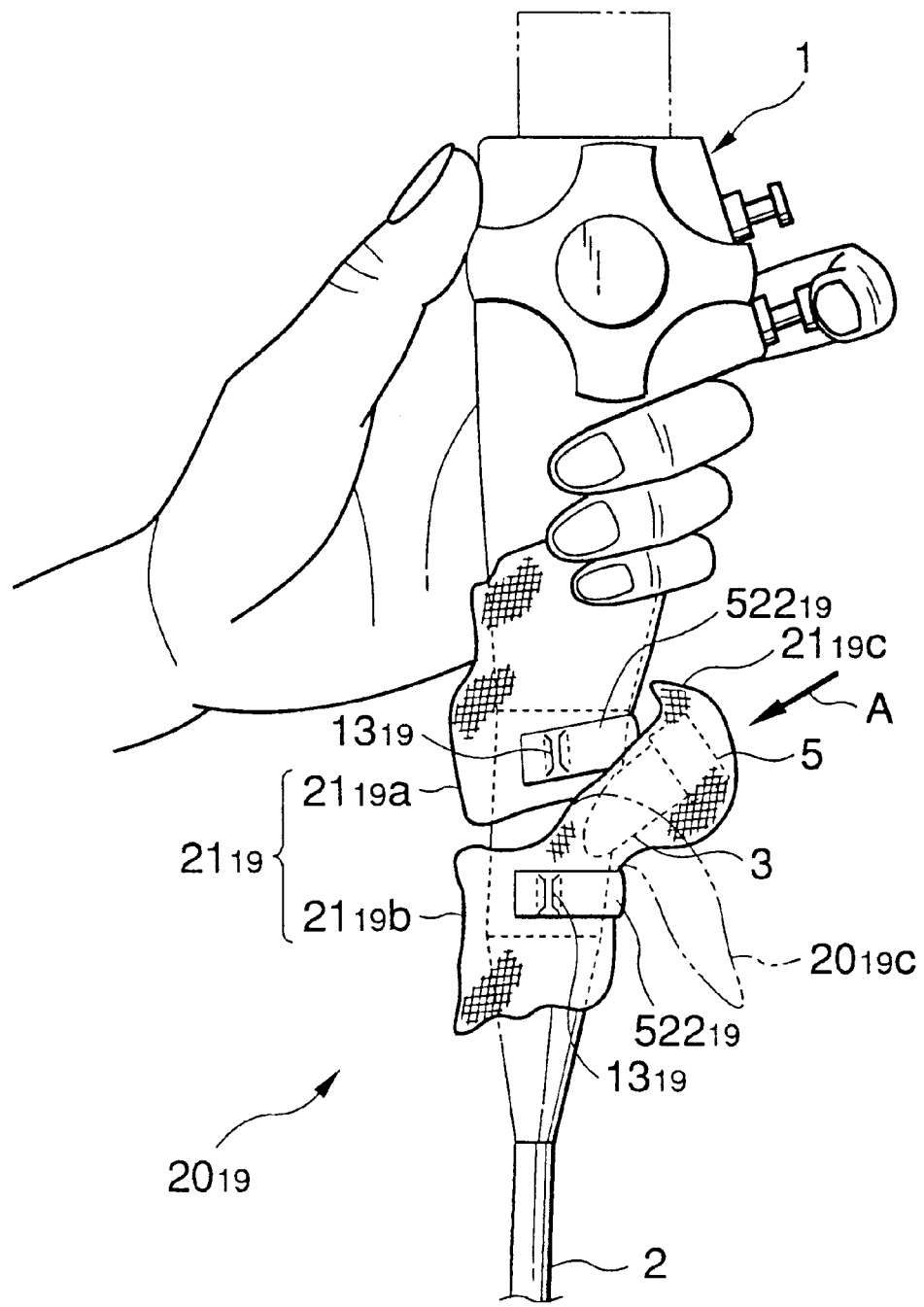
FIG. 47 is a side view of the usage condition in which a foul fluid splashing prevention device of a nineteenth embodiment of the present invention is attached to the manipulating part.

FIG. 47 shows another embodiment in which the foul fluid absorbing member $21_{19}$ is attached to the manipulating part 1 by separate retaining members $522_{19}$.

The foul fluid absorbing member $21_{19}$ includes an upper foul fluid absorbing member $21_{19}a$, that covers the outer wall face of the manipulating part 1 at the upper side in the vicinity of the operative instrument insertion entrance 5, and a lower foul fluid absorbing member $21_{19}b$, that covers the outer wall face of the manipulating part 2 at the lower side in the vicinity of the operative instrument insertion entrance 5.

Both the upper foul fluid absorbing member $21_{19}a$ and the lower foul fluid absorbing member $21_{19}b$ are attached to cover the outer wall face of the manipulating part 1 over an area extending from the front side to the left and right sides.

Each of the upper side foul fluid absorbing member $21_{19}a$ and the lower side foul fluid absorbing member $21_{19}b$ is detachably retained separately and independently on the manipulating part 1 with a retaining member (fastener) $522_{19}$ made of elastic material such as a metal having a spring property and a hard plastic (e.g., nylon, derlin, Teflon, polysulfone and polyimidamide, etc.).

Figure 48:
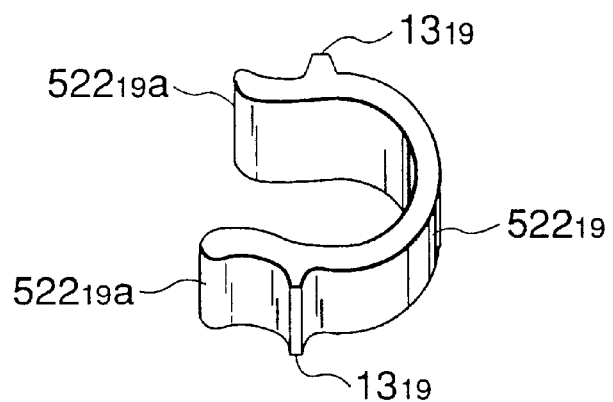
FIG. 48 is a perspective view of a fastener in the nineteenth embodiment of the present invention.
Figure 49:
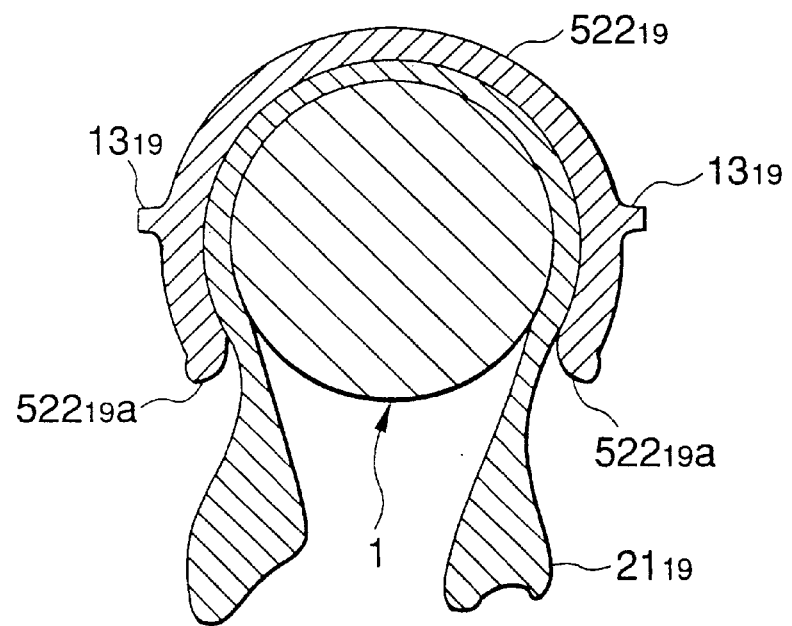
FIG. 49 is a plan sectional view of a portion where the fastener in the nineteenth embodiment of the present invention is mounted on the operating part.

The fastener (retaining member) $522_{19}$ is formed into an almost horseshoe-like shape (or C-shaped) in section as shown in FIG. 48. As shown in FIG. 49, the fastener $522_{19}$ is set into such a geometry as to clamp from the outer wall surface of the manipulating part 1 by its own resiliency with the foul fluid absorbing member $21_{19}$ sandwiched between the outer wall surface of the manipulating part 1 and the fastener $522_{19}$. Both opened edge portions $522_{19}a$ of the fastener are spread smoothly and slightly outward to prevent the foul fluid absorbing member $21_{19}$ from being caught thereby.

A pair of projections $13_{19}$ for finger hooks are protrudingly formed laterally in the halfway portions of the outer surface of the fastener $522_{19}$ so as to facilitate hooking of the finger when the fastener $522_{19}$ is attached to and detached from the manipulating part 1.

Figure 50:
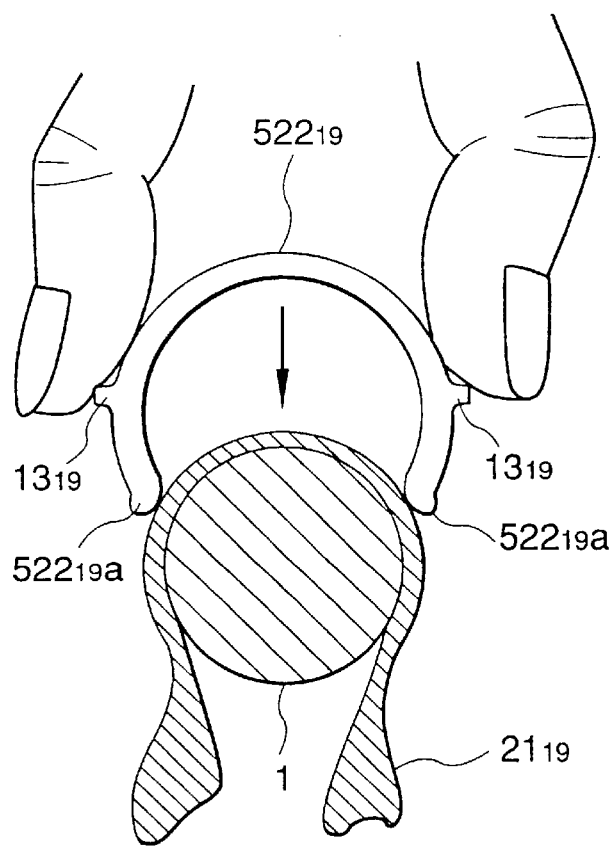
FIG. 50 is a plan view showing with a section part of a state where the fastener in the nineteenth embodiment of the present invention is mounted on the operating part.

When the fastener $522_{19}$ is to be attached, as shown in FIG. 50, while applying the foul fluid absorbing member $21_{19}$ to the outer wall surface of the manipulating part 1, the fastener $522_{19}$ is pressed almost vertically to the axis of the manipulating part 1 from the outside. Then, the fastener $522_{19}$ is subjected to elastic deformation and covers the foul fluid absorbing member $21_{19}$ while expanding. At this time, the fingertips are caught by the protrusions $13_{19}$ and thus are prevented from slipping.

Then, when the fastener $522_{19}$ covers the foul fluid absorbing member $21_{19}$ as shown in FIG. 49, the foul fluid absorbing member $21_{19}$ is pressed inwardly to the outer wall surface of the manipulating part 1 and retained in place by the fastener $522_{19}$ having the resiliency (spring force) to contract to its original shape.

Figure 51:
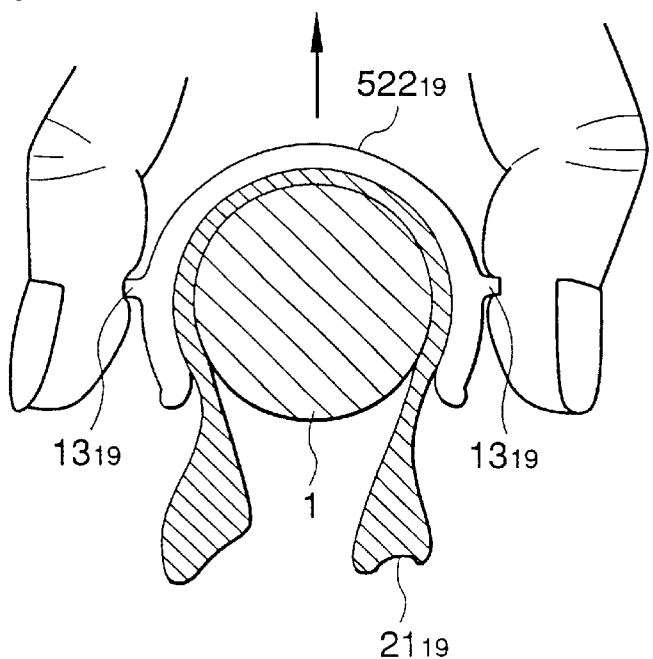
FIG. 51 is a plan view showing with a section part of a state where the fastener in the nineteenth embodiment of the present invention is removed from the operating part.

When the foul fluid absorbing member $21_{19}$ is to be removed, the fastener $522_{19}$ is pulled outward with fingertips hooked on to the protrusions $13_{19}$ as shown in FIG. 51. Then, the fastener $522_{19}$, while being elastically deformed, is removed from the outer wall surface of the manipulating part 1. Thus, the foul fluid absorbing member $21_{19}$ is removed to be replaced with a new one.

Returning to FIG. 47, the upper foul fluid absorbing member $21_{19}a$ is retained by the first fastener $522_{19}$ at a portion of manipulating part 1 immediately above the operative instrument insertion entrance 5 and is extended upwardly so that it can be gripped by the inner side of the operator's hand that grips the manipulating part 1.

Foul fluids that escape from the operative instrument insertion entrance 5 are thus prevented from getting on the hand and the manipulating part 1 is made less slippery and thus easier to hold. The upper foul fluid absorbing member $21_{19}a$ itself can also be held in a stable manner.

Meanwhile, the lower foul fluid absorbing member $21_{19}b$ is retained by the second fastener $522_{19}$ at a portion of the manipulating part 1 immediately below the operative instrument insertion entrance 5 and extends downwardly therefrom. Further, the free end $21_{19}c$, which is positioned above the second fastener $522_{19}$, is placed on top of the operative instrument insertion entrance (5) portion so as to cover this portion.

Thus, even when foul body cavity fluids that have passed through the operative instrument insertion channel escape from the operative instrument insertion entrance 5, most of such fluids can be absorbed by foul fluid absorbing member $21_{19}b$ at the free end $21_{19}c$ and can be prevented from splashing externally or getting on the hands or face of the operator.

The foul fluids that splash or seep upwards from the operative instrument insertion entrance 5 will be absorbed by the upper foul fluid absorbing member $21_{19}a$, thus preventing the hand of the operator that grips manipulating part 1 from getting dirty.

Furthermore, the foul fluids that tend to drip downward from the operative instrument insertion entrance 5 are absorbed by the lower half portion of the lower foul fluid absorbing member $21_{19}b$ and are thus prevented from dripping down further. The bed and the patient's skin will thus be prevented from getting dirty.

To insert the operative instrument via the operative instrument insertion entrance 5, the operative instrument is inserted into the operative instrument insertion entrance 5 as shown by arrow A (FIG. 47) upon withdrawing the free end $21_{19}c$ of the foul fluid absorbing member $21_{19}$ from the operative instrument insertion entrance (5) portion as indicated by two-dotted chain line of FIG. 47.

Figure 52:
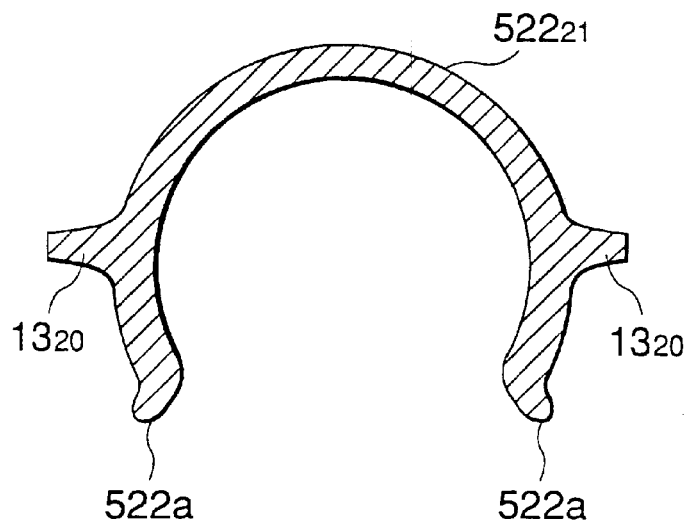
FIG. 52 is a sectional view of a fastener in a twentieth embodiment of the present invention.
Figure 53:
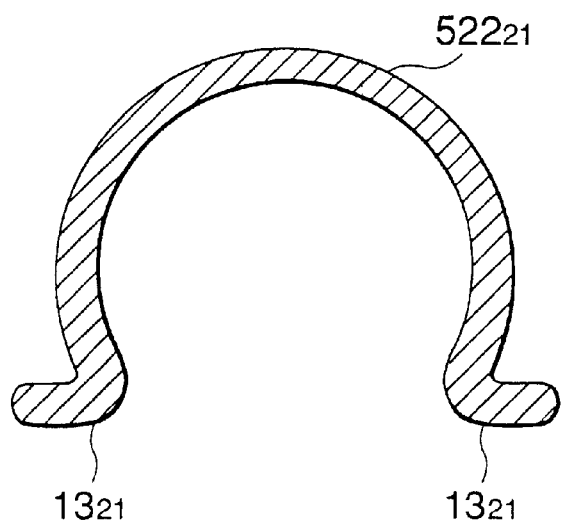
FIG. 53 is a sectional view of a fastener in a twenty-first embodiment of the present invention.

In addition, the free end $21_{19}c$ of the foul fluid absorbing member $21_{19}$ which covers the operative tool insertion entrance (5) portion may be provided on the upper side foul fluid absorbing member $21_{19}a$. Furthermore, the finger hook protrusion of the fastener may be formed to have a large protruded amount as shown in FIG. 52 (a finger hook protrusion $13_{20}$) or the finger hook protrusion may be formed at the opening edge portion of the fastener as shown in FIG. 53 (a finger hook protrusion $13_{21}$).

Figure 54:
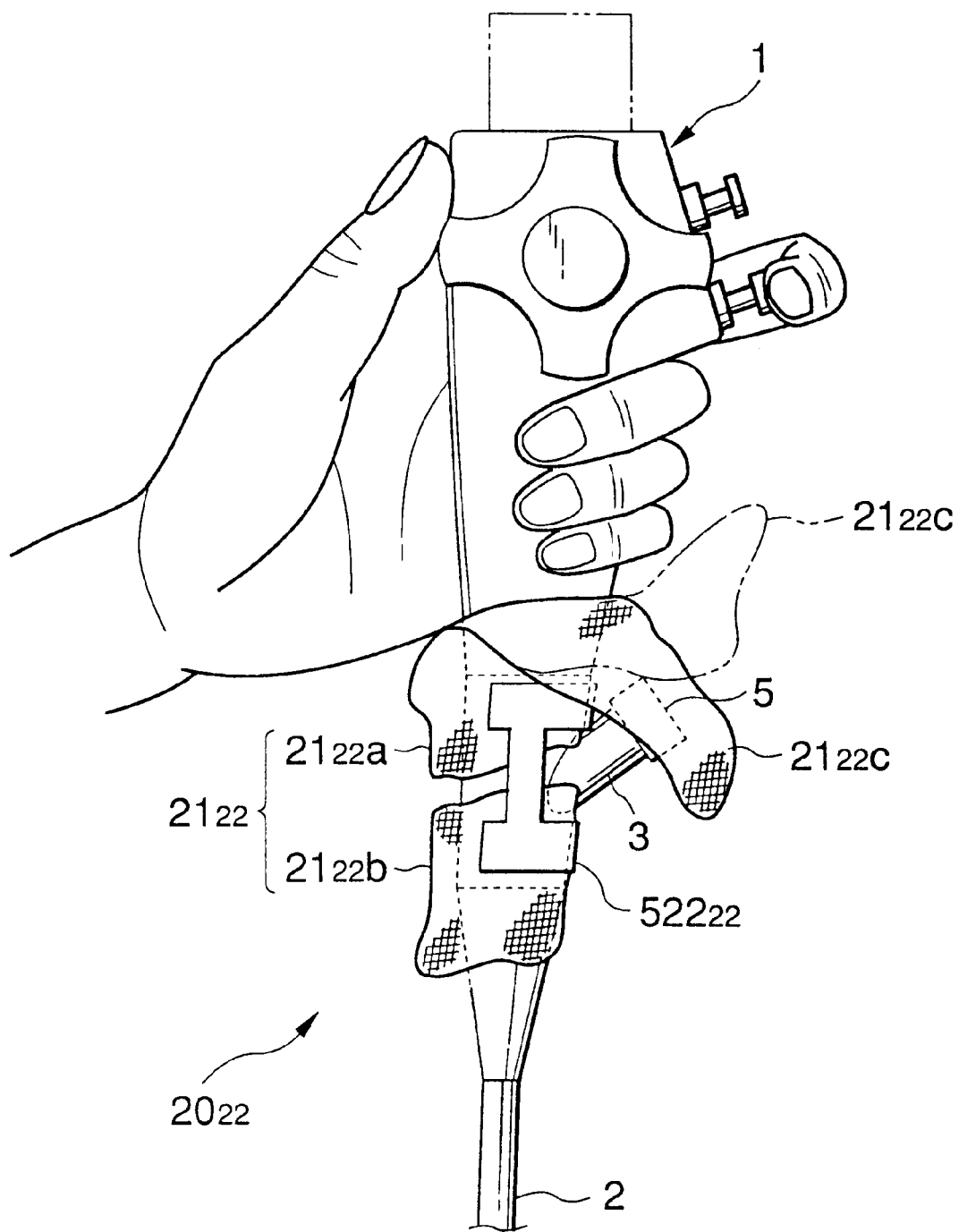
FIG. 54 is a side view of an application state of a fastener in a twenty-second embodiment of the present invention where it is mounted on the manipulating part.

FIG. 54 shows another embodiment of the present invention wherein the upper side foul fluid absorbing member $21_{22}a$ and the lower side foul fluid absorbing member $21_{22}b$ are retained on the manipulating part 1 with a single fastener $522_{22}$.

Figure 55:
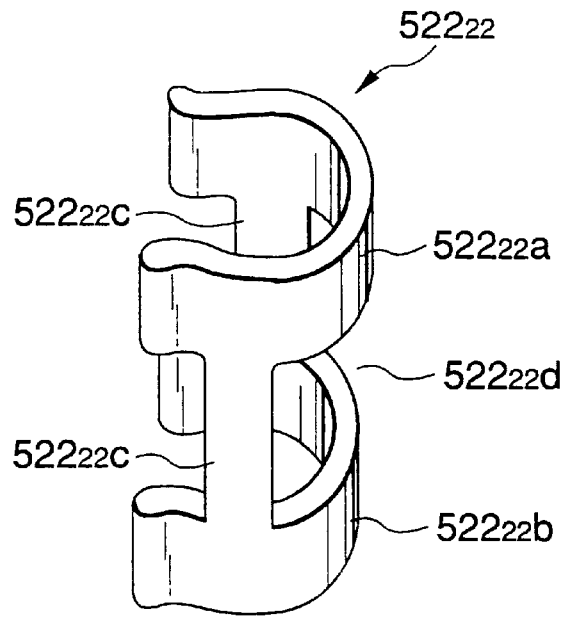
FIG. 55 is a perspective view of the fastener in the twenty-second embodiment of the present invention.

With this fastener $522_{22}$, as shown in FIG. 55, the upper side presser part $522_{22}a$ for pressing the upper side foul fluid absorbing member $21_{22}a$ and the lower side presser part $522_{22}b$ for pressing the lower side foul fluid absorbing member $21_{22}b$ are formed into a shape of a horseshoe-like cross section respectively, both being integrally connected by a pair of right and left slender connecting parts $522_{22}c$.

Among these parts $522_{22}a$, $522_{22}b$, and $522_{22}c$, the opening part $522_{22}d$ through which the protruding part 3 can pass is formed so that the fastener $522_{22}$ may not interfere with the protruding part 3 formed at its end with the operative tool insertion entrance 5.

Thus, since the upper side foul fluid absorbing member $21a$ and the lower side foul fluid absorbing member $21_{22}b$ can be retained on the manipulating part 1 with the single fastener $522_{22}$, only one operation enables the attachment and removal of the fastener $522_{22}$. Thus the handling is made simple.

Figure 56:
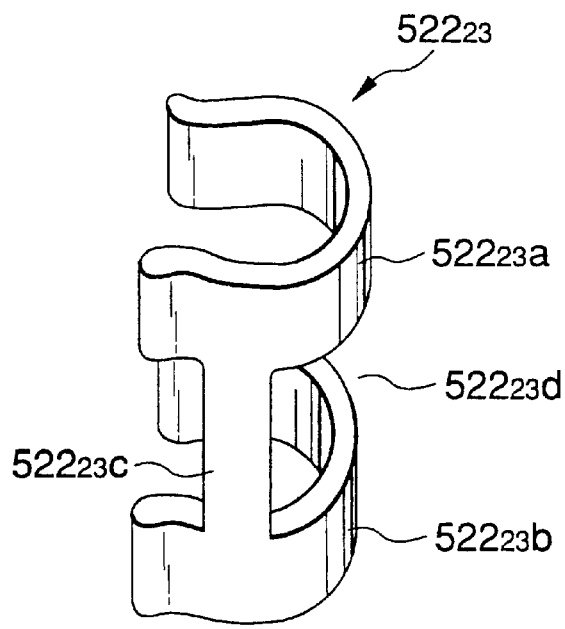
FIG. 56 is a perspective view of a fastener in a twenty-third embodiment of the present invention.

While in this embodiment, the free end $21_{22}c$ of the foul fluid absorbing member $21_{22}$ which covers the operative tool insertion entrance (5) portion is provided on the upper side foul fluid absorbing member $21_{22}a$, the free end of the lower side foul fluid absorbing member $21_{22}b$ may be used. Furthermore, only one connecting part $522_{23}c$ may be provided as in the embodiment shown in FIG. 56.

Figure 57:
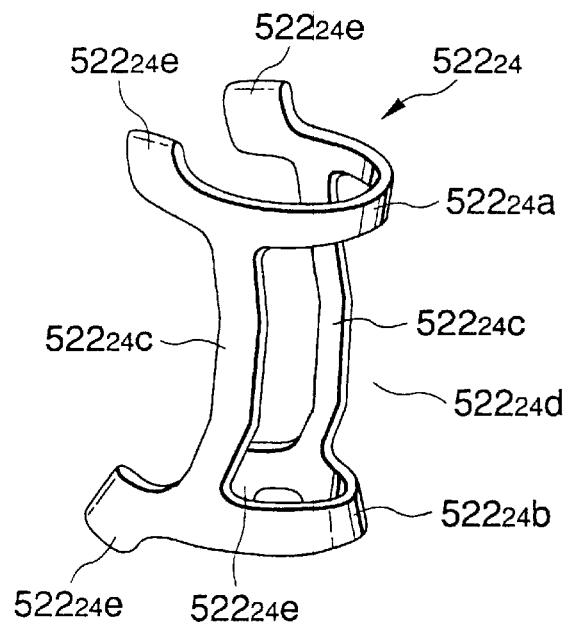
FIG. 57 is a perspective view of the fastener in a twenty-fourth embodiment of the present invention.
Figure 58:
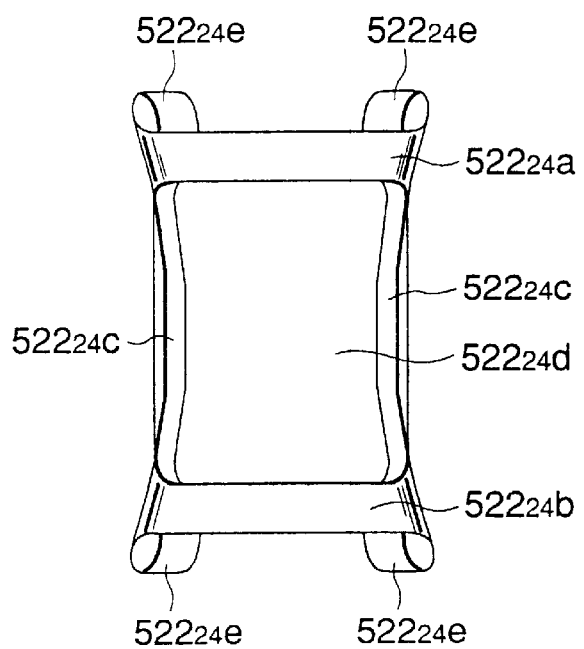
FIG. 58 is a front view of the fastener in the twenty-fourth embodiment of the present invention.
Figure 59:
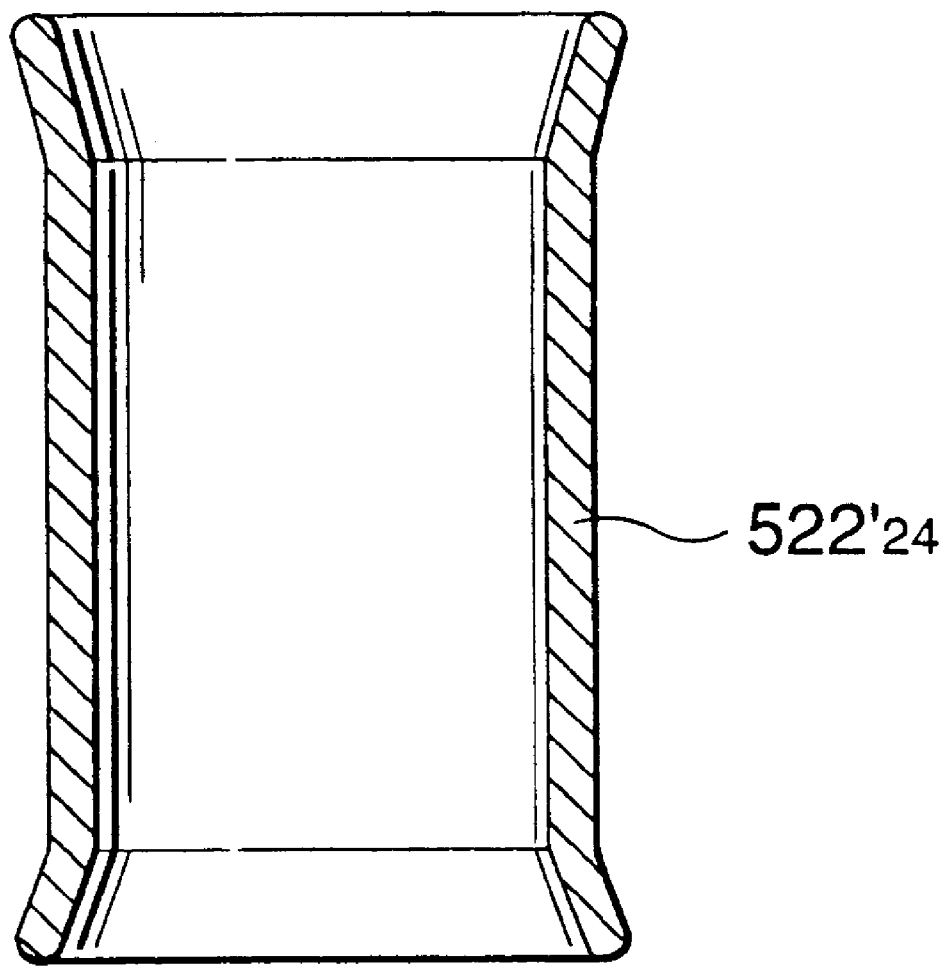
FIG. 59 is a sectional view of a material if the fastener in the twenty-fourth embodiment of the present invention.

FIG. 57 is a perspective view of the fastener $522_{24}$ in another embodiment of the present invention and FIG. 58 is a front view thereof. FIG. 59 is a sectional view of the tube $522_{24}'$ to be used as a material for forming the fastener 522 of this embodiment. The fastener $522_{24}$ of this embodiment is formed by cutting the material tube $522_{24}'$.

While the fastener $522_{24}$ of this embodiment is formed into a shape almost the same as that of the fastener $522_{24}$ shown in FIG. 55, the ear-shaped tab portions $522_{24}e$, to pinch with fingertips during attachment and detachment to and from the manipulating part 1, are formed protrudingly at the both edge portions.

Since both axial ends of the material tube $522_{24}'$ are a funnel-like spreading cylindrical shape, the fastener $522_{24}$ obtained by machining the material tube $522_{24}'$ also has a shape of both ends spreading outward.

As a result, the ear-shaped portions $522_{24}e$ formed at the edges can be pinched easily with fingertips during the attachment and detachment of the fastener $522_{24}$. Furthermore, since the fastener $522_{24}$ is formed symmetrically vertically and laterally (i.e., symmetrical about the axial direction and a direction between which the axis is sandwiched), no restriction is made on the mounting direction with respect to the manipulating part 1.

Figure 60:
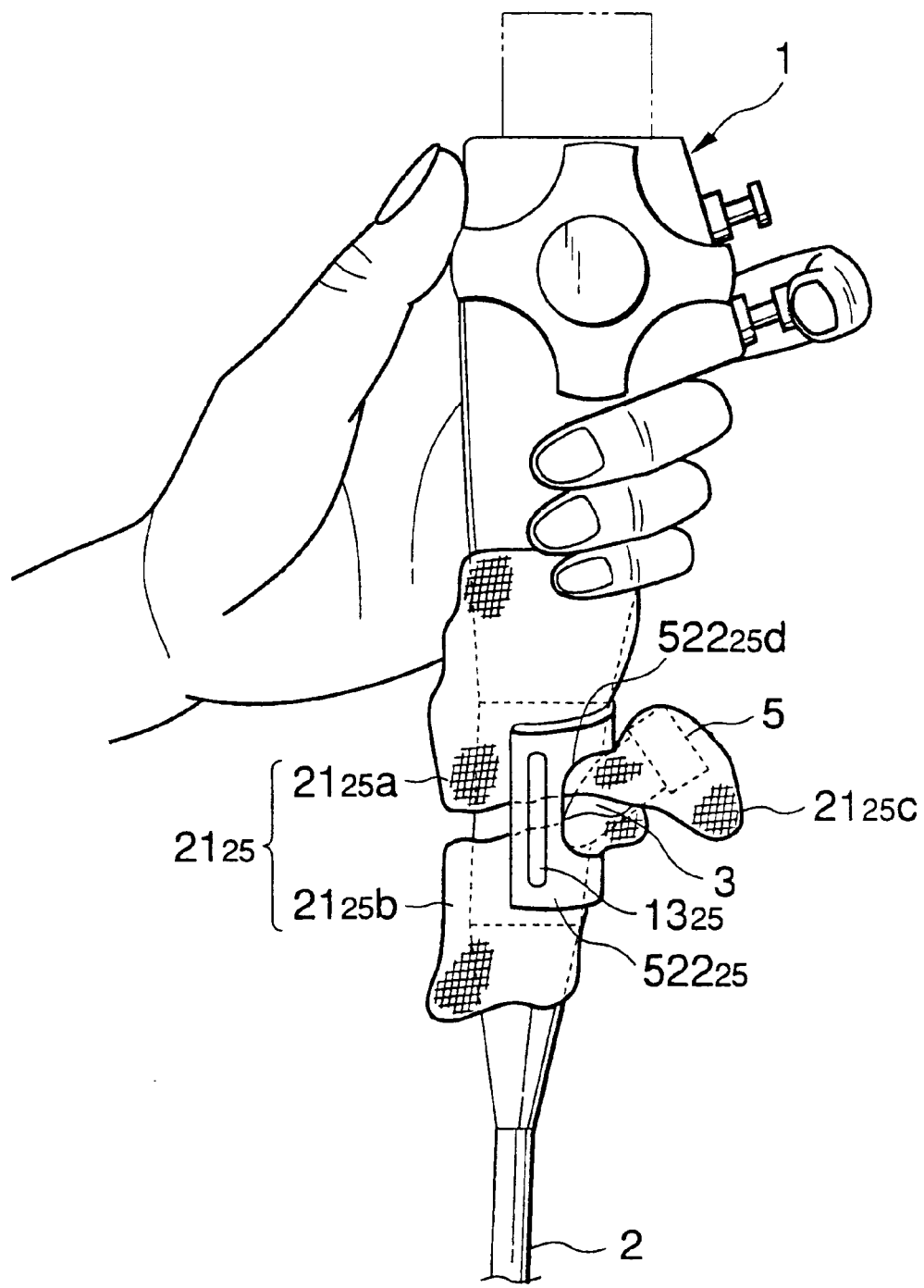
FIG. 60 is a side view of an application state of a fastener in a twenty-fifth embodiment of the present invention where it is mounted on the manipulating part.

FIG. 60 shows another embodiment of the present invention, which is the same with the embodiment shown in FIG. 55, in that the upper side foul fluid absorbing member and the lower side foul fluid member can be retained on the manipulating part 1 with the single fastener.

Figure 61:
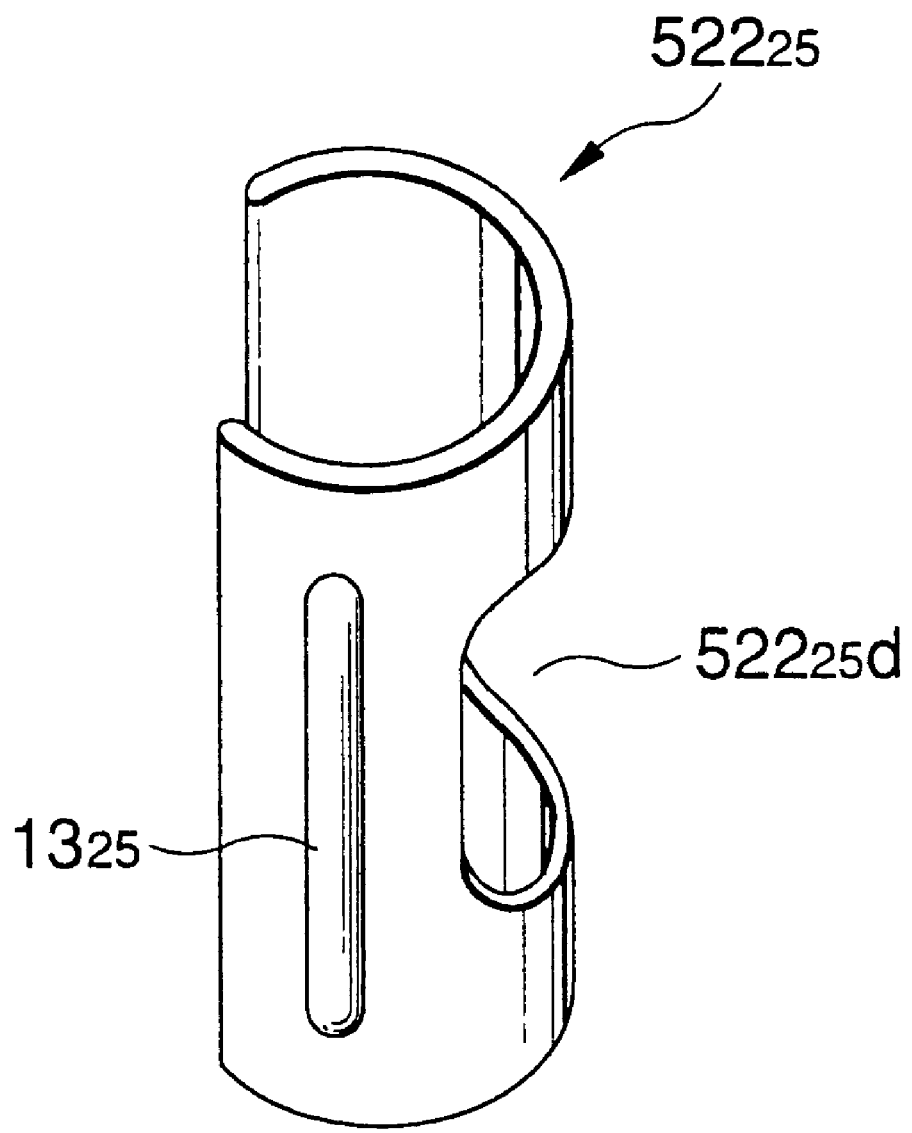
FIG. 61 is a perspective view of the fastener in the twenty-fifth embodiment of the present invention.

In this embodiment, as shown in FIG. 61, the opening portion $522_{25}d$ for passing the protruding portion 3 is bored in the central portion of the cylindrical fastener $522_{25}$ formed into a horseshoe shape in section. Numeral $13_{25}$ designates the finger hook protrusion.

Figure 62:
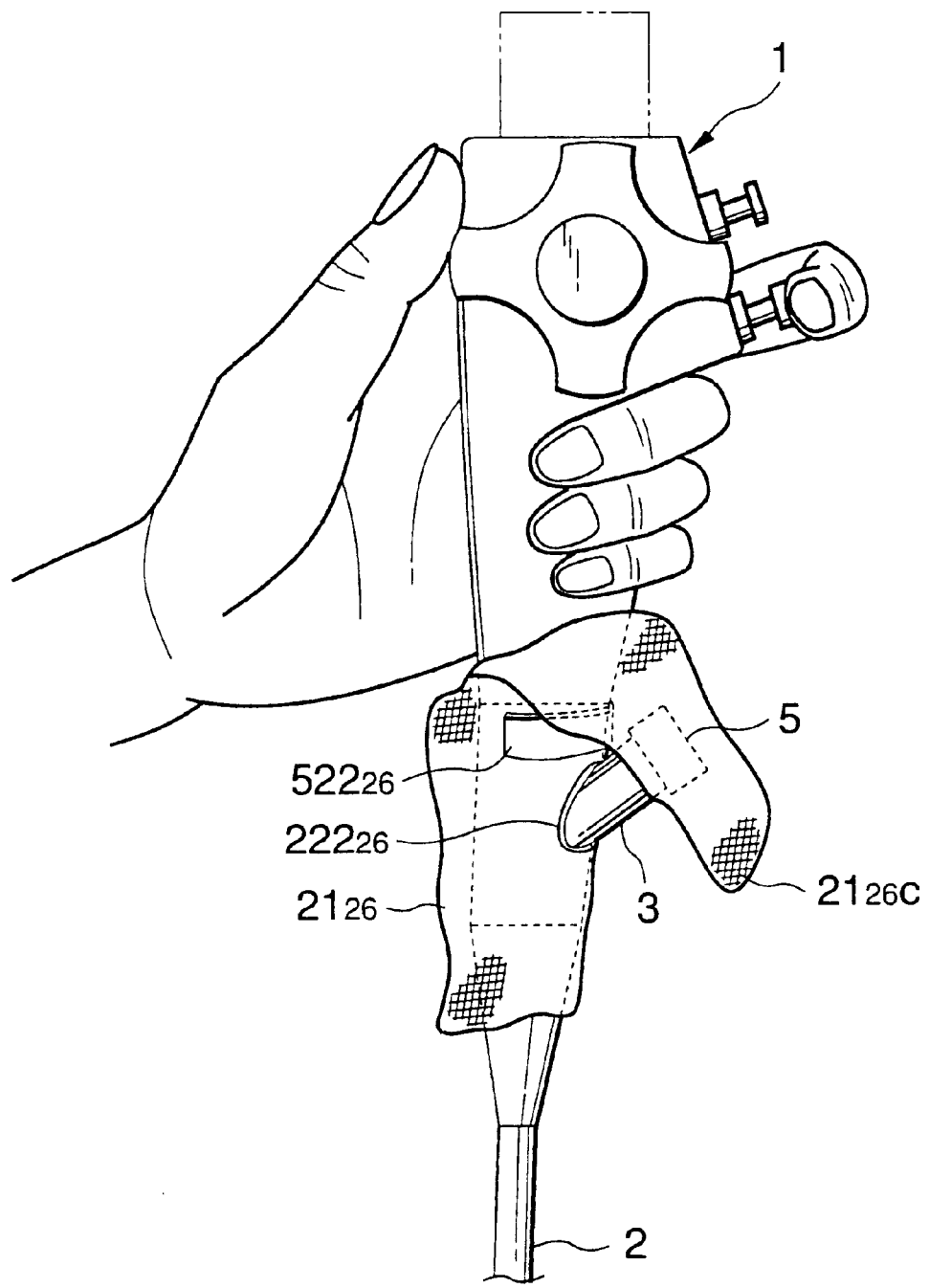
FIG. 62 is a side view of the usage condition in which a foul fluid splashing prevention device of a twenty-sixth embodiment of the present invention is attached to the manipulating part.

FIG. 62 shows another embodiment of the present invention in which the fastener shown in FIG. 48 is used in combination with the foul fluid absorbing member shown in FIG. 28. A hole $222_{26}$ is opened in the central portion to permit the protrusion 3 of the manipulating part 1 to pass therethrough.

Although in FIG. 62, the upper free end is used as free end $21_{26}c$ of the foul fluid absorbing member $21_{26}$ for covering the operative instrument insertion entrance 5, the lower free end may be used instead. Also, although just one retaining member $522_{26}$ is attached at the upper side with respect to the operative instrument insertion entrance 5, a plurality of retaining members (fasteners) may be attached thereto.

Pressure-sensitive adhesive agents may also be used as a means for retaining a foul fluid absorbing member $21_{26}$ in the embodiment shown in FIG. 62, onto manipulating part 1.

The foul fluid splashing preventive device according to the present invention can be applied to an endoscope insertion guiding device such as a sliding tube.

Figure 65:
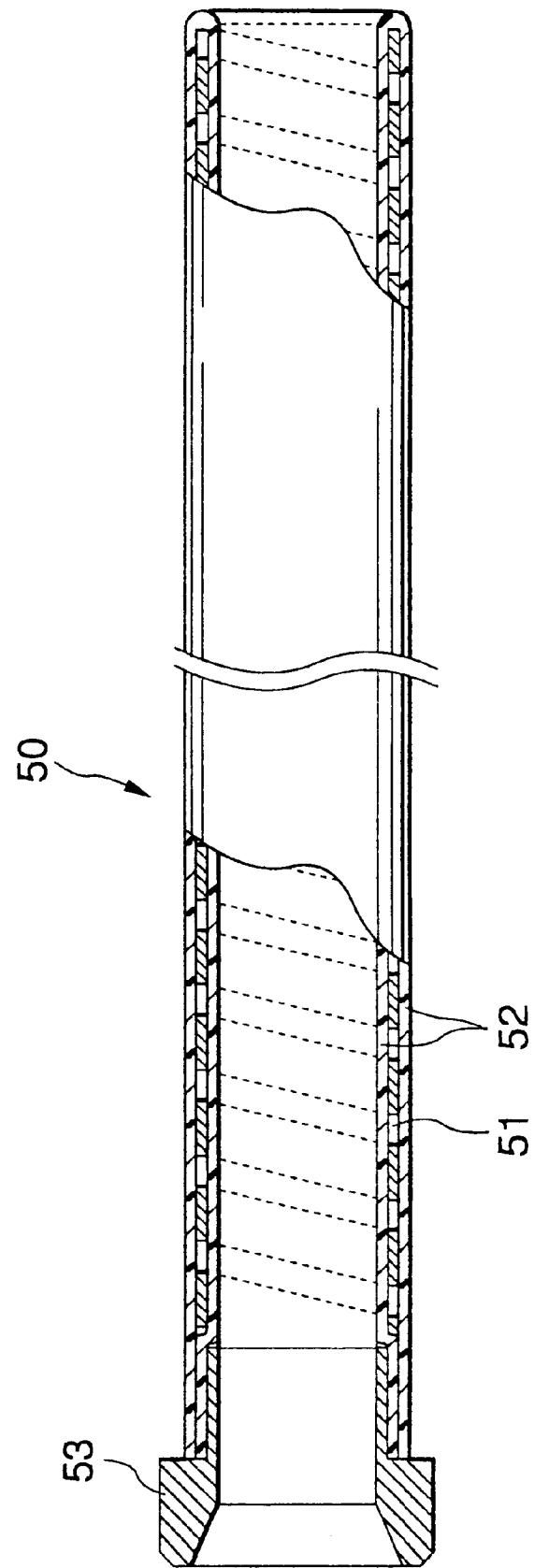
FIG. 65 is a sectional side view of the sliding tube.

FIG. 65 shows a sliding tube 50 used as an endoscope insertion guiding device. The sliding tube 50 is made up of a pipe-like member having a relatively simple construction with some flexibility and a length of about 40 cm. A proximal mouthpiece 53 is mounted to the proximal end portion of the sliding tube 50.

The flexible pipe-like portion is formed such that a flexible sheath or coat 52 closely contacts both the inner and outer surfaces of a spiral tube 51 formed for example by winding a stainless steel web into a spiral manner at intervals with a fixed diameter.

Figure 66:
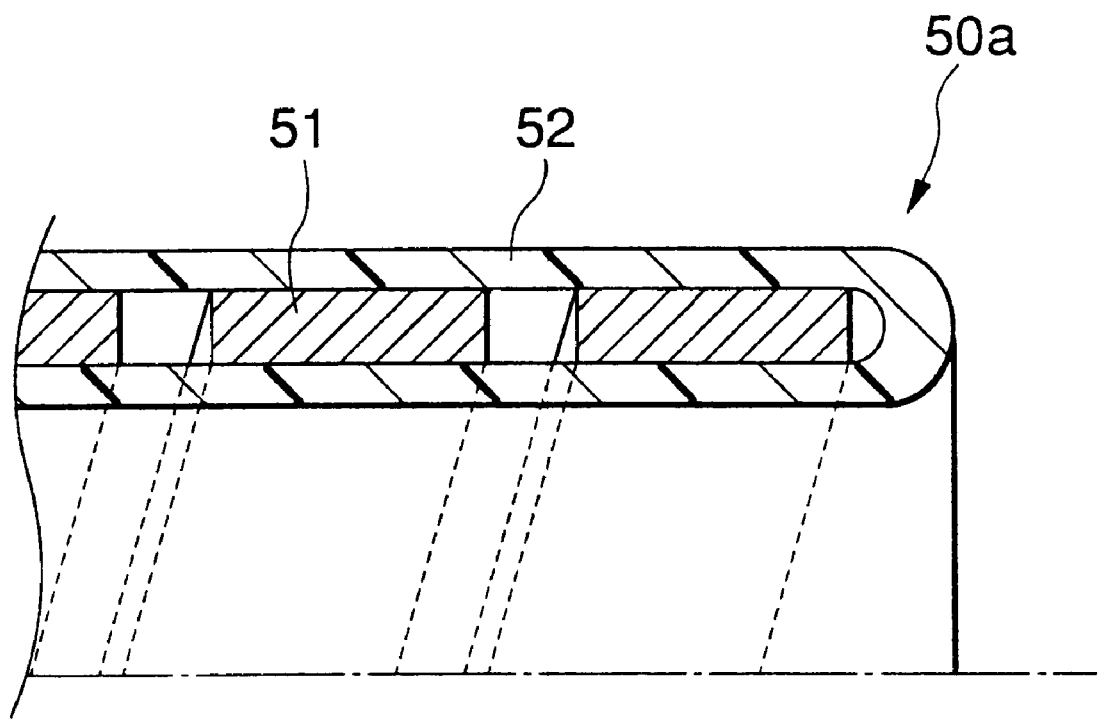
FIG. 66 is a partially enlarged sectional side view of the sliding tube.

Flexible sheath 52 is formed from a flexible tube such as a polyurethane resin tube. As illustrated in an enlarged manner in FIG. 66, a single tube is folded at a front end portion 50a.

The proximal mouthpiece 53 is made of metal or hard plastic, and a hole that is in alignment with and in communication with the inner diameter part of flexible sheath 52 is bored through the proximal mouthpiece 53 in the axial direction.

In order to prevent the entire sliding pipe from entering into the anus during use, the diameter of proximal mouthpiece 53 is made somewhat larger than the outer diameter of the flexible pipe-like portion fitted with flexible sheath 52.

Figure 63:
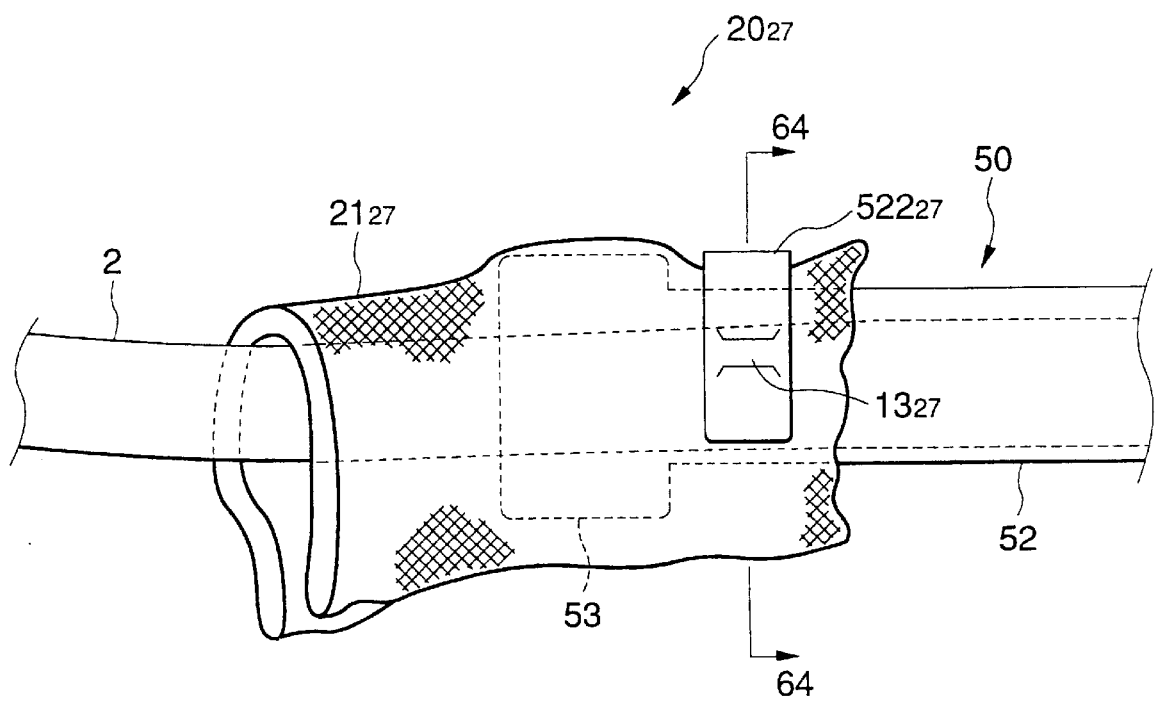
FIG. 63 is a side view which shows the usage condition in which a embodiment of the present invention of a twenty-seventh embodiment of the present invention is attached to the sliding tube.

FIG. 63 shows the manner in which a foul fluid absorbing member $21_{27}$, formed from water-absorbing material to absorb the foul fluids that escape from the anus, is detachably attached to the outer peripheral portion of the proximal mouthpiece 53.

The foul fluid absorbing member $21_{27}$, made for example by overlapping flexible, gauze-like material shaped to have a rectangular form, is attached to the proximal mouthpiece 53 by means of a fastener (retaining member) $522_{27}$ which is attached to the outer surface of flexible sheath 52 adjacent the proximal mouthpiece 53. The foul fluid absorbing member $21_{27}$ thus retained by the fastener $522_{27}$ covers and surrounds the periphery of proximal mouthpiece 53 and the adjacent flexible sheath 52 as well as extends beyond the proximal end.

A pair of finger hook protrusions $13_{27}$ protrude in the diametrical opposite direction from the outer surface of the fastener $522_{27}$.

Figure 64:
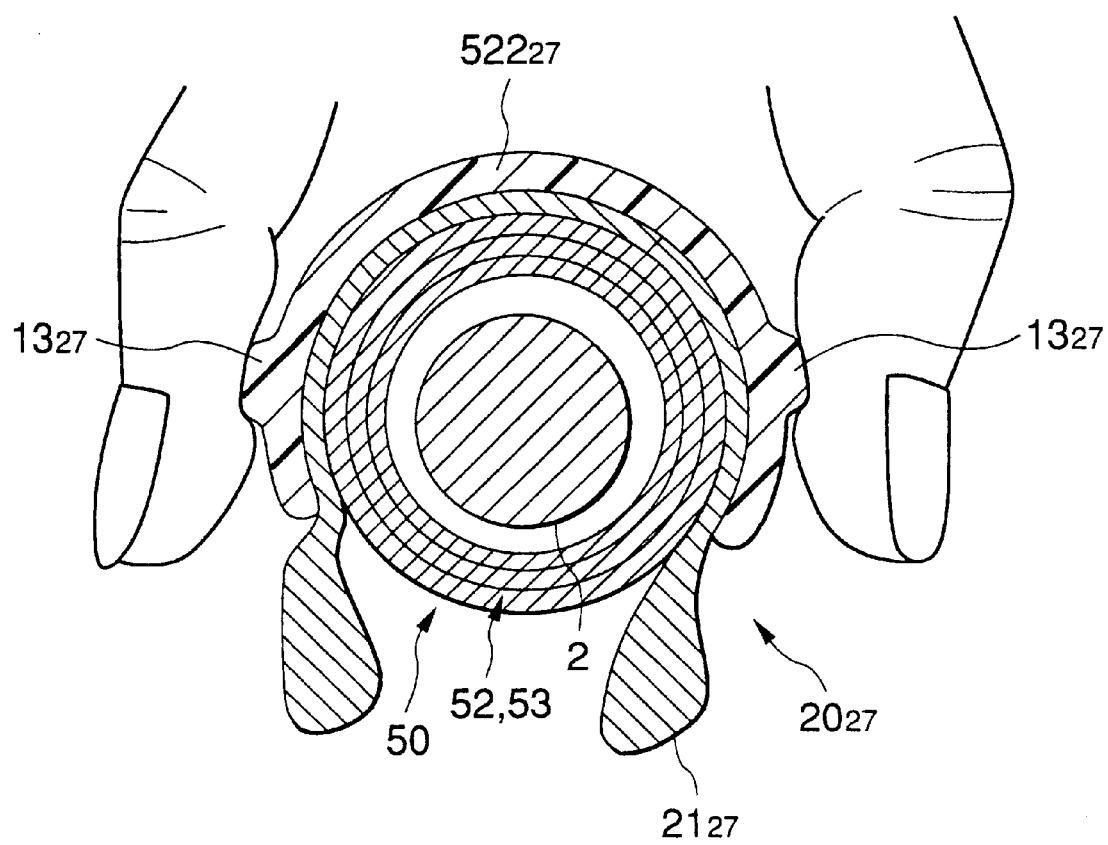
FIG. 64 is a cross sectional view taken along line 64—64 of FIG. 63.

FIG. 64 is a sectional front view of the part where foul fluid absorbing member $21_{27}$ is retained on the sliding tube 50. The fastener $522_{27}$ is fixed by its own resilience in such a manner as to clamp the outer wall face of flexible sheath 52 radially inwardly while sandwiching the foul fluid absorbing member $21_{27}$ between itself and the outer wall face of the flexible sheath 52 of the sliding tube 50.

Figure 67:
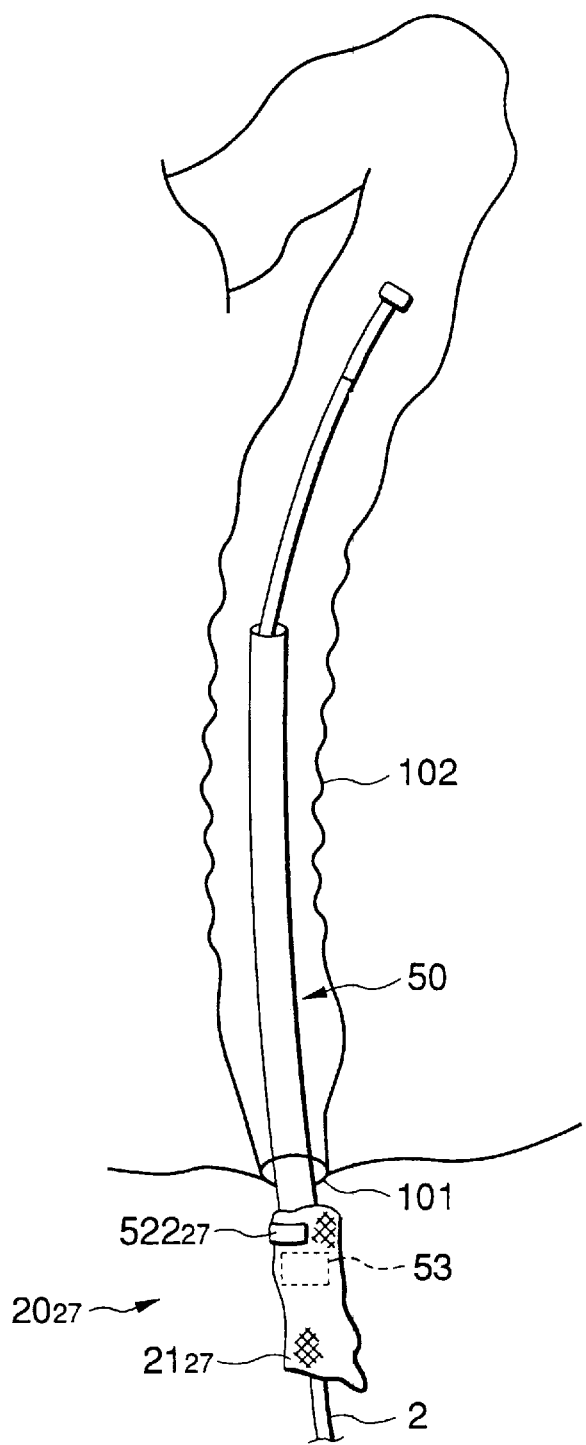
FIG. 67 is a schematic view which shows the usage condition of the twenty-seventh embodiment of the present invention.

FIG. 67 shows the usage condition of the sliding tube 50. As shown therein, after bringing sliding tube 50 to the condition where it straightens the colon (102) portion while leaving just the proximal mouthpiece (53) portion outside the anus 101, the inserted endoscope part 2 that has been inserted through the sliding tube 50 is gradually pushed in deeper while being pushed and pulled.

Figure 87:
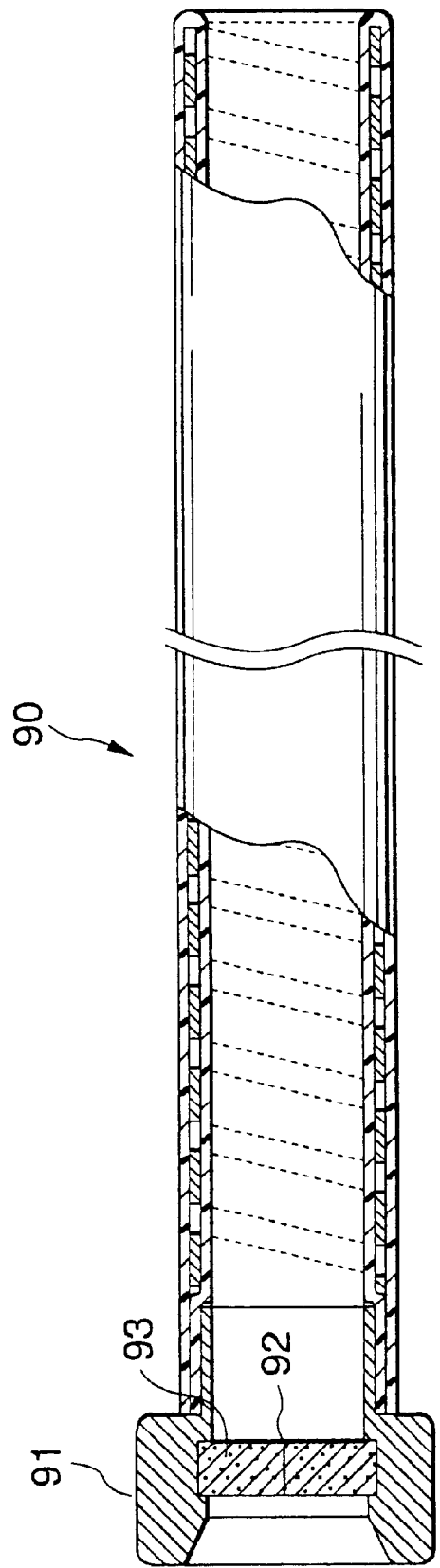
FIG. 87 is a sectional side view of an example of sliding tube.
Figure 88:
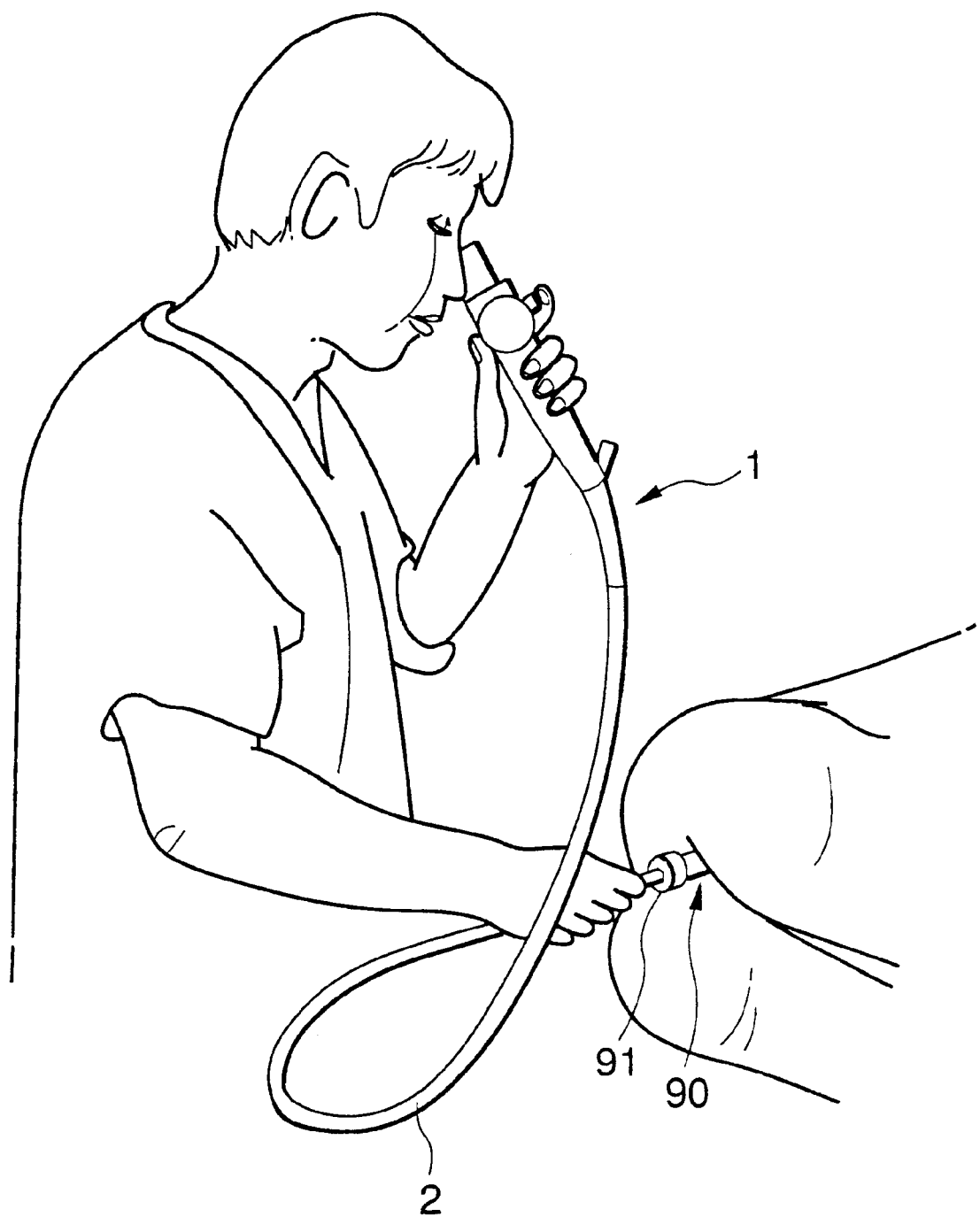
FIG. 88 is a perspective view which shows the usage condition of the sliding tube.
Figure 89:
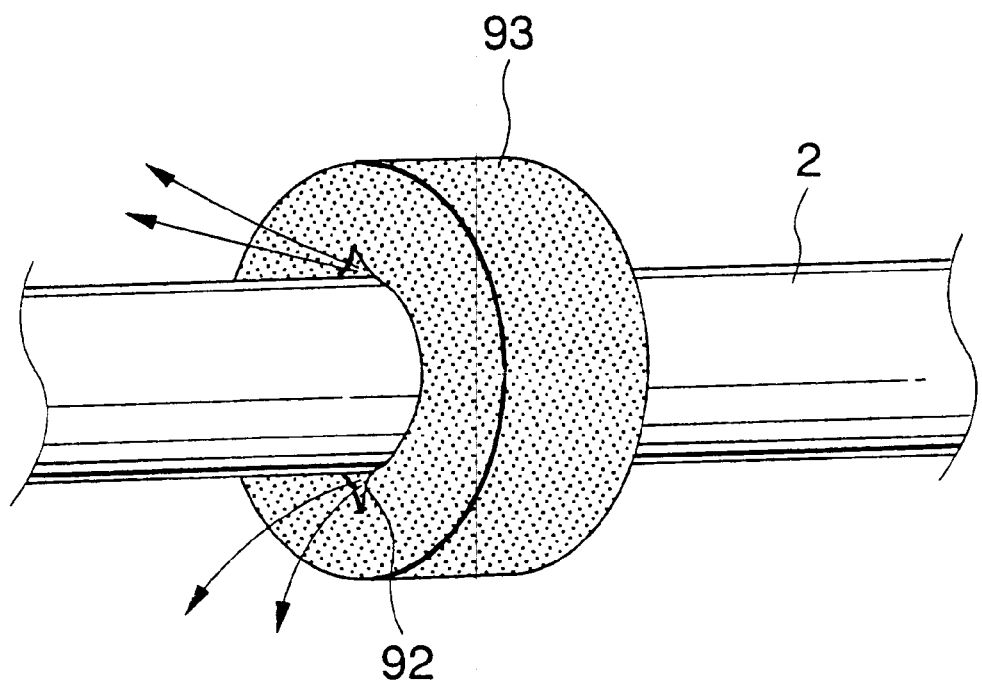
FIG. 89 is a perspective view which shows the condition in which air and foul fluids escape from the sponge member portion of the sliding tube.

A sponge member is not disposed inside the proximal mouthpiece 53 of sliding tube 50 as in the previously explained case (FIG. 87). Thus, when air is to be blown out from inside of the large intestine, it is blown out from the gap between the sliding tube 50 and the inserted part 2 that has been inserted through the sliding tube 50.

In that case, since the opened mouth of the proximal mouthpiece 53 and the periphery of the inserted art 2 adjacent the opened mouth are surrounded by the foul fluid absorbing member $21_{27}$ and cannot splash therefrom.

Further, since the outer peripheral surface of inserted part 2 can be wiped with the foul fluid absorbing member $21_{27}$ when the inserted part 2 is pulled out from the inside of the sliding tube 50 after completion of endoscopy, the operator's hands can be prevented from getting soiled with feces.

Furthermore, since the outer peripheral surface of the inserted part 2 can also be wiped with the foul fluid absorbing member $21_{27}$ when the inserted part 2 is pulled out from the inside of the sliding tube 50 after completion of endoscopy, the operator's hands can be prevented from getting soiled with feces.

Figure 68:
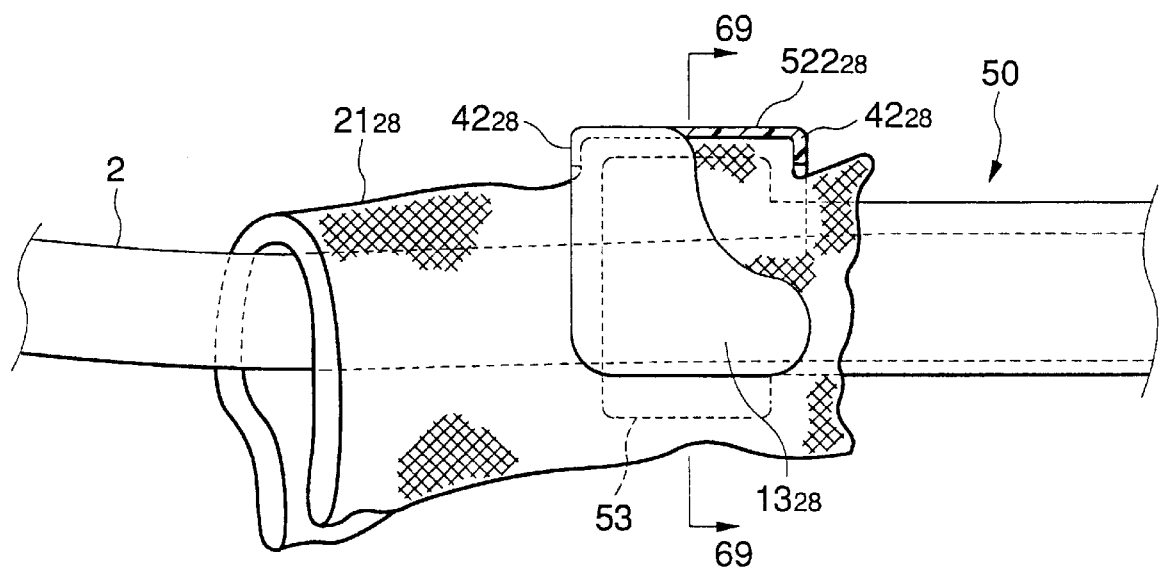
FIG. 68 is a side view which shows the usage condition in which a foul fluid splashing prevention device of a twenty-eighth embodiment of the present invention is attached to the sliding tube.

FIG. 68 shows another embodiment of the present invention in which a fastener $522_{28}$ is fixed and retained onto the proximal mouthpiece 53 of the sliding tube 50 to retain the foul fluid absorbing member $21_{28}$ in place.

Figure 69:
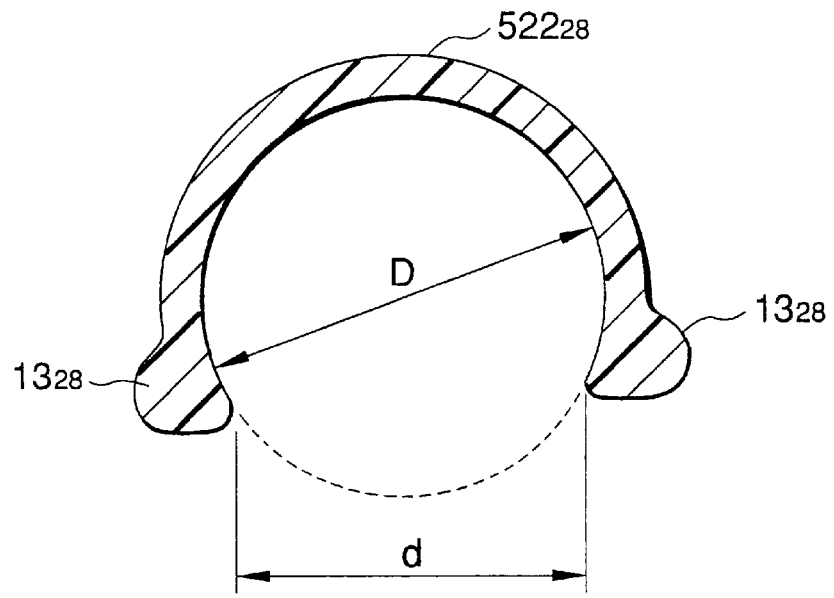
FIG. 69 is a cross sectional view taken along line 69—69 of FIG. 68.

The fastener $522_{28}$ is formed from metal or hard plastic, having spring-like property into a horseshoe-like (or C-like) shape with an opening width d that is smaller than a diameter D (d<D) as shown in FIG. 69. The fastener $522_{28}$ is fixed and retained in such a manner as to clamp the outer wall face of the proximal mouthpiece 53 radially inwardly by its own resilience while sandwiching the foul fluid absorbing member $21_{28}$ between itself and the outer wall face of the proximal mouthpiece 53.

Collar-like stopper protrusions $42_{28}$, which come in contact with the end faces of the proximal mouthpiece 53 in the condition where the foul fluid absorbing member $21_{28}$ is sandwiched therebetween, are protruded inwards at the front and rear axial ends of the fastener $522_{28}$. The movement of the fastener $522_{28}$ in the axial direction is restricted by these stopper protrusions $42_{28}$.

Figure 70:
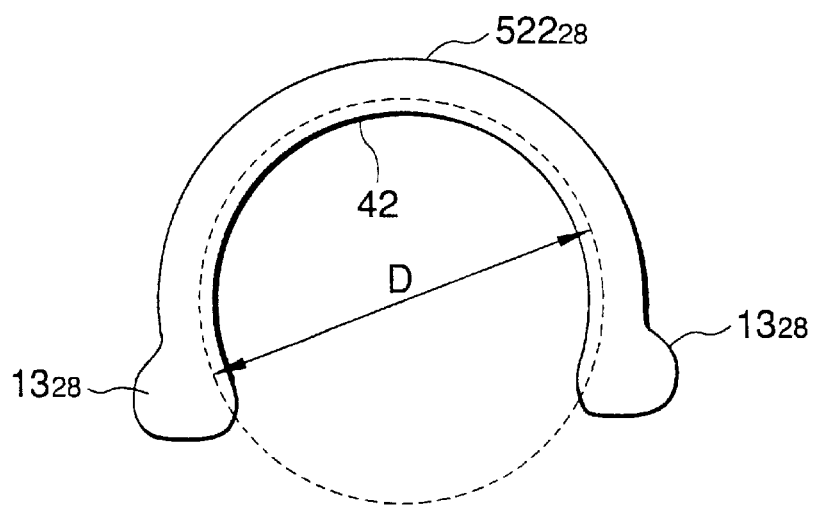
FIG. 70 is a front view of the fastener in the twenty-eighth embodiment of the present invention.

FIG. 70 is a front view of the fastener $225_{28}$, and the portion that protrudes inwards from the broken line is the stopper protrusion $42_{28}$. The finger hook protrusions $13_{28}$ protrude from the outer faces of the ends of the horseshoe-shaped cross section.

Figure 71:
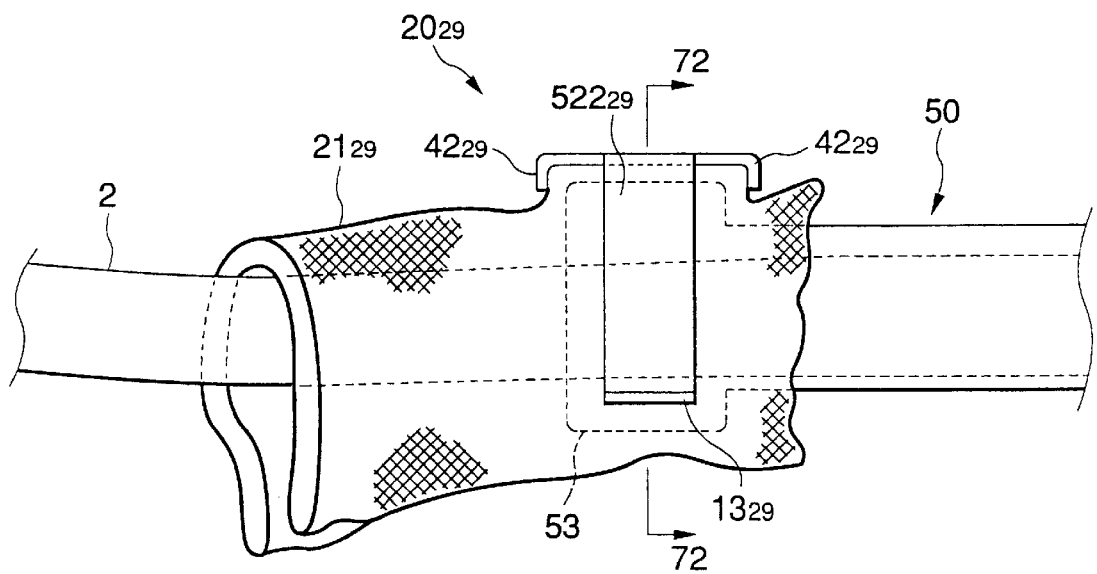
FIG. 71 is a side view which shows that usage condition in which a foul fluid splashing prevention device of a twenty-ninth embodiment of the present invention is attached to the sliding tube.

FIG. 71 shows another embodiment of the present invention in which, as in the embodiment shown in FIG. 68, a fastener $522_{29}$ is fixed to the proximal mouthpiece 53 of the sliding tube 50 to retain the foul fluid absorbing member $21_{29}$ in place.

Figure 72:
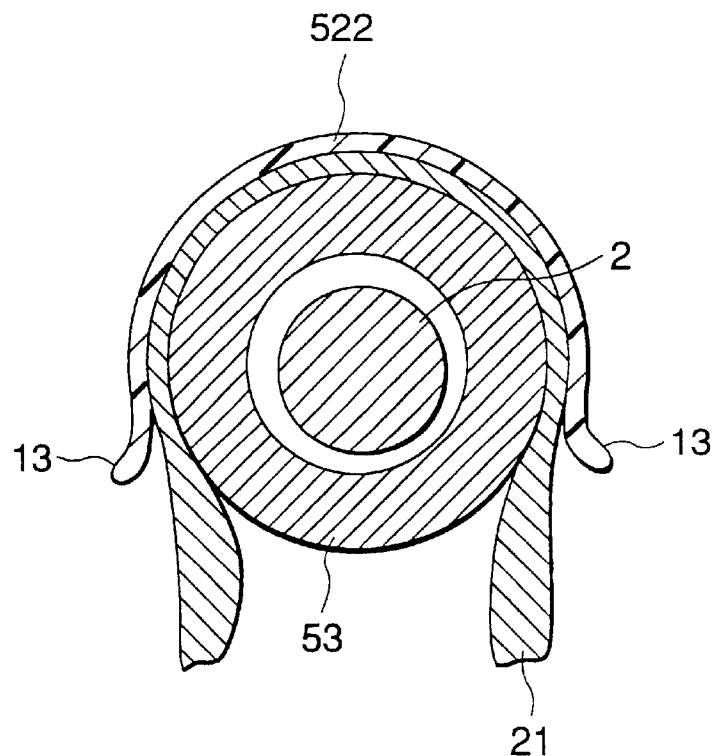
FIG. 72 is a cross sectional view taken along line 72—72 of FIG. 71.
Figure 73:
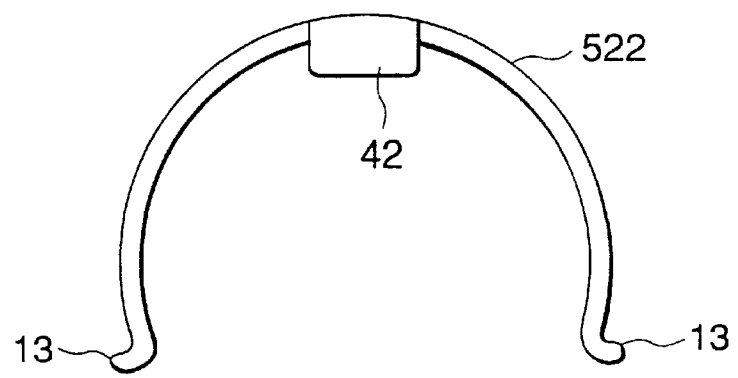
FIG. 73 is a front view of the fastener in the twenty-ninth embodiment of the present invention.

As shown by the cross sectional view (FIG. 72) and by the front view (FIG. 73), the fastener $522_{29}$ is formed to have a horseshoe-like cross-sectional shape and is fixed and retained in such a manner as to clamp the outer wall face of the proximal mouthpiece 53 radially inwardly while sandwiching the foul fluid absorbing member $21_{29}$ between itself and the outer wall face of proximal mouthpiece 53.

However, the length of the fastener $522_{29}$ in the axial direction is made shorter than the proximal mouthpiece 53. The stopper protrusions $42_{29}$, with a hook-like form, extend from the front and rear sides of the fastener $522_{29}$. The end portions of the stopper protrusions $42_{29}$ protrude inwards and these portions contact the front and rear ends of the proximal mouthpiece 53 to restrict the movement of fastener $225_{29}$ in the axial direction.

Figure 74:
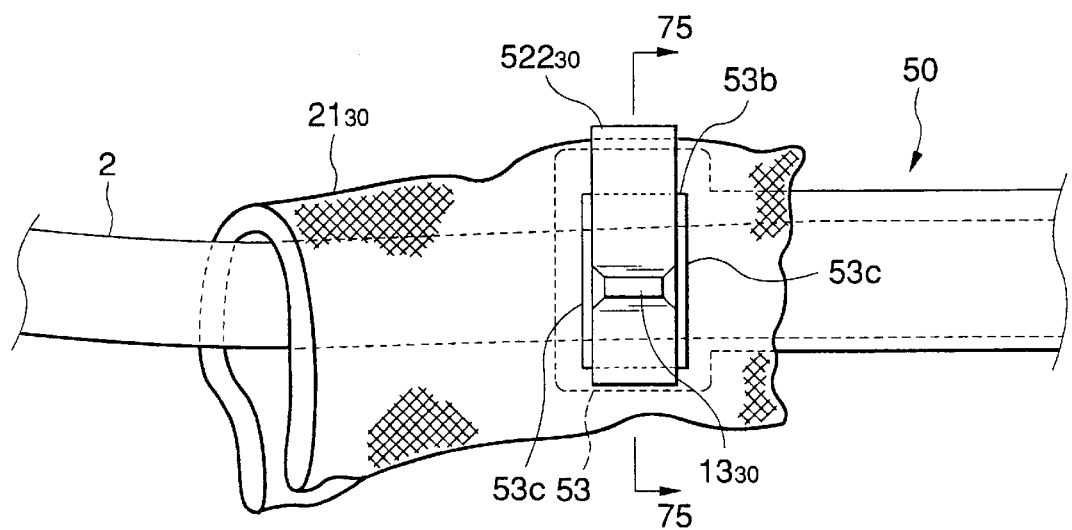
FIG. 74 is a side view which shows the usage condition in which a foul fluid splashing prevention device of the thirtieth embodiment of the present invention is attached to the sliding tube.

FIG. 74 shows another embodiment of the present invention. As shown by the cross sectional view (FIG. 75), flat parts 53b are formed at both side faces of the middle portion of the proximal mouthpiece 53 of the sliding tube 50, and the fastener $522_{30}$ is formed to have horseshoe-like shape having linear parts at the left and right sides in correspondence with the flat pats 53b. The fastener $522_{30}$ is formed from material having a spring-like property.

The movement of the fastener $225_{30}$ in the axial direction is restricted since the flat parts 53b are formed only on the middle portion of the outer face o the proximal mouthpiece 53 and the fastener $522_{30}$ comes in contact with step parts 53c on the proximal mouthpiece 13 when it is moves in the axial direction.

Figure 75:
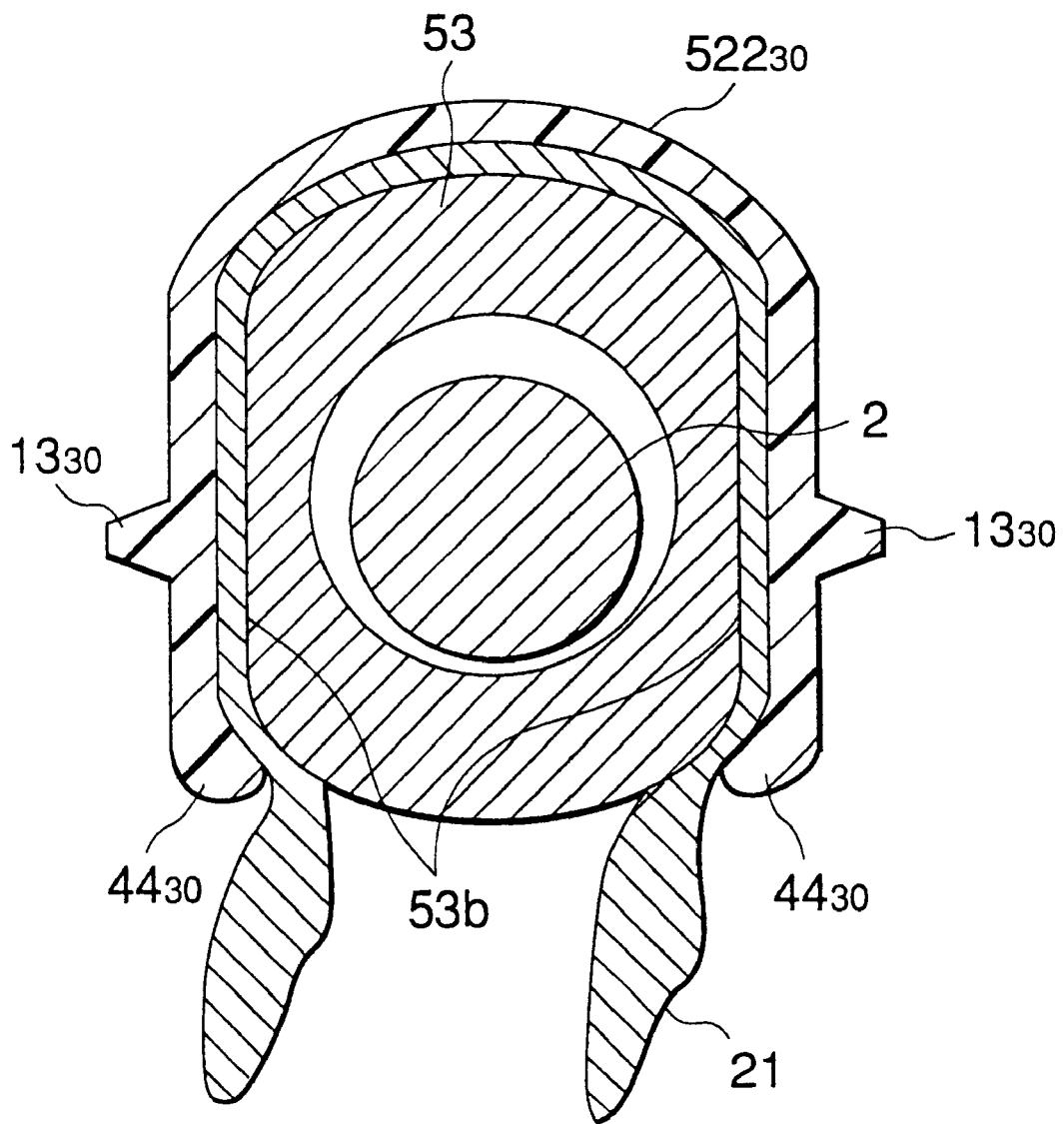
FIG. 75 is a cross sectional view taken along line 75—75 of FIG. 74.

As shown in FIG. 75, the end portions $44_{30}$ of the fastener $522_{30}$ are bent slightly inwards to enable secure engagement with the proximal mouthpiece 53. Reference numeral $13_{30}$ designates a finger hook protrusion. The finger hook protrusion can be dispensed with.

Figure 76:
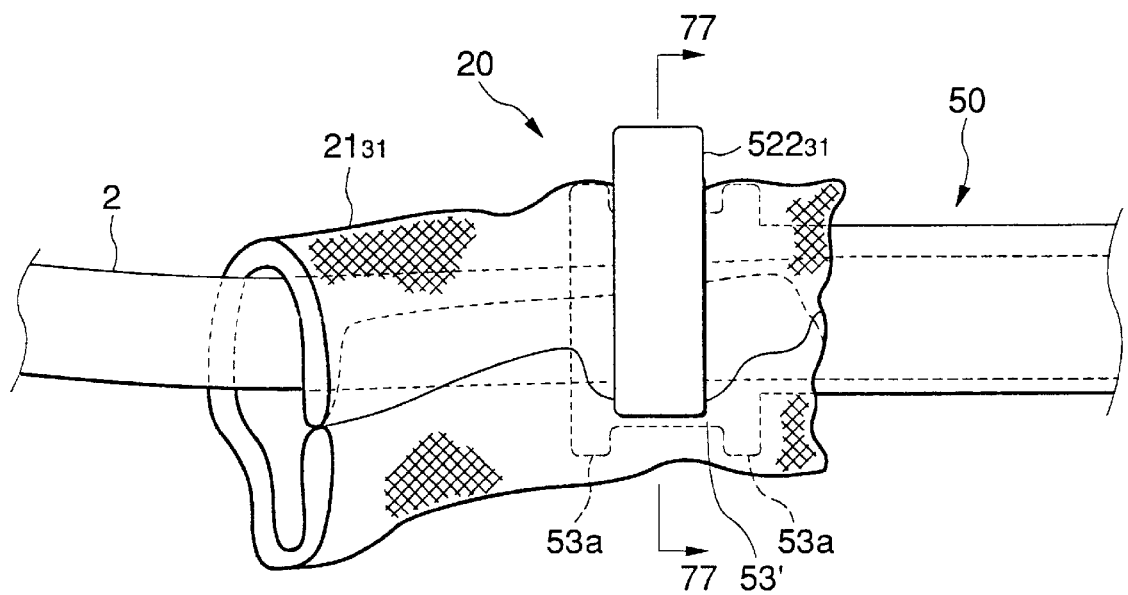
FIG. 76 is a side view which shows the usage condition in which a foul fluid splashing prevention device of a thirty-first embodiment of the present invention is attached to the sliding tube.
Figure 77:
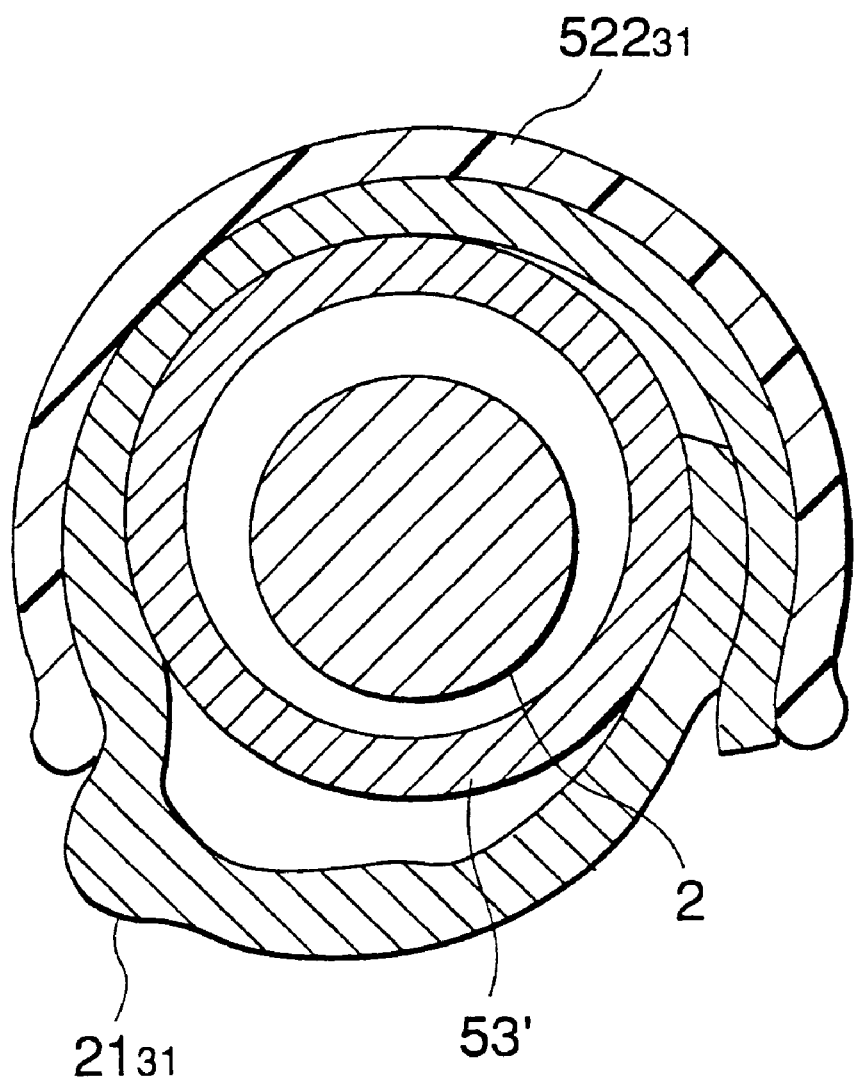
FIG. 77 is a cross sectional view taken along line 77—77 of FIG. 76.

FIG. 76 shows another embodiment of the present invention in which a pair of flanges 53a, which are space din the axial direction, protrude from the proximal mouthpiece 53' of the sliding tube 50 and the fastener $522_{31}$ is attached between these flanges 53a. The movement of the fastener $522_{31}$ in the axial direction is thus restricted by flanges 13a. FIG. 77 shows the cross section along line 77—77 of FIG. 76. In this embodiment, the foul fluid absorbing member $21_{31}$ is wound around the proximal mouthpiece 53' one or more turns, and is retained onto the proximal mouthpiece 53' by the fastener $522_{31}$ under that condition.

Figure 78:
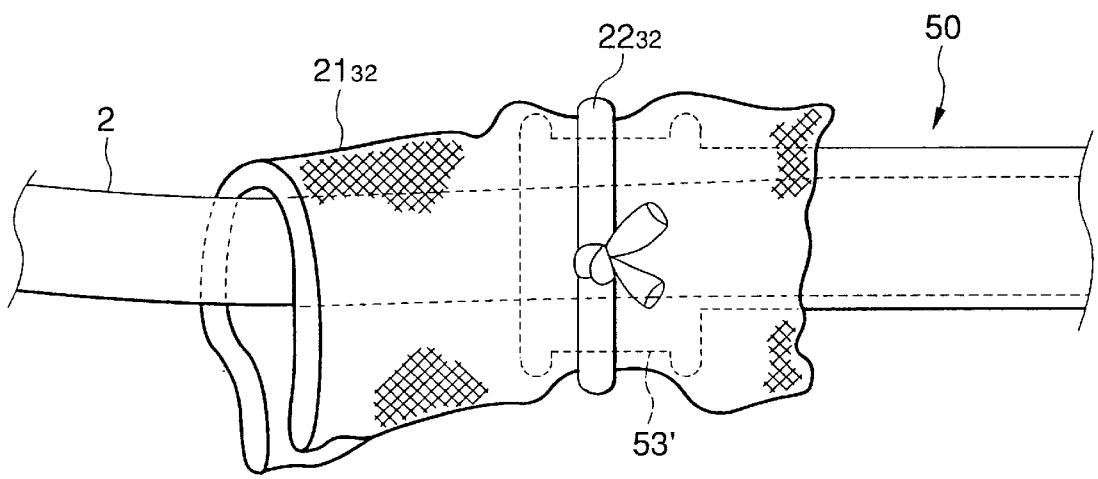
FIG. 78 is a side view which shows the usage condition in which a foul fluid splashing prevention device of a thirty-second embodiment of the present invention is attached to the sliding tube.
Figure 79:
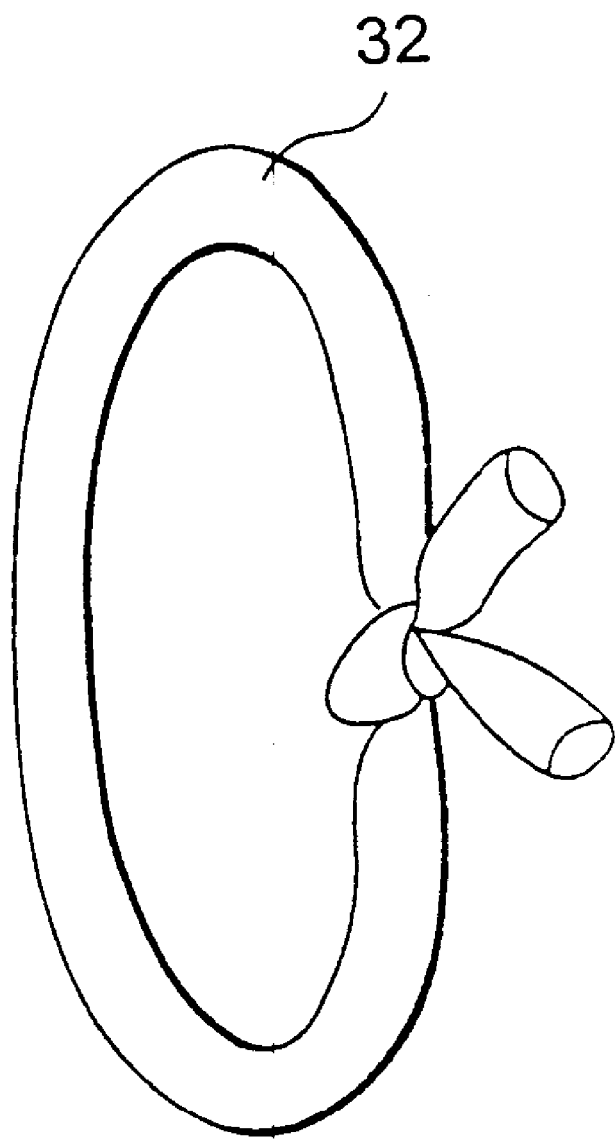
FIG. 79 is a perspective view of the retaining ring in the thirty-second embodiment of the present invention.

FIG. 78 shows another embodiment of the present invention in which a rubber-like string member is used as the retaining member $22_{32}$ for retaining the foul fluid absorbing member $21_{32}$ onto the outer peripheral surface of the proximal mouthpiece 53'. As best shown in FIG. 79, this retaining member $22_{32}$ is formed to have a ring-like form for example by tying both ends of a single rubber string.

Figure 80:
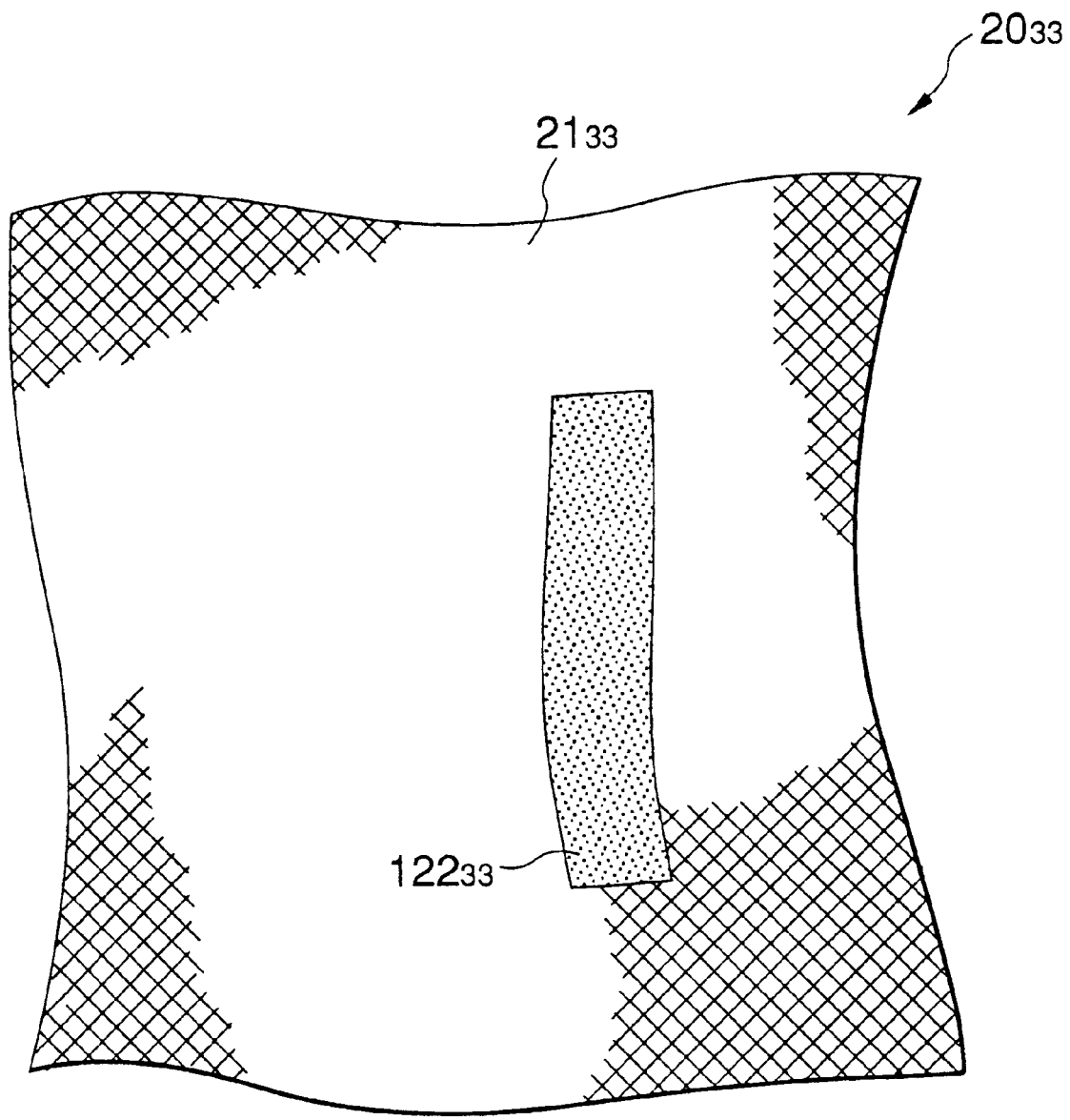
FIG. 80 is a developed view of a foul fluid splashing prevention device of a thirty-third embodiment of the present invention.
Figure 81:
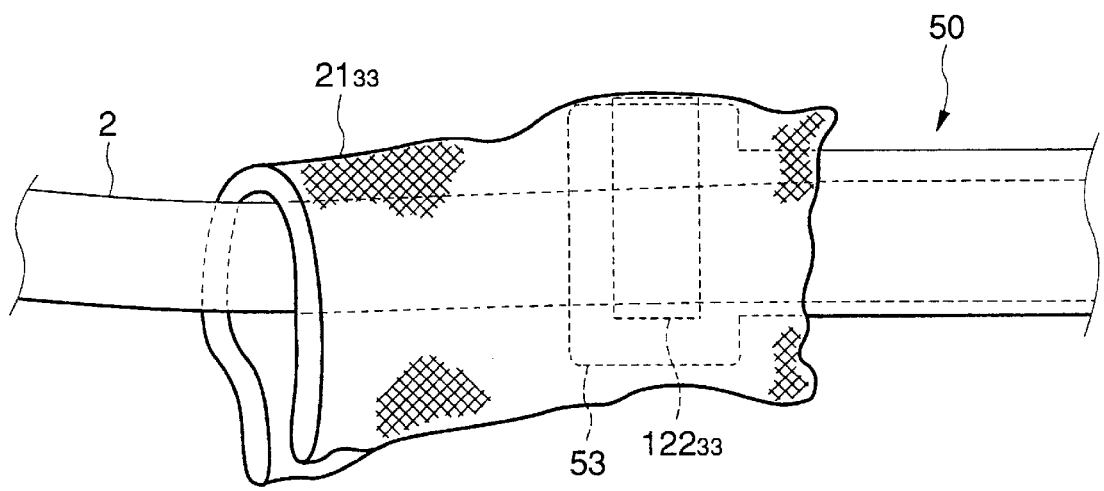
FIG. 81 is a side view of the usage condition in which the foul fluid splashing prevention device of the thirty-third embodiment of the present invention is attached to the sliding tube.

FIG. 80 shows another embodiment of the present invention in which a pressure-sensitive adhesive agent $122_{33}$ is applied to the portion of the foul fluid absorbing member $21_{33}$ that is to be attached to the proximal mouthpiece 53. FIG. 81 shows the condition in which this foul fluid absorbing member $21_{33}$ has been attached to the proximal mouthpiece 53. The foul fluid absorbing member $21_{33}$ is fixed and retained by adhesion to the proximal mouthpiece 53 by the pressing of the pressure-sensitive adhesive ($122_{33}$) portion of the foul fluid absorbing member $21_{33}$ from the outer side against the outer peripheral surface of the proximal mouthpiece 53. After use, the foul fluid absorbing member $21_{33}$ can be subjected to disposal upon peeling the pressure-sensitive adhesive $122_{33}$ from the proximal mouthpiece 53.

Figure 82:
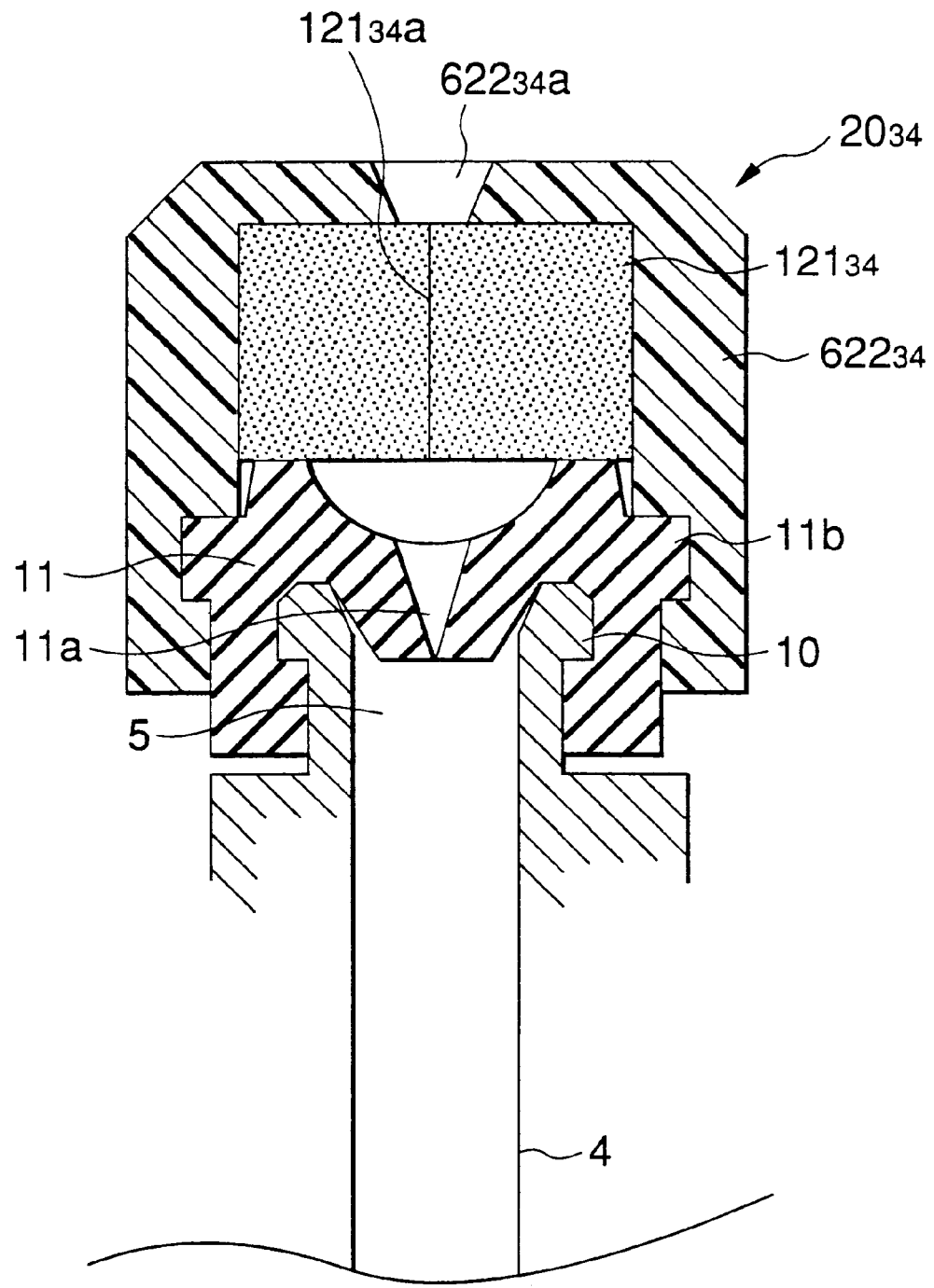
FIG. 82 is a longitudinal section view of a foul fluid splashing prevention device of a thirty-fourth embodiment of the present invention.
Figure 83:
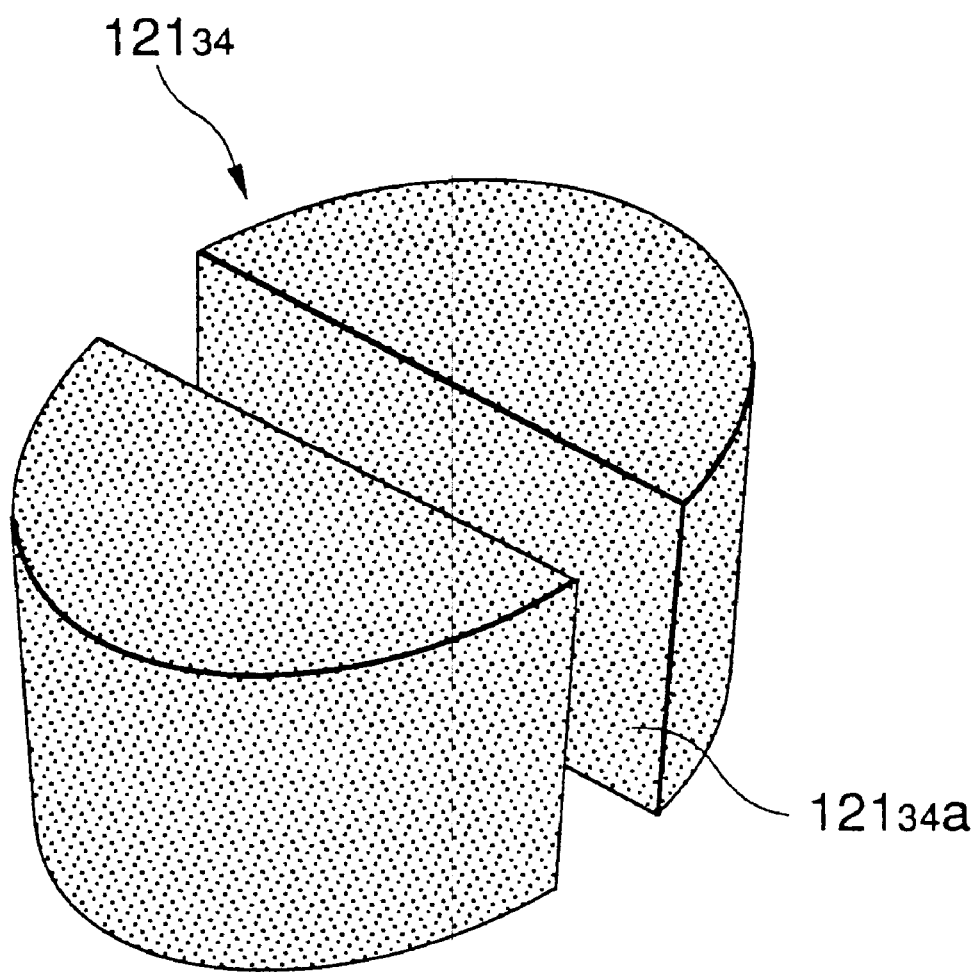
FIG. 83 is a perspective view of a foul fluid absorbing member in the thirty-fourth embodiment of the present invention.
Figure 84:
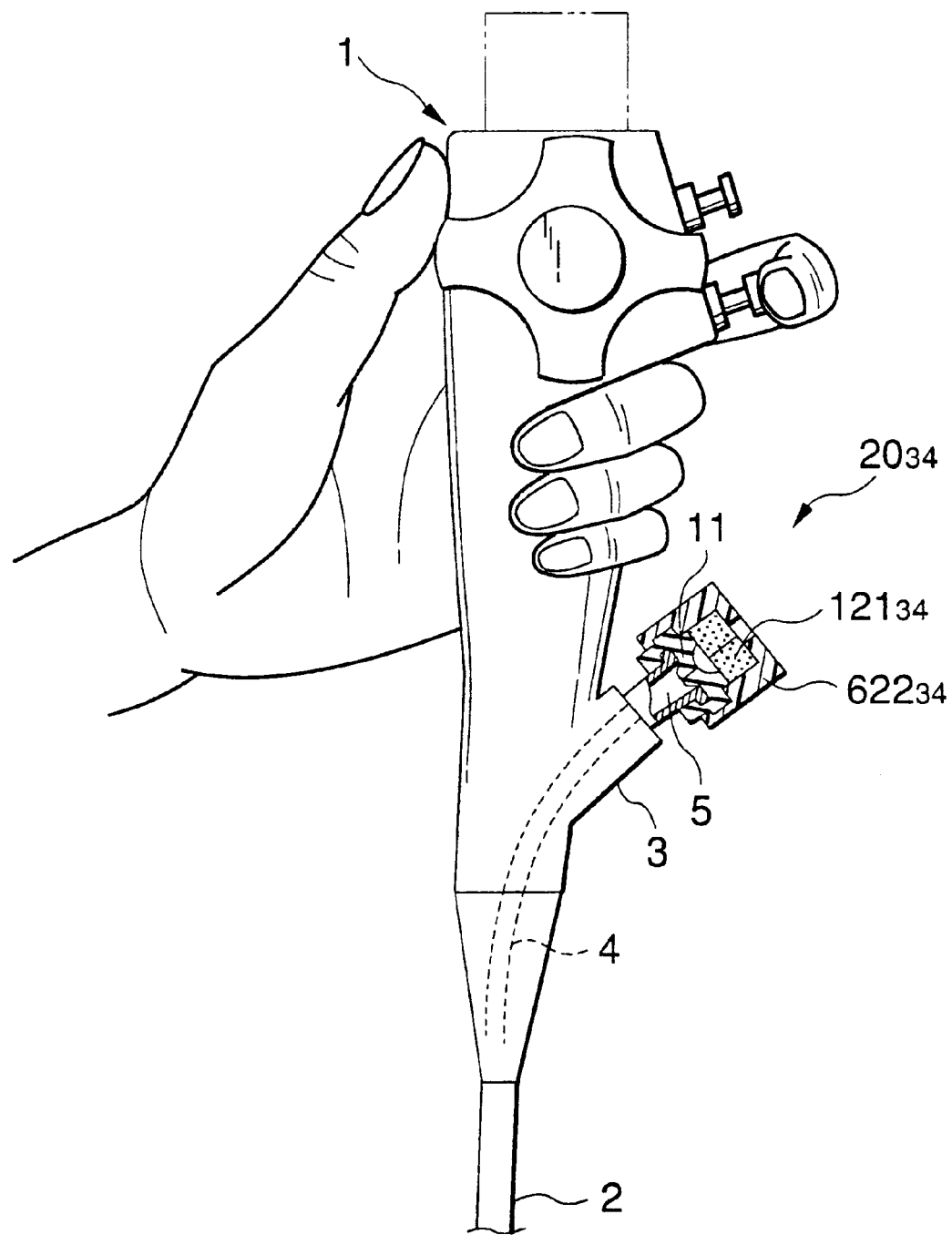
FIG. 84 is a side view partly in section of the manipulating part of the endoscope in the thirty-fourth embodiment of the present invention.

FIGS. 82 to 84 shows another embodiment of the present invention in which a foul fluid splashing preventive device $20_{34}$ including a foul fluid absorbing member and a retaining member is attached to the forceps plug 11.

FIG. 82 shows the operative instrument insertion entrance (5) portion in an enlarged manner. The forceps plug 11 is formed from a resilient rubber material. The central portion of the forceps plug 11 fits smoothly into the inside of the operative instrument insertion entrance 5 and a slit 11a is formed in this central portion.

A flange with which the forceps plug 11 engages is formed on the tip portion of a mouthpiece 10 protruding from the manipulating part 1. The forceps plug 11 is formed to have a shape that covers mouthpiece 10 in a closely contacting manner. Since forceps plug 11 has resilience, it can be attached and detached freely to and from the mouthpiece 10 while being deformed.

A foul fluid splashing prevention device $20_{34}$, for preventing the outward splashing of the foul fluids that leak out from slit 11a of the forceps plug 11, is detachably disposed on forceps plug 11.

The foul fluid splashing prevention device $20_{34}$ includes a foul fluid absorbing member $121_{34}$, formed from a resilient, water-absorbing, open-cell, foamed material, such as a sponge, which is fitted inside a plastic case (retaining member) $621_{34}$ having a cap-like shape with a hole $622_{34}a$ in the center.

As shown in FIG. 83, the foul fluid absorbing member $121_{34}$ is formed by dividing, for example, a short cylindrical member into two in the vertical direction along plane $121_{34}a$ that passes through the axis. And as shown in FIG. 82, the foul fluid absorbing member $121_{34}$ is positioned to face the entrance of the forceps plug 11 with the position of the central axis being matched with that of the forceps plug 11. The halves of the foul fluid absorbing member $121_{34}$ are in a closely contacting condition that prevents the forming of a gap in between. The foul fluid absorbing member $121_{34}$ can also be divided into three or more parts.

A flange 11b, with which the case or retaining member $622_{34}$ of the foul fluid splashing prevention device $20_{34}$ engages, protrudes from the outer peripheral surface of the forceps plug 11, and the case $622_{34}$ of the foul fluid splashing prevention device $20_{34}$ is formed to have a shape that covers the flange 11b in a closely contacting manner. And since the forceps plug 11 has resilience, it can be freely attached and detached while being deformed with respect to the case $622_{34}$.

With the embodiment formed in the above manner, even when the foul fluids from the inside of the body cavity leak out to the exterior from the forceps channel 4 via slit 11a of the forceps plug 11 due to the increased internal pressure of the body cavity, the foul fluid that has leaked out can be absorbed by the foul fluids absorbing member $123_{34}$ disposed immediately outside the slit 11a and can be collected inside the case $622_{34}$.

When an operative instrument is to be used, the operative instrument is passed through the hole $622_{34}a$ of the case $622_{34}$ and between division faces $121_{34}a$ of the foul fluid absorbing member $121_{34}$ while spreading the foul fluid absorbing member $121_{34}$ and being in close contact with division faces $121_{34}a$. Then the operative instrument is inserted into the forceps channel 4 from the operative instrument insertion entrance 5 while spreading slit 11a of forceps plug 11.

Although the amount of leakage of foul fluids from the slit 11a increases when the operative instrument is inserted into the forceps plug 11 in the above manner, the foul fluids that have leaked will be absorbed by foul fluid absorbing member $121_{34}$ and collected in the case $121_{34}$ even in this case.

When the operative instrument has been drawn out, the slit 11a of the forceps plug 11 and the division faces $121_{34}a$ of the foul fluid absorbing member $121_{34}$ are both closed by the resilience of the respective parts of themselves and return to the condition prior to the insertion of the operative instrument.

Figure 85:
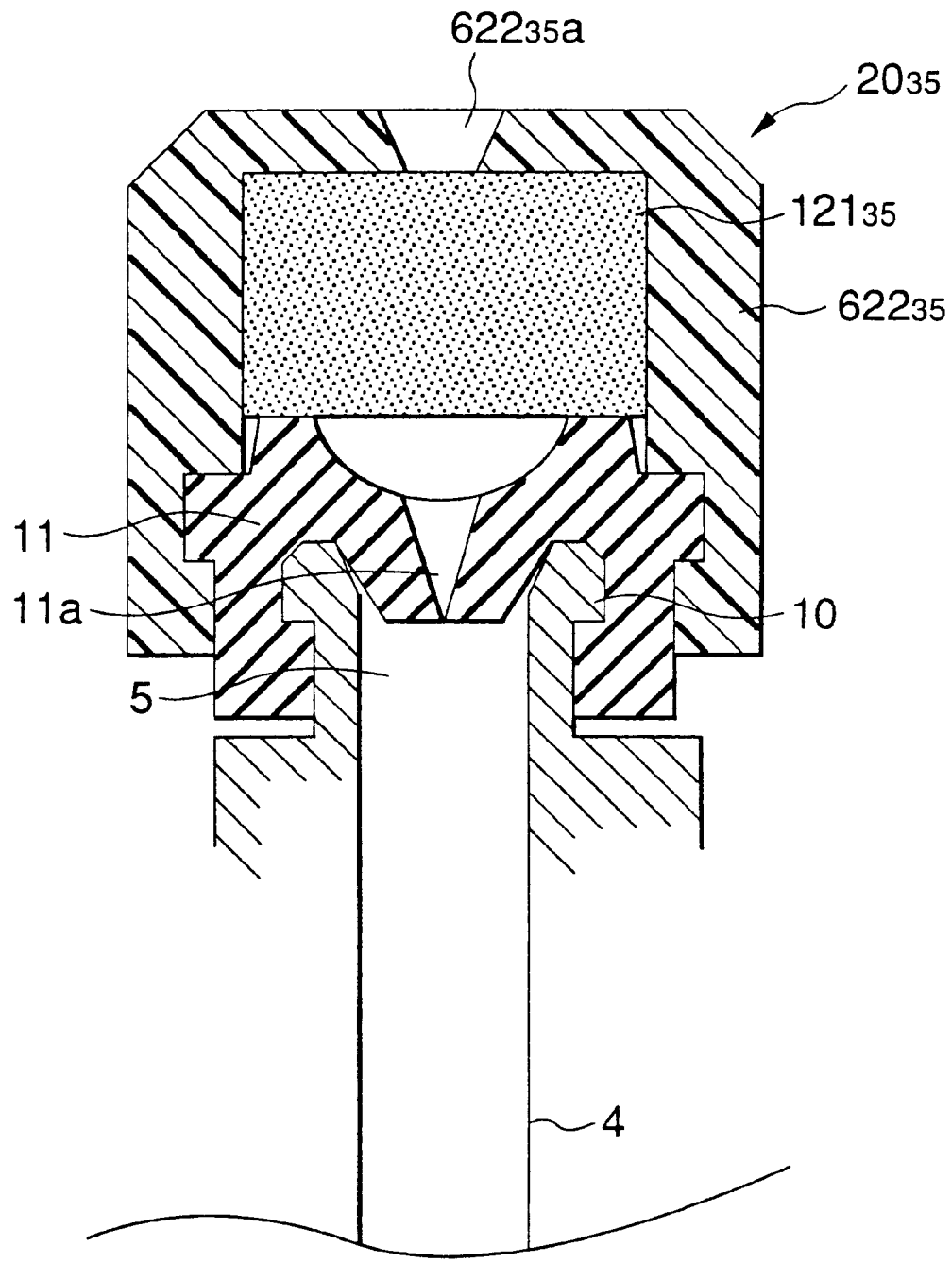
FIG. 85 is a longitudinal sectional view of a foul fluid splashing prevention device of a thirty-fifth embodiment of the present invention.

FIG. 85 shows another embodiment of the present invention in which the foul fluid absorbing member $121_{35}$ is formed as a single block from a weak water-absorbing material (for example, a sponge of high expansion or foam ratio and coarse foam density).

In this case, the foul fluid absorbing member $121_{35}$ is pierced by the operative instrument that is inserted. The embodiment shown in FIG. 86 can be used in the same manner as the embodiment shown in FIG. 82, and the fluid that leads out from slit 11a of forceps plug 11 can be absorbed by the foul fluid absorbing member $121_{35}$ and collected in the case $622_{35}$.

Figure 86:
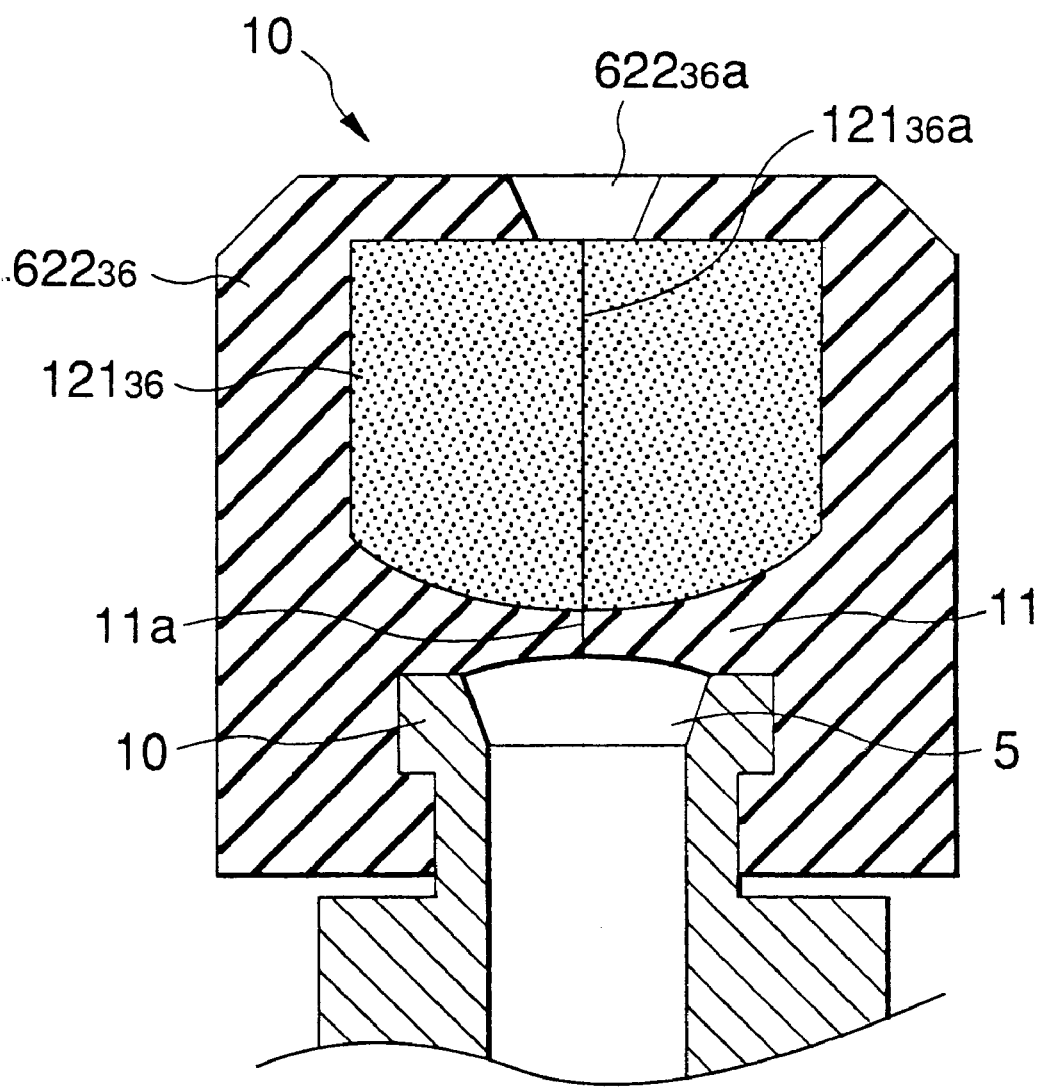
FIG. 86 is a longitudinal sectional view of a foul fluid splashing prevention device of a thirty-sixth embodiment of the present invention.

FIG. 86 shows another embodiment of the present invention in which the case $622_{36}$ of the foul fluid splashing invention in which the case $622_{36}$ of the foul fluid splashing prevention device $20_{36}$ and the forceps plug 11 are formed integrally from rubber material and the foul fluid absorbing member $121_{36}$ is fitted into this integral part, so that a single unit of the forceps plug 11 and the foul fluid splashing prevention device $20_{36}$ can be attached to and detached from the mouthpiece 10 of the operative instrument insertion entrance 5. Although the foul fluid absorbing member $121_{36}$ is divided into two pieces, it can also be formed as an integral piece.

With the above arrangement, not only the leakage of the foul fluids tot he exterior is reduced further but the number of parts is also reduced. Therefore, the manufacturing cost becomes lower, and it is possible to achieve the economical purpose even if the device is used as a disposal device.

What is claimed is:

1. A fluid splashing preventive device adapted for use with an endoscope, the endoscope defining an external opening which is in communication with a body cavity and through which fluids within the body cavity can escape, said fluid splashing preventive device comprising:

a retaining member; and a flexible, fluid absorbing member mountable onto the endoscope by said retaining member, said flexible, fluid absorbing member covering the external opening of the endoscope and absorbing escaping fluids, said retaining member extending for a predetermined distance along and on a surface of said fluid absorbing member.

2. A fluid splashing preventive device according to claim 1, wherein said retaining member includes an elastically contractible band member attached to said fluid absorbing member.

3. A fluid splashing preventive device according to claim 1, wherein said retaining member includes a pressure-sensitive adhesive material provided on said fluid absorbing member.

4. A fluid splasing preventive device according to claim 1, wherein said retaining member is detachably attachable to the endoscope.

5. A fluid splashing preventive device according to claim 1, wherein said absorbing member includes a gauze.

6. A fluid splashing preventive device according to claim 1, wherein said absorbing member includes a sponge.

7. The fluid splashing preventive device according to claim 6, said sponge having at least one slit extending longitudinally therethrough.

8. A fluid splashing preventive device accoridng to claim 1, wherein said absorbing member includes an open-cell material.

9. A fluid splashing preventive device according to claim 1, wherein said absorbing member includes a water-impregnable non-woven fabric.

10. A fluid splashing preventive device accoding to claim 1, wherein said absorbing memeber includes a high molecular weight water-impregnable polymer.

11. A fluid splashing preventive device adapted for use with an endoscope, the endoscope defining an external opening which is in communication with a body cavity and through which fluids within the body cavity can escape, said fluid splashing preventing device comprising:

a retaining member; and a flexible, fluid absorbing member mountable onto the endoscope by said retaining member, said flexible fluid absorbing member covering the external opening of the endoscope and absorbing escaping, said retaining member including a hole through which said fluid absorbing member passes.

12. A fluid splashing preventive device adapted for use with an endoscope, the endoscope defining an external opening which is in communication with a body cavity and through which fluids within the body cavity can escape, said fluid splashing preventing device comprising:

a retaining member; and a flexible, fluid absorbing member mountable onto the endoscope by said retaining member, said flexible fluid absorbing member covering the external opening of the endoscope and absorbing escaping fluids, said retaining member includes a flanged member attached to the endoscope.

13. A fluid splashing preventive device adapted for use with an endoscope, the endoscope defining an external opening which is in communication with a body cavity and through which fluids within the body cavity can escape, said fluid splashing preventing device comprising:

a retaining member; and a flexible, fluid absorbing member mountable onto the endoscope by said retaining member, said flexible fluid absorbing member covering the external opening of the endoscope and absorbing escaping fluids, said retaining member includes a plug member generally closing the external opening of the endoscope.

14. A fluid splashing preventive device adapted for use with an endoscope, the endoscope defining an external opening which is in communication with a body cavity and through which fluids within the body cavity can escape, said fluid splashing preventing device comprising:

a retaining member; and a flexible, fluid absorbing member mountable onto the endoscope by said retaining member, said flexible fluid absorbing member covering the external opening of the endoscope and absorbing escaping fluids, said retaining member includes a case attachable to the endoscope with said fluid absorbing member accommodated in said case.

15. The fluid splashing preventive device according to claim 14, said case including a forceps plug formed integrally with said retaining member.

16. The fluid splashing preventive device according to claim 14, said fluid absorbing member comprising a single block of sponge.

17. The fluid splashing preventive device according to claim 14, said fluid absorbing member comprising a block of sponge having a slit therein.

18. A fluid splashing preventive device adapted for use with an endoscope, the endoscope defining an external opening which is in communication with a body cavity and through which fluids within the body cavity can escape, said fluid splashing preventing device comprising:

a retaining member;

a flexible, fluid absorbing member mountable onto the endoscope by said retaining member, said flexible fluid absorbing member covering the external opening of the endoscope and absorbing escaping fluids, and a sliding tube into which a portion of the endoscope is inserted, wherein the endoscope defines the external opening in relation to said sliding tube, and wherein said fluid absorbing member is mountable to said sliding tube by said retaining member.

19. A fluid splashing preventive device for an endoscope having an insertion part and a manipulation part, the manipulation part having an external opening which is in communication with a body cavity through the insertion part, said fluid splashing preventive device comprising:

a retaining member; and a flexible, fluid absorbing member mountable onto the manipulating part in the vicinity of the external opening by said retaining member, said retaining member extending for a predetermined distance along and on a surface of said fluid absorbing member.

20. A fluid splashing preventive device according to claim 19, wherein said retaining member is detachably attachable to the endoscope.

21. The fluid splashing preventive device according to claim 19, wherein said retaining member includes a band member adapted to circumscribe the manipulation part with said fluid absorbing member retained between said band member and the manipulation part.

22. A fluid splashing preventive device according to claim 19, wherein said retaining member includes a pressure-sensitive adhesive member adapted to be detachably connected to the manipulation part to retain said fluid absorbing member on the manipulation part under pressure.

23. A fluid splashing preventive device for an endoscope having an insertion part and a manipulation part, the manipulation part having an external opening which is in communication with a body cavity through the insertion part, said fluid splashing preventive device comprising:

a retaining member; and a flexible fluid absorbing member mountable onto the manipulation part in the vicinity of the external opening by said retaining member said retaining member including a band member adapted to circumscribe the manipulation part with said fluid absorbing member retained between said band member and the manipulation part said flexible fluid absorbing member is folded to form an opening, and said band member extends through said opening.

24. A fluid splashing preventive device according to claim 23, wherein said band member includes a retaining ring at each end.

25. A fluid splashing preventive device according to claim 24, wherein the manipulation part includes a protruded portion, said retaining member being retained on said protruded portion.

26. A fluid splashing preventive device for an endoscope having an insertion part and a manipulation part, the manipulation part having an external opening which is in communication with a body cavity through the insertion part, said fluid splashing preventive device comprising:

a retaining member; and a flexible fluid absorbing member mountable onto the manipulation part in the vicinity of the external opening by said retainer member the external opening is provided on a protruded portion of a forceps channel on the manipulation part, and wherein said retaining member includes a hole portion formed through said absorbing member adapted to be fitted to the protruded portion.

27. A fluid splashing preventive device according to claim 26, wherein said retaining member further includes a flange formed on a forceps plug, said forceps plug substantially closing the external opening.

28. A fluid splashing preventive device according to claim 26, wherein said retaining member further includes a resilient member adapted to engage the protruded portion with said hole portion located between said pressure member and an external surface of the manipulation part.

29. A fluid splashing preventive device according to claim 28, further comprising a forceps plug substantially closing said external opening, wherein said pressure member is distinct from said forceps plug.

30. A fluid splashing preventive device for an endoscope having an insertion part and a manipulation part, the manipulation part having an external opening which is in communication with a body cavity through the insertion part, said fluid splashing preventive device comprising:

a retaining member; and a flexible fluid absorbing member mountable onto the manipulation part in the vicinity of the external opening by said retainer member said retaining member further includes a flange formed on a forceps plug, said forceps plug substantially closing the external opening.

31. A fluid splashing preventive device for an endoscope having an insertion part and a manipulation part, the manipulation part having an external opening which is in communication with a body cavity through the insertion part, said fluid splashing preventive device comprising:

a retaining member; and a flexible fluid absorbing member mountable onto the manipulation part in the vicinity of the external opening by said retainer member said retaining member includes a portion of a forceps plug, said portion being adapted to clamp said absorbing member between said portion and an external surface of the manipulation part.

32. A fluid splashing preventive device for an endoscope having an insertion part and a manipulation part, the manipulation part having an external opening which is in communication with a body cavity through the insertion part, said fluid splashing preventive device comprising:

a retaining member; and a first flexible fluid absorbing member mountable onto the manipulation part in the vicinity of the external opening by said retainer member a second absorbing member mountable onto the manipulation part and located adjacent said first fluid absorbing member.

33. A fluid splashing preventive device according to claim 32, wherein at least a portion of said first and second absorbing members overlap each other.

34. A fluid splashing preventive device according to claim 32, wherein said retaining member includes a C-shaped, elastically deformable fastener adapted to clamp both of said first and second absorbing members.

35. A fluid splashing preventive device for an endoscope having an insertion part and a manipulation part, the manipulation part having an external opening which is in communication with a body cavity through the insertion part, said fluid splashing preventive device comprising:

a retaining member; and a flexible fluid absorbing member mountable onto the manipulation part in the vicinity of the external opening by said retainer member the endoscope including a forceps plug substantially closing the external opening and said retaining member includes a case adapted to be mounted on the forceps plug with said absorbing member accommodated between said case and the forceps plug.

36. A fluid splashing preventive device for a flexible, tubular endoscope insertion guiding device inserted into an opening in a body to guide an inserted part of an endoscope towards a body cavity, the guiding device having a proximal end through which the inserted part of the endoscope is inserted into an inside of the guiding device, said fluid splashing preventive device comprising:

a retaining member; and a flexible, fluid absorbing member mounted onto the guiding device in the vicinity of the proximal end by said retaining member, said retaining member extending for a predetermined distance along and on a surface of said fluid absorbing member.

37. A fluid splashing preventive device according to claim 36, wherein said retaining member includes a pressure-sensitive adhesive member detachably retaining said fluid absorbing member on an external surface of said guiding device.

38. A fluid splashing preventive device for a flexible, tubular endoscope insertion guiding device inserted into an opening in a body to guide an inserted part of an endoscope towards a body cavity, the guiding device having a proximal end through which the inserted part of the endoscope is inserted into an inside of the guiding device, said fluid splashing preventive device comprising:

a retaining member; and a flexible fluid absorbing member mountable onto the guiding device in the vicinity of the proximal end by said retaining member, said retaining member including a C-shaped, elastically deformable fastener adapted to elastically clamp said absorbing member between said C-shaped fastener and an external surface of the guiding device the proximal end of the guiding device including spaced flanges, said C-shaped fastener being positioned between the spaced flanges to restrict axial movement of said C-shaped fastener.

39. A fluid splashing preventive device for a flexible, tubular endoscope insertion guiding device inserted into an opening in a body to guide an inserted part of an endoscope towards a body cavity, the guiding device having a proximal end through which the inserted part of the endoscope is inserted into an inside of the guiding device, said fluid splashing preventive device comprising:

a retaining member; and a flexible fluid absorbing member mountable onto the guiding device in the vicinity of the proximal end by said retaining member, said retaining member includes a C-shaped, elastically deformable fastener adapted to elastically clamp said absorbing member between said C-shaped fastener and an external surface of the guiding device the proximal end of the guiding device including flat parts on side surfaces of the proximal end, said C-shaped fastener being positioned at the flat parts to restrict axial movement of said C-shaped fastener.

40. A fluid splashing preventive device for a flexible, tubular endoscope insertion guiding device inserted into an opening in a body to guide an inserted part of an endoscope towards a body cavity, the guiding device having a proximal end through which the inserted part of the endoscope is inserted into an inside of the guiding device, said fluid splashing preventive device comprising:

a retaining member; and a flexible fluid absorbing member mountable onto the guiding device in the vicinity of the proximal end by said retaining member said retaining member includes a band member adapted to circumscribe an external surface of the guiding device, said fluid absorbing member being retained between said band member and the external surface of the guiding device.

41. An endoscope having a fluid splashing preventive device, said endoscope comprising:

an insertion part;

a manipulation part, said manipulation part having an external opening which is in communication with a body cavity through said insertion part;

a retaining member; and a flexible, fluid absorbing member mountable onto said manipulation part of said endoscope in a vicinity of said external opening by said retaining member, said retaining member including a band which extends for a predetermined distance along and on a surface of said fluid absorbing member, said absorbing member being mountable to a portion of said manipulating section of said endoscope by said band member, said fluid absorbing member covering an opening provided in said manipulating portion.

42. The endoscope according to claim 41, said retaining member comprising an elastically contractible band member attached to said fluid absorbing member.

43. The endoscope according to claim 41, said retaining member comprising a pressure sensitive adhesive material provided on said fluid absorbing member.

44. A fluid splashing preventive device adapted for use with an endoscope, the endoscope defining an external opening which is in communication with a body cavity and through which fluids within the body cavity can escape, said fluid splashing preventive device comprising:

a retaining member; and a flexible, fluid absorbing member mountable onto the endoscope by said retaining member, said flexible, fluid absorbing member covering the external opening and absorbing escaping fluids, said retaining member being an elastically deformable member, said retaining member comprising two C-shaped elements spaced from each other and connected by a pair of connecting elements, said connecting elements and said C-shaped elements defining an opening in said retaining member.

45. A fluid splashing preventive device for an endoscope having an insertion part and a manipulation part, the manipulation part having an external opening which is in communication with a body cavity through the insertion part, said fluid splashing preventive device comprising:

an elastically deformable retaining member, said retaining member comprising two spaced C-shaped elements, said two C-shaped elements connected by two connecting elements; and a flexible, fluid absorbing member mountable onto the endoscope by said retaining member, said flexible, fluid absorbing member covering the external opening and absorbing escaping fluids, said retaining member adapted to clamp said absorbing member between said C-shaped elements and the manipulation part.

46. The fluid splashing preventive device according to claim 45, said retaining member comprising a longitudinally extending cylindrical member having a C-shape in cross section, said connecting elements defining an aperture defining through which a protruding portion of the endoscope can pass.

47. The fluid splashing preventive device according to claim 45, said C-shaped elements and said connecting elements of said retaining member forming a continuous semi-cylindrical outer surface.

48. The fluid splashing preventive device according to claim 45, said connecting elements having a generally inward curvature extending along a longitudinal direction, said C-shaped elements including outwardly expandable tab members which, when said retaining member is installed on an endoscope, provide a space between said tab member and the endoscope to which the retaining member is mounted.

49. The fluid splashing preventive device according to claim 45, the manipulation part including a protruded portion of a forceps channel, said C-shaped elements and said connecting elements of said retaining member defining an opening, the protruding portion of the forceps channel of the endoscope extending through said opening of said retaining member.

50. A fluid splashing preventive device for a flexible, tubular endoscope insertion guiding device inserted into an opening in a body to guide an inserted part of an endoscope towards a body cavity, the guiding device having a proximal end through which the inserted part of the endoscope is inserted into an inside of the guiding device, said fluid splashing preventive device comprising:

an elastically deformable retaining member; and a flexible, fluid absorbing member mountable onto the guiding device in the vicinity of the proximal end by said retaining member, said retaining member comprising two spaced C-shaped elements connected by two connecting elements, said retaining member adapted to elastically clamp said absorbing member between said retaining member and an external surface of the guiding device.

51. The fluid splashing preventive device according to claim 50, said retaining member including stopper protrusions engaging a portion of the proximal end of the guiding device to restrict axial movement of said retaining member.

* * * * *